United States Patent
Marzabadi et al.

(10) Patent No.: US 7,473,698 B2
(45) Date of Patent: Jan. 6, 2009

(54) SECONDARY AMINO ANILINIC PIPERIDINES AS MCH1 ANTAGONISTS AND USES THEREOF

(75) Inventors: Mohammad R. Marzabadi, Ridgewood, NJ (US); Yu Jiang, Jersey City, NJ (US); Kai Lu, Lake Hiawatha, NJ (US); Chien-An Chen, Flushing, NY (US); John E. De Leon, North Bergen, NJ (US); John Wetzel, Fairlawn, NJ (US)

(73) Assignee: H. Lunbeck A/S, Valby - Copenhagen (DK)

( * ) Notice: Subject to any disclaimer, the term of this patent is extended or adjusted under 35 U.S.C. 154(b) by 558 days.

(21) Appl. No.: 10/518,675

(22) PCT Filed: Jul. 3, 2003

(86) PCT No.: PCT/US03/21391

§ 371 (c)(1),
(2), (4) Date: Dec. 17, 2004

(87) PCT Pub. No.: WO2004/005257

PCT Pub. Date: Jan. 15, 2004

(65) Prior Publication Data

US 2005/0245743 A1    Nov. 3, 2005

(51) Int. Cl.
*A61K 31/4465* (2006.01)
(52) U.S. Cl. .................... 514/331; 546/234
(58) Field of Classification Search .............. 544/180; 514/331; 546/234
See application file for complete search history.

(56) References Cited

U.S. PATENT DOCUMENTS

| 4,721,723 A | 1/1988 | Barnes et al. |
| 6,503,928 B2 | 1/2003 | Kelly et al. |
| 2003/0082623 A1* | 5/2003 | Borowsky et al. ............ 435/7.1 |

FOREIGN PATENT DOCUMENTS

| WO | WO 97/28140 | | 8/1997 |
| WO | WO 02/06245 | | 1/2002 |
| WO | WO0202744 | * | 1/2002 |
| WO | WO0202744 A | * | 1/2002 |
| WO | WO 02/094799 | | 11/2002 |
| WO | WO 03/004027 | | 1/2003 |

OTHER PUBLICATIONS

Guo et al., "Discovery and SAR of biaryl piperidine MCH1 receptor antagonists through solid-phase encoded combinatorial synthesis" Bioorganic & Medicinal Chemistry Letters 2005, 15, 3696-3700.*
Takekawa, S., et al., "T-226296: a novel, orally active and selective melanin-concentrating hormone receptor antagonist", European Journal of Pharmacology, Mar. 2002, 438, pp. 129-135.

* cited by examiner

Primary Examiner—Rita J. Desai
Assistant Examiner—David K O'Dell
(74) Attorney, Agent, or Firm—Kitae Lim

(57) ABSTRACT

This invention is directed to compounds which are selective antagonists for melanin concentrating hormone-1 (MCH1) receptors. The invention provides a pharmaceutical composition comprising a therapeutically effective amount of the compound of the invention and a pharmaceutically acceptable carrier. This invention provides a pharmaceutical composition made by combining a therapeutically effective amount of the compound of this invention and a pharmaceutically acceptable carrier. This invention further provides a process for making a pharmaceutical composition comprising combining a therapeutically effective amount of the compounds of the invention and a pharmaceutically acceptable carrier. This invention also provides a method of reducing the body mass of a subject which comprises administering to the subject an amount of a compound of the invention effective to reduce the body mass of the subject. This invention further provides a method of treating a subject suffering from depression and/or anxiety which comprises administering to the subject an amount of a compound of the invention effective to treat the subject=s depression and/or anxiety. This invention further provides a method of treating a subject suffering from a urinary disorder.

21 Claims, No Drawings

SECONDARY AMINO ANILINIC PIPERIDINES AS MCH1 ANTAGONISTS AND USES THEREOF

This application is a §371 national stage of PCT International Application No. PCT/US2003/021391, filed Jul. 3, 2003 on behalf of H. Lundbeck A/S, which claims priority of U.S. Ser. No. 10/189,145, filed Jul. 3, 2002, now abandoned, the contents of which are hereby incorporated by reference into the subject application.

Throughout this application, various publications are referenced in parentheses by author and year. Full citations for these references may be found at the end of the specification immediately preceding the claims.

The disclosure of these publications in their entireties are hereby incorporated by reference into this application to describe more fully the state of the art to which this invention pertains.

BACKGROUND OF THE INVENTION

Melanin-concentrating hormone (MCH) is a cyclic peptide originally isolated from salmonid (teleost fish) pituitaries (Kawauchi et al., 1983). In fish the 17 amino acid peptide causes aggregation of melanin within the melanophores and inhibits the release of ACTH, acting as a functional antagonist of α-MSH. Mammalian MCH (19 amino acids) is highly conserved between rat, mouse, and human, exhibiting 100% amino acid identity, but its physiological roles are less clear. MCH has been reported to participate in a variety of processes including feeding, water balance, energy metabolism, general arousal/attention state, memory and cognitive functions, and psychiatric disorders (for reviews, see Baker, 1991; Baker, 1994; Nahon, 1994; Knigge et al., 1996). Its role in feeding or body weight regulation is supported by a recent Nature publication (Qu et al., 1996) demonstrating that MCH is overexpressed in the hypothalamus of ob/ob mice compared with ob/+ mice, and that fasting further increased MCH mRNA in both obese and normal mice during fasting. MCH also stimulated feeding in normal rats when injected into the lateral ventricles (Rossi et al., 1997).

MCH also has been reported to functionally antagonize the behavioral effects of α-MSH (Miller et al., 1993; Gonzalez et al, 1996; Sanchez et al., 1997); in addition, stress has been shown to increase POMC mRNA levels while decreasing the MCH precursor preproMCH (ppMCH) mRNA levels (Presse et al., 1992). Thus MCH may serve as an integrative neuropeptide involved in the reaction to stress, as well as in the regulation of feeding and sexual activity (Baker, 1991; Knigge et al., 1996).

The biological effects of MCH are believed to be mediated by specific receptors. A tritiated ligand ([$^3$H]-MCH) was reported to exhibit specific binding to brain membranes but was unusable for saturation analyses, so neither affinity nor $B_{max}$ were determined (Drozdz and Eberle, 1995). Radioiodination of the tyrosine at position thirteen resulted in a ligand with dramatically reduced biological activity (see Drozdz and Eberle, 1995). In contrast, the radioiodination of the MCH analogue [Phe$^{13}$,Tyr$^{19}$]-MCH was successful (Drozdz et al., 1995); the ligand retained biological activity and exhibited specific binding to a variety of cell lines including mouse melanoma (B16-F1, G4F, and G4F-7), PC12, and COS cells.

In G4F-7 cells, the $K_D$=0.118 nM and the $B_{max}$ ~1100 sites/cell. Importantly, the binding was not inhibited by α-MSH but was weakly inhibited by rat ANF (Ki=116 nM vs. 12 nM for native MCH) (Drozdz et al., 1995). More recently specific MCH binding was reported in transformed keratinocytes (Burgaud et al., 1997) and melanoma cells (Drozdz et al., 1998), where photo-crosslinking studies suggest that the receptor is a membrane protein with an apparent molecular weight of 45-50 kDaltons, compatible with the molecular weight range of the GPCR superfamily of receptors. No radioautoradiographic studies of MCH receptor localization using this ligand have been reported as yet.

The localization and biological activities of MCH peptide suggest that the modulation of MCH receptor activity may be useful in a number of therapeutic applications. The role of MCH in feeding is the best characterized of its potential clinical uses. MCH is expressed in the lateral hypothalamus, a brain area implicated in the regulation of thirst and hunger (Grillon et al., 1997); recently orexins A and B, which are potent orexigenic agents, have been shown to have very similar localization to MCH in the lateral hypothalamus (Sakurai et al., 1998). MCH mRNA levels in this brain region are increased in rats after 24 hours of food-deprivation (Hervé and Fellman, 1997); after insulin injection, a significant increase in the abundance and staining intensity of MCH immunoreactive perikarya and fibres was observed concurrent with a significant increase in the level of MCH mRNA (Bahjaoui-Bouhaddi et al., 1994).

Consistent with the ability of MCH to stimulate feeding in rats (Rossi et al., 1997) is the observation that MCH mRNA levels are upregulated in the hypothalami of obese ob/ob mice (Qu et al., 1996), and decreased in the hypothalami of rats treated with leptin, whose food intake and body weight gains are also decreased (Sahu, 1998). MCH appears to act as a functional antagonist of the melanocortin system in its effects on food intake and on hormone secretion within the HPA (hypothalamopituitary/adrenal axis) (Ludwig et al., 1998). Together these data suggest a role for endogenous MCH in the regulation of energy balance and response to stress, and provide a rationale for the development of specific compounds acting at MCH receptors for use in the treatment of obesity and stress-related disorders.

In all species studied to date, a major portion of the neurons of the MCH cell group occupies a rather constant location in those areas of the lateral hypothalamus and subthalamus where they lie and may be a part of some of the so-called "extrapyramidal" motor circuits. These involve substantial striato- and pallidofugal pathways involving the thalamus and cerebral cortex, hypothalamic areas, and reciprocal connections to subthalamic nucleus, substantia nigra, and mid-brain centers (Bittencourt et al., 1992). In their location, the MCH cell group may offer a bridge or mechanism for expressing hypothalamic visceral activity with appropriate and coordinated motor activity. Clinically it may be of some value to consider the involvement of this MCH system in movement disorders, such as Parkinson=s disease and Huntingdon's Chorea in which extrapyramidal circuits are known to be involved.

Human genetic linkage studies have located authentic hMCH loci on chromosome 12 (12q23-24) and the variant hMCH loci on chromosome 5 (5q12-13) (Pedeutour et al., 1994). Locus 12q23-24 coincides with a locus to which autosomal dominant cerebellar ataxia type II (SCA2) has been mapped (Auburger et al., 1992; Twells et al., 1992). This disease comprises neurodegenerative disorders, including an olivopontocerebellar atrophy.

Furthermore, the gene for Darier's disease, has been mapped to locus 12q23-24 (Craddock et al., 1993). Darier's disease is characterized by abnormalities I keratinocyte adhesion and mental illnesses in some families. In view of the functional and neuroanatomical patterns of the MCH neural system in the rat and human brains, the MCH gene may represent a good candidate for SCA2 or Darier's disease. Interestingly, diseases with high social impact have been mapped to this locus. Indeed, the gene responsible for chronic or acute forms of spinal muscular atrophies has been assigned to chromosome 5q12-13 using genetic linkage analysis (Melki et al., 1990; Westbrook et al., 1992). Furthermore, independent lines of evidence support the assignment of a major schizophrenia locus to chromosome 5q11.2-13.3 (Sherrington et al., 1988; Bassett et al., 1988; Gilliam et al., 1989). The above studies suggest that MCH may play a role in neurodegenerative diseases and disorders of emotion.

Additional therapeutic applications for MCH-related compounds are suggested by the observed effects of MCH in other biological systems. For example, MCH may regulate reproductive functions in male and female rats. MCH transcripts and MCH peptide were found within germ cells in testes of adult rats, suggesting that MCH may participate in stem cell renewal and/or differentiation of early spermatocytes (Hervieu et al., 1996). MCH injected directly into the medial preoptic area (MPOA) or ventromedial nucleus (VMN) stimulated sexual activity in female rats (Gonzalez et al., 1996). In ovariectomized rats primed with estradiol, MCH stimulated luteinizing hormone (LH) release while anti-MCH antiserum inhibited LH release (Gonzalez et al., 1997). The zona incerta, which contains a large population of MCH cell bodies, has previously been identified as a regulatory site for the pre-ovulatory LH surge (MacKenzie et al., 1984).

MCH has been reported to influence release of pituitary hormones including ACTH and oxytocin. MCH analogues may also be useful in treating epilepsy. In the PTZ seizure model, injection of MCH prior to seizure induction prevented seizure activity in both rats and guinea pigs, suggesting that MCH-containing neurons may participate in the neural circuitry underlying PTZ-induced seizure (Knigge and Wagner, 1997). MCH has also been observed to affect behavioral correlates of cognitive functions. MCH treatment hastened extinction of the passive avoidance response in rats (McBride et al., 1994), raising the possibility that MCH receptor antagonists may be beneficial for memory storage and/or retention. A possible role for MCH in the modulation or perception of pain is supported by the dense innervation of the periaqueductal grey (PAG) by MCH-positive fibers. Finally, MCH may participate in the regulation of fluid intake. ICV infusion of MCH in conscious sheep produced diuretic, natriuretic, and kaliuretic changes in response to increased plasma volume (Parkes, 1996). Together with anatomical data reporting the presence of MCH in fluid regulatory areas of the brain, the results indicate that MCH may be an important peptide involved in the central control of fluid homeostasis in mammals.

The identification of a G-protein coupled receptor for MCH has recently been published (Chambers et al., 1999; Saito et al., 1999). These groups identified MCH as the endogenous ligand for the human orphan G-protein coupled receptor SLC-1 (Lakaye et al., 1998). The rat homologue of this receptor (now called MCH-1) was reported to be localized in regions of the rat brain associated with feeding behavior (e.g. dorsomedial and ventromedial hypothalamus). The link between MCH-1 and the effects of MCH on feeding has been strengthened by recent reports on the phenotype of MCH-1 knockout mice. Two groups have shown independently (Marsh et al, 2002; Chen et al, 2002) that the targeted disruption of the MCH-1 receptor gene (MCH-1 knockout) in mice results in animals that are hyperphagic but are lean and have decreased body mass relative to wild-type littermates. The decrease in body mass is attributed to an increase in metabolism. Each group demonstrated that the MCH-1 knockout mice are resistant to diet-induced obesity, and generally exhibit weights similar to littermates maintained on regular chow.

Finally, synthetic antagonist molecules for the MCH-1 receptor have now been described in the literature. Bednarek et al. (2002) have reported on the synthesis of high affinity peptide antagonists of MCH-1. In addition, a small molecule antagonist of MCH-1 has been described by Takekawa et al. (Takekawa et al., 2002). This compound, T-226296, exhibits high affinity for the MCH-1 receptor (~5-9 nM for rat and human MCH-1), and was shown to inhibit food intake induced by the intracerebroventricular application of MCH. These data validate the strategy of using an MCH-1 receptor antagonist to treat obesity.

Furthermore, in our own studies, we have tested MCH1 antagonists in several animal models that are well known as predictive for the efficacy of compounds in humans (Borowsky, et al., Nature Medicine 2003). These experiments indicate that MCH1 antagonists are useful to treat obesity, depression, anxiety, as well as urinary disorders.

Herein, we report the synthesis of secondary amino anilinic piperidines that bind to the cloned human melanin-concentrating hormone-1 (MCH1) receptor. Additionally, these compounds selectively bind to the MCH1-receptor against other cloned G-protein coupled receptor. The ability to inhibit the activation of the cloned receptor as measured in in vitro assays is disclosed.

Furthermore, the compounds of the present invention may also be used to treat abnormal conditions mediated by inactivation of the MCH-1 receptor such as feeding disorders (obesity, bulimia and bulimia nervosa), sexual/reproductive disorders, depression, anxiety, depression and anxiety, epileptic seizure, hypertension, cerebral hemorrhage, congestive heart failure, sleep disturbances, or any condition in which antagonism of an MCH1 receptor may be beneficial.

In addition, the compounds of the present invention may be used to reduce the body mass of a subject. Furthermore, the compounds of the present invention may be used to treat urinary disorders.

SUMMARY OF THE INVENTION

This invention provides a compound having the structure:

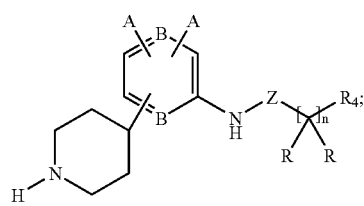

wherein each A is independently —H, —F, —Cl, —Br, —I, —CN, —NO$_2$, —OR$_3$ or straight chained or branched C$_1$-C$_7$ alkyl;
wherein each B is independently N or CH;
wherein Z is CO or SO$_2$;
wherein each R is independently —H, —F or straight chained or branched C$_1$-C$_7$ alkyl, monofluoroalkyl or polyfluoroalkyl;

wherein $R_4$ is independently —$OR_3$, —$NHR_3$, —$SR_3$, —$COR_3$, straight chained or branched $C_1$-$C_7$ alkyl, monofluoroalkyl or polyfluoroalkyl, aryl or heteroaryl, wherein the aryl or heteroaryl is optionally substituted with one or more —F, —Cl, —Br, —I, —$OR_2$, or straight chained or branched $C_1$-$C_7$ alkyl;

wherein each $R_3$ is independently —H; straight chained or branched $C_1$-$C_7$ alkyl, monofluoroalkyl or polyfluoroalkyl; aryl or heteroaryl, wherein the aryl or heteroaryl is optionally substituted with one or more —F, —Cl, —Br, —I, —$NO_2$, —CN, —$OR_2$, or —$NHR_2$;

wherein each $R_2$ is independently —H, straight chained or branched $C_1$-$C_7$ alkyl, aryl or heteroaryl, wherein the aryl or heteroaryl is optionally substituted with one or more —F, —Cl, —Br, —I, —$NO_2$, —CN; and wherein n is an integer from 1 to 6 inclusive;

or a pharmaceutically acceptable salt thereof.

In a further embodiment of the aforementioned invention, the compound is enantiomerically and diasteriomerically pure. In another embodiment, the compound is enantiomerically or diasteriomerically pure. In one embodiment, the compound is a (+) enantiomer. In one embodiment, the compound is a (−) enantiomer.

Illustrative of the invention is a pharmaceutical composition comprising a pharmaceutically acceptable carrier and a therapeutically effective amount of any one the compounds of the invention.

An illustration of the invention is a pharmaceutical composition made by admixing any one of the compounds described above and a pharmaceutically acceptable carrier.

Illustrative of the invention is a process for making a pharmaceutical composition comprising admixing any of the compounds of the invention and a pharmaceutically acceptable carrier.

Illustrative of the invention is a synthetic process for making any of the compounds of the invention.

Exemplifying the invention is a method of treating a disorder mediated by the MCH1 receptor in a subject in need thereof comprising administering to the subject a therapeutically effective amount of any one of the compounds or pharmaceutical compositions of the invention and a pharmaceutically acceptable carrier.

In one embodiment, the therapeutically effective amount is between about 0.03 and about 300 mg.

In one embodiment, the disorder is depression. In one embodiment, the disorder is anxiety. In one embodiment, the disorder is obesity. In one embodiment, the disorder is urge incontinence.

One embodiment is a method of treating a subject suffering from a disorder selected from depression, anxiety, obesity or urge incontinence in a subject in need thereof, comprising administering to a subject a therapeutically effective amount of a compound of the invention.

In one embodiment, the therapeutically effective amount is between about 0.03 and about 300 mg.

In another embodiment, the disorder is depression. In one embodiment, the disorder is anxiety. In one embodiment, the disorder is obesity. In one embodiment, the disorder is urge incontinence.

DETAILED DESCRIPTION OF THE INVENTION

This invention provides a compound having the structure:

wherein each A is independently —H, —F, —Cl, —Br, —I, —CN, —$NO_2$, —$OR_3$ or straight chained or branched $C_1$-$C_7$ alkyl;

wherein each B is independently N or CH;

wherein Z is CO or $SO_2$;

wherein each R is independently —H, —F or straight chained or branched $C_1$-$C_7$ alkyl, monofluoroalkyl or polyfluoroalkyl;

wherein $R_4$ is independently —$OR_3$, —$NHR_3$, —$SR_3$, —$COR_3$, straight chained or branched $C_1$-$C_7$ alkyl, monofluoroalkyl or polyfluoroalkyl, aryl or heteroaryl, wherein the aryl or heteroaryl is optionally substituted with one or more —F, —Cl, —Br, —I, —$OR_2$, or straight chained or branched $C_1$-$C_7$ alkyl;

wherein each $R_3$ is independently —H; straight chained or branched $C_1$-$C_7$ alkyl, monofluoroalkyl or polyfluoroalkyl; aryl or heteroaryl, wherein the aryl or heteroaryl is optionally substituted with one or more —F, —Cl, —Br, —I, —$NO_2$, —CN, —$OR_2$, or —$NHR_2$;

wherein each $R_2$ is independently —H, straight chained or branched $C_1$-$C_7$ alkyl, aryl or heteroaryl, wherein the aryl or heteroaryl is optionally substituted with one or more —F, —Cl, —Br, —I, —$NO_2$, —CN; and wherein n is an integer from 1 to 6 inclusive;

or a pharmaceutically acceptable salt thereof.

In one embodiment, the compound has the structure:

In one embodiment the compound has the structure:

wherein $R_4$ is aryl or heteroaryl, wherein the aryl or heteroaryl is optionally substituted with one or more —F, —Cl, —Br, —I, —$OR_3$, or straight chained or branched $C_1$-$C_7$ alkyl;

wherein each $R_3$ is straight chained or branched $C_1$-$C_7$ alkyl, aryl or heteroaryl, wherein the aryl or heteroaryl is optionally substituted with one or more —F, —Cl, —Br, —I, —$NO_2$, —CN, or —$OR_2$; and wherein each $R_2$ is —H, straight chained or branched $C_1$-$C_7$ alkyl, aryl or heteroaryl, wherein the aryl or heteroaryl is optionally substituted with one or more —F, —Cl, —Br, —I, —$NO_2$, —CN.

In one embodiment of the invention is the compound having the structure:

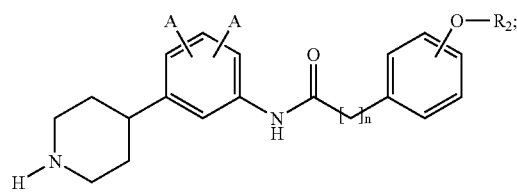

wherein $R_2$ is —H, straight chained or branched $C_1$-$C_7$ alkyl, or aryl wherein the aryl is optionally substituted with one or more —F, —Cl, —Br, —I, —$NO_2$, or —CN.

In one embodiment the compound has the structure:

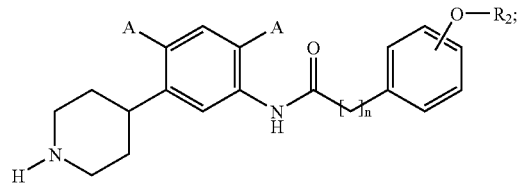

wherein $R_2$ is straight chained or branched $C_1$-$C_7$ alkyl; and wherein n is an integer from 3-6 inclusive.

The compound of the invention wherein the compound has the structure:

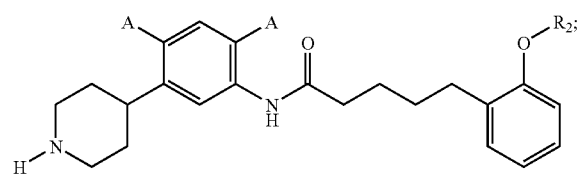

wherein each A is independently —H, —F, —Cl, —Br or —I.

In one embodiment, the compound has the structure:

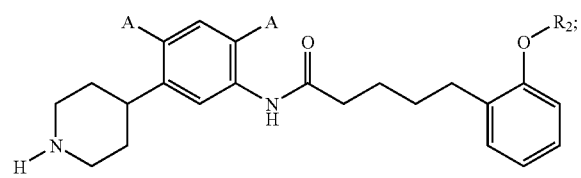

wherein each A is independently —H, —F or —Cl; and wherein $R_2$ is straight chained or branched $C_1$-$C_3$ alkyl.

The compound having the structure:

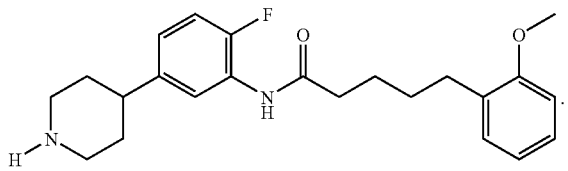

The compound having the structure:

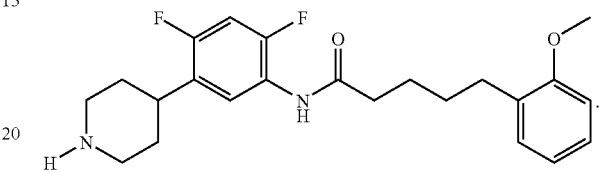

In one embodiment the compound has the structure:

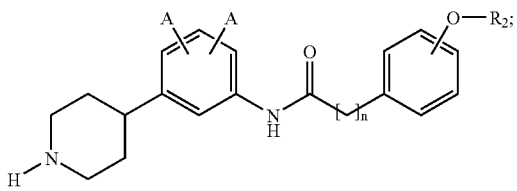

wherein $R_2$ is aryl, wherein the aryl is optionally substituted with one or more —F, —Cl, —Br, —I, —$NO_2$, or —CN; and wherein n is an integer from 1 to 6 inclusive;

In one embodiment the compound has the structure:

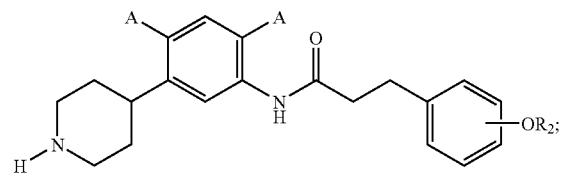

wherein each A is independently —H, —F, —Cl, —Br or —I.

In one embodiment the compound has the structure:

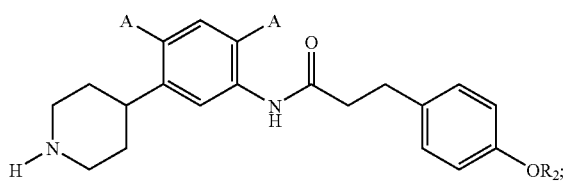

wherein each A is independently —H, —F or —Cl; and wherein $R_2$ is aryl optionally substituted with one or more —F, —Cl, or —Br.

In one embodiment the compound has the structure:

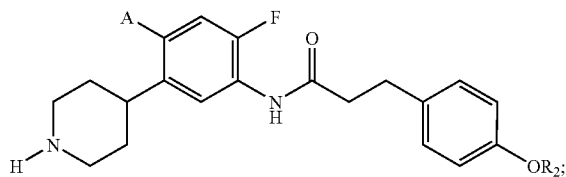

wherein each A is independently —H, —F or —Cl; and
wherein R$_2$ is aryl optionally substituted with one or more —F.

In one embodiment the compound has the structure:

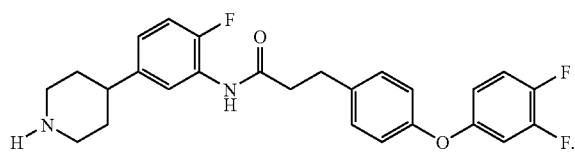

In one embodiment the compound has the structure:

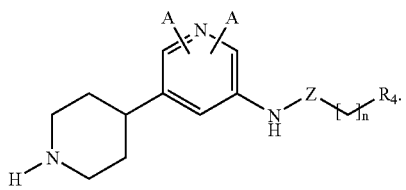

In one embodiment the compound has the structure:

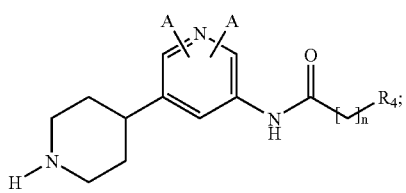

wherein R$_4$ is aryl optionally substituted with one or more —F, —Cl, —Br, —I, —OR$_3$, or straight chained or branched C$_1$-C$_7$ alkyl;
wherein each R$_3$ is independently straight chained or branched C$_1$-C$_7$ alkyl, aryl or heteroaryl, wherein the aryl or heteroaryl is optionally substituted with one or more —F, —Cl, —Br, —I, —NO$_2$, —CN, or —OR$_2$;
wherein each R$_2$ is independently straight chained or branched C$_1$-C$_7$ alkyl.

This invention further provides a compound having the structure:

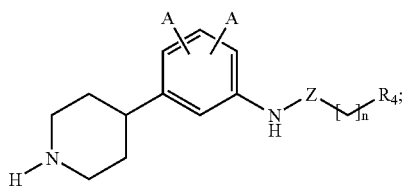

wherein R$_4$ is independently —OR$_3$, —NHR$_3$, —COR$_3$ or —SR$_3$;
wherein each R$_3$ is independently straight chained or branched C$_1$-C$_7$ alkyl, aryl or heteroaryl, wherein the aryl or heteroaryl is optionally substituted with one or more —F, —Cl, —Br, —I, —NO$_2$, —CN, —OR$_2$, or —NHR$_2$;
wherein R$_2$ is —H, straight chained or branched C$_1$-C$_7$ alkyl, or aryl wherein the aryl is optionally substituted with one or more —F, —Cl, —Br, —I, —NO$_2$, —CN; and
wherein n is an integer from 1 to 6 inclusive;

In one embodiment the compound has the structure:

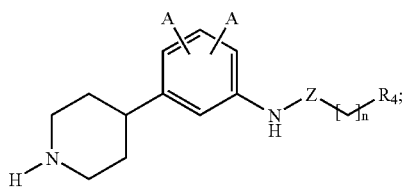

wherein each A is independently —H, —F, —Cl, —Br or —I;
wherein R$_4$ is independently —OR$_3$, —NHR$_3$, or —COR$_3$;
wherein R$_3$ is aryl optionally substituted with one or more —F, —Cl, —Br, —I, —NO$_2$, —CN, —OR$_2$ or —NHR$_2$;
wherein each R$_2$ is independently —H, straight chained or branched C$_1$-C$_7$ alkyl or aryl optionally substituted with one or more —F, —Cl, —Br, —I, —NO$_2$, —CN; and
wherein n is an integer from 1 to 6 inclusive.

In one embodiment the compound has the structure:

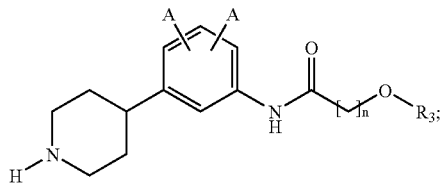

wherein each A is independently —H or —F;
wherein R$_3$ is aryl optionally substituted with one or more —F, —Cl, —Br, —I, —NO$_2$, —CN, —OR$_2$ or —NHR$_2$;
wherein R$_2$ is independently straight chained or branched C$_1$-C$_7$ alkyl or aryl optionally substituted with one or more —F, —Cl, —Br or —I; and
wherein n is an integer from 1 to 6 inclusive.

In one embodiment of the invention, the compound has the structure:

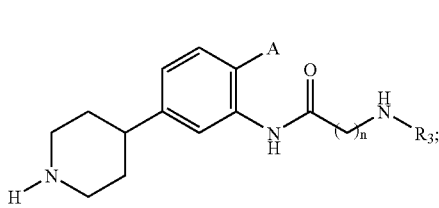

wherein A is —H, —F, —Cl, —Br or —I;
wherein aryl optionally substituted with one or more —F, —Cl, —Br, —I;

The compound having the structure:

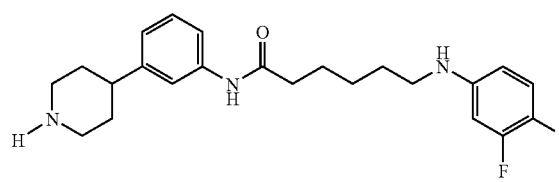

In one embodiment the compound has the structure:

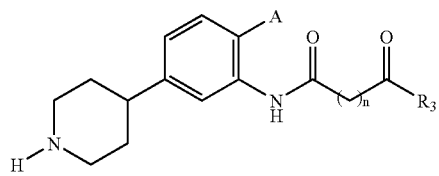

In one embodiment the compound has the structure:

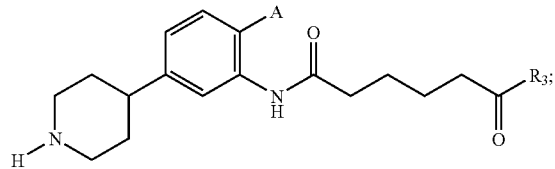

wherein A is —H, —F, —Cl, —Br or —I;
wherein $R_3$ is aryl optionally substituted with one or more —F, —Cl, —Br or —I.

The compound having the structure:

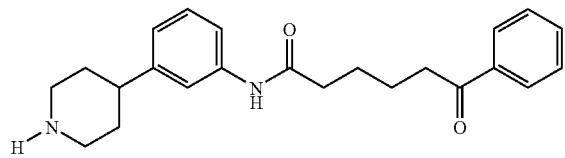

The compound having the structure:

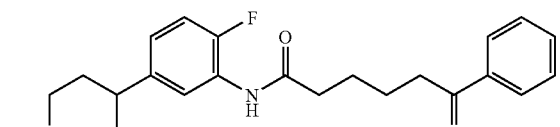

This invention also provides a compound having the structure:

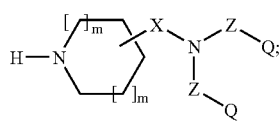

wherein each Q independently is hydrogen;

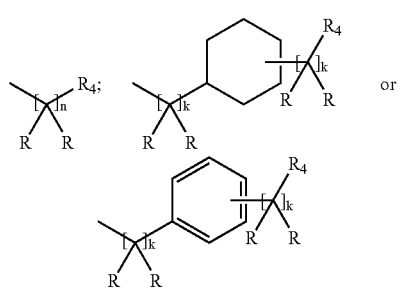

wherein X is aryl or heteroaryl, wherein the aryl or heteroaryl is optionally substituted with one or more —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —CN, —$NO_2$, —$SR_3$, —$(CH_2)_qOR_3$, —$(CH_2)_qSR_3$, aryl, phenoxy or heteroaryl, straight chained or branched $C_1$-$C_7$ alkyl, monofluoroalkyl or polyfluoroalkyl, straight chained or branched $C_2$-$C_7$ alkenyl or alkynyl or $C_3$-$C_7$ cycloalkyl, monofluorocycloalkyl, polyfluorocycloalkyl or cycloalkenyl;
wherein each Z is independently CO; CS; $SO_2$; or null;
wherein each R is independently —H; —F; straight chained or branched $C_1$-$C_7$ alkyl, monofluoroalkyl or polyfluoroalkyl; straight chained or branched $C_2$-$C_7$ alkenyl or alkynyl; —$N(R_3)_2$; —$NO_2$; —CN; —$CO_2R_3$; —$OCOR_3$; —$OR_3$; —$N(R_3)COR_3$ or —$CON(R_3)_2$;
wherein each $R_2$ is independently —H, straight chained or branched $C_1$-$C_7$ alkyl, aryl or heteroaryl, wherein the aryl or heteroaryl is optionally substituted with one or more —F, —Cl, —Br, —I, —$NO_2$, —CN, straight chained or branched $C_1$-$C_7$ alkyl, monofluoroalkyl or polyfluoroalkyl, or straight chained or branched $C_2$-$C_7$ alkenyl or alkynyl;
wherein each $R_3$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, monofluorocycloalkyl, polyfluorocycloalkyl or cycloalkenyl; aryl or heteroaryl, wherein the aryl or heteroaryl is optionally substituted with one or more —F, —Cl, —Br, —I, —$N(R_2)_2$, —$NO_2$, —CN, —$COR_2$ —$CO_2R_2$, —$OCOR_2$, —$OR_2$, —$N(R_2)COR_2$—$N(R_2)CON(R_2)_2$, —$CON(R_2)_2$, aryl, heteroaryl, phenoxy, straight chained or branched $C_1$-$C_7$ alkyl, monofluoroalkyl or polyfluoroalkyl, straight chained or branched $C_2$-$C_7$ alkenyl or alkynyl, $C_3$-$C_7$ cycloalkyl, monofluorocycloalkyl, polyfluorocycloalkyl or cycloalkenyl;

wherein each $R_4$ is independently —H; -$ZR_3$, -$ZOR_3$, —$OZR_3$, -$ZN(R_3)_2$, —$N(R_3)ZR_3$, —$N(R_3)ZN(R_3)_2$, straight chained or branched $C_1$-$C_7$ alkyl, monofluoroalkyl or polyfluoroalkyl, aryl, benzyl or heteroaryl, wherein the aryl, benzyl or heteroaryl is optionally substituted with one or more —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —CN, —$NO_2$, —$SR_3$, —$(CH_2)_qOR_3$, —$(CH_2)_qSR_3$, aryl, benzyl, heteroaryl, straight chained or branched $C_1$-$C_7$ alkyl, monofluoroalkyl or polyfluoroalkyl, straight chained or branched $C_2$-$C_7$ alkenyl or alkynyl or $C_3$-$C_7$ cycloalkyl, monofluorocycloalkyl, polyfluorocycloalkyl, or cycloalkenyl;

wherein each k is independently an integer from 1 to 3 inclusive;

where in each m is independently an integer from 0 to 1 inclusive;

wherein n is an integer from 0 to 6 inclusive;

wherein q is an integer from 1 to 3 inclusive;

or a pharmaceutically acceptable salt thereof.

This invention also provides a compound having the structure:

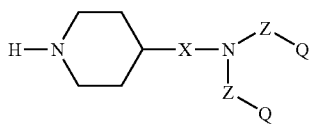

wherein each Q is independently hydrogen;

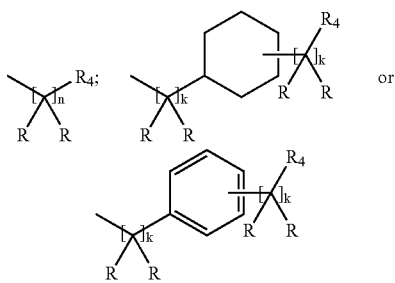

wherein X is aryl or heteroaryl, wherein the aryl or heteroaryl is optionally substituted with one or more —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —CN, —$NO_2$, —$SR_3$, —$(CH_2)_qOR_3$, —$(CH_2)_qSR_3$, aryl, phenoxy or heteroaryl, straight chained or branched $C_1$-$C_7$ alkyl, monofluoroalkyl or polyfluoroalkyl, straight chained or branched $C_2$-$C_7$ alkenyl or alkynyl or $C_3$-$C_7$ cycloalkyl, monofluorocycloalkyl, polyfluorocycloalkyl or cycloalkenyl;

wherein each Z is independently CO; CS; $SO_2$; or null;

wherein each R is independently —H; —F; straight chained or branched $C_1$-$C_7$ alkyl, monofluoroalkyl or polyfluoroalkyl; straight chained or branched $C_2$-$C_7$ alkenyl or alkynyl; —$N(R_3)_2$; —$NO_2$; —CN; —$CO_2R_3$; —$OCOR_3$; —$OR_3$; —$N(R_3)COR_3$ or —$CON(R_3)_2$;

wherein each $R_2$ is independently —H, straight chained or branched $C_1$-$C_7$ alkyl, aryl or heteroaryl, wherein the aryl or heteroaryl is optionally substituted with one or more —F, —Cl, —Br, —I, —$NO_2$, —CN, straight chained or branched $C_1$-$C_7$ alkyl, monofluoroalkyl or polyfluoroalkyl, or straight chained or branched $C_2$-$C_7$ alkenyl or alkynyl;

wherein each $R_3$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, monofluorocycloalkyl, polyfluorocycloalkyl or cycloalkenyl; aryl or heteroaryl, wherein the aryl or heteroaryl is optionally substituted with one or more —F, —Cl, —Br, —I, —$N(R_2)_2$, —$NO_2$, —CN, —$COR_2$ —$CO_2R_2$, —$OCOR_2$, —$OR_2$, —$N(R_2)COR_2$ —$N(R_2)CON(R_2)_2$, —$CON(R_2)_2$, aryl, heteroaryl, phenoxy, straight chained or branched $C_1$-$C_7$ alkyl, monofluoroalkyl or polyfluoroalkyl, straight chained or branched $C_2$-$C_7$ alkenyl or alkynyl, $C_3$-$C_7$ cycloalkyl, monofluorocycloalkyl, polyfluorocycloalkyl or cycloalkenyl;

wherein each $R_4$ is independently —H; -$ZR_3$, -$ZOR_3$, —$OZR_3$, -$ZN(R_3)_2$, —$N(R_3)ZR_3$, —$N(R_3)ZN(R_3)_2$, straight chained or branched $C_1$-$C_7$ alkyl, monofluoroalkyl or polyfluoroalkyl, aryl, benzyl or heteroaryl, wherein the aryl, benzyl or heteroaryl is optionally substituted with one or more —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —CN, —$NO_2$, —$SR_3$, —$(CH_2)_qOR_3$, —$(CH_2)_qSR_3$, aryl, benzyl, heteroaryl, straight chained or branched $C_1$-$C_7$ alkyl, monofluoroalkyl or polyfluoroalkyl, straight chained or branched $C_2$-$C_7$ alkenyl or alkynyl or $C_3$-$C_7$ cycloalkyl, monofluorocycloalkyl, polyfluorocycloalkyl, or cycloalkenyl;

wherein each k is independently an integer from 1 to 3 inclusive;

wherein n is an integer from 0 to 6 inclusive;

wherein q is an integer from 1 to 3 inclusive;

or a pharmaceutically acceptable salt thereof.

Illustrative of the invention is a pharmaceutical composition comprising a pharmaceutically acceptable carrier and a pharmaceutically therapeutically effective amount of any one the compounds described above.

An illustration of the invention is a pharmaceutical composition made by admixing any one of the compounds described above and a pharmaceutically acceptable carrier.

Illustrative of the invention is a process for making a pharmaceutical composition comprising admixing any of the compounds described above and a pharmaceutically acceptable carrier.

Illustrative of the invention is a synthetic process for making any of the compounds described above.

Exemplifying the invention is a method of treating a condition mediated by the MCH1 receptor in a subject in need thereof comprising administering to the subject a therapeutically effective amount of any one of the compounds or pharmaceutical compositions described above and a pharmaceutically acceptable carrier.

This invention also provides a compound having the structure:

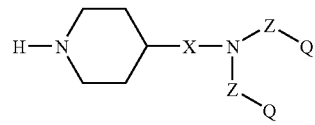

wherein each Q is independently hydrogen;

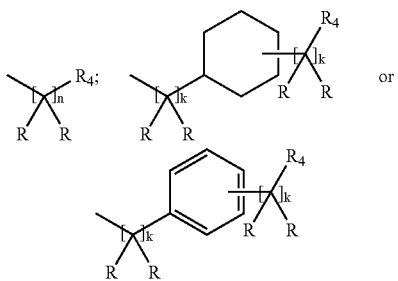

wherein X is phenyl or a nitrogen containing hetercycle, wherein the phenyl or a nitrogen containing hetercycle is optionally substituted with one or more —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —CN, —$NO_2$, —$SR_3$, —$(CH_2)_qOR_3$, —$(CH_2)_qSR_3$, aryl, phenoxy or heteroaryl, straight chained or branched $C_1$-$C_7$ alkyl, monofluoroalkyl or polyfluoroalkyl, straight chained or branched $C_2$-$C_7$ alkenyl or alkynyl or $C_3$-$C_7$ cycloalkyl, monofluorocycloalkyl, polyfluorocycloalkyl or cycloalkenyl;

wherein each Z is independently CO; CS; $SO_2$; or null;

wherein each R is independently —H; —F; straight chained or branched $C_1$-$C_7$ alkyl, monofluoroalkyl or polyfluoroalkyl; straight chained or branched $C_2$-$C_7$ alkenyl or alkynyl; —$N(R_3)_2$; —$NO_2$; —CN; —$CO_2R_3$; —$OCOR_3$; —$OR_3$; —$N(R_3)COR_3$ or —$CON(R_3)_2$;

wherein each $R_2$ is independently —H, straight chained or branched $C_1$-$C_7$ alkyl, aryl or heteroaryl, wherein the aryl or heteroaryl is optionally substituted with one or more —F, —Cl, —Br, —I, —$NO_2$, —CN, straight chained or branched $C_1$-$C_7$ alkyl, monofluoroalkyl or polyfluoroalkyl, or straight chained or branched $C_2$-$C_7$ alkenyl or alkynyl;

wherein each $R_3$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, monofluorocycloalkyl, polyfluorocycloalkyl or cycloalkenyl; aryl or heteroaryl, wherein the aryl or heteroaryl is optionally substituted with one or more —F, —Cl, —Br, —I, —$N(R_2)_2$, —$NO_2$, —CN, —$COR_2$—$CO_2R_2$, —$OCOR_2$, —$OR_2$, —$N(R_2)COR_2$ —$N(R_2)CON(R_2)_2$, —$CON(R_2)_2$, aryl, heteroaryl, phenoxy, straight chained or branched $C_1$-$C_7$ alkyl, monofluoroalkyl or polyfluoroalkyl, straight chained or branched $C_2$-$C_7$ alkenyl or alkynyl, $C_3$-$C_7$ cycloalkyl, monofluorocycloalkyl, polyfluorocycloalkyl or cycloalkenyl;

wherein each $R_4$ is independently —H; -$ZR_3$, -$ZOR_3$, —$OZR_3$, -$ZN(R_3)_2$, —$N(R_3)ZR_3$, —$N(R_3)ZN(R_3)_2$, straight chained or branched $C_1$-$C_7$ alkyl, monofluoroalkyl or polyfluoroalkyl, aryl, benzyl or heteroaryl, wherein the aryl, benzyl or heteroaryl is optionally substituted with one or more —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —CN, —$NO_2$, —$SR_3$, —$(CH_2)_qOR_3$, —$(CH_2)_qSR_3$, aryl, benzyl, heteroaryl, straight chained or branched $C_1$-$C_7$ alkyl, monofluoroalkyl or polyfluoroalkyl, straight chained or branched $C_2$-$C_7$ alkenyl or alkynyl or $C_3$-$C_7$ cycloalkyl, monofluorocycloalkyl, polyfluorocycloalkyl, or cycloalkenyl;

wherein each k is independently an integer from 1 to 3 inclusive;

wherein n is an integer from 0 to 6 inclusive;

wherein q is an integer from 1 to 3 inclusive;

or a pharmaceutically acceptable salt thereof.

This invention provides a compound having the structure:

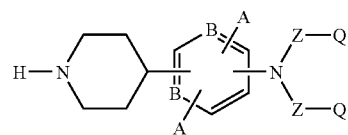

wherein each Q is independently hydrogen;

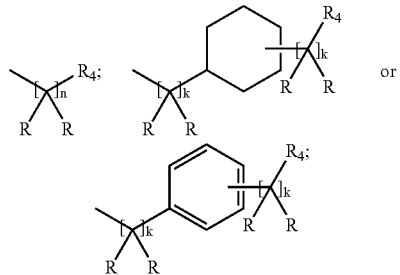

wherein each A is independently —H, —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —CN, —$NO_2$, —$N(R_3)_2$, —$OR_3$, —$SR_3$, —$(CH_2)_qOR_3$, —$(CH_2)_qSR3$, straight chained or branched $C_1$-$C_7$ alkyl, monofluoroalkyl or polyfluoroalkyl, straight chained or branched $C_2$-$C_7$ alkenyl or alkynyl, $C_3$-$C_7$ cycloalkyl, monofluorocycloalkyl, polyfluorocycloalkyl, or cycloalkenyl;

wherein each B is independently N or CH;

wherein each Z is independently CO; CS; $SO_2$ or null;

wherein each R is independently —H, —F, straight chained or branched $C_1$-$C_7$ alkyl, monofluoroalkyl or polyfluoroalkyl, straight chained or branched $C_2$-$C_7$ alkenyl or alkynyl, —$N(R_3)_2$, —$NO_2$, —CN, —$CO_2R_3$, —$OCOR_3$, —$OR_3$, —$N(R_3)COR_3$ or —$CON(R_3)_2$;

wherein each $R_2$ is independently —H, straight chained or branched $C_1$-$C_7$ alkyl, aryl or heteroaryl, wherein the aryl or heteroaryl is optionally substituted with one or more —F, —Cl, —Br, —I, —$NO_2$, —CN, straight chained or branched $C_1$-$C_7$ alkyl, monofluoroalkyl or polyfluoroalkyl, or straight chained or branched $C_2$-$C_7$ alkenyl or alkynyl;

wherein each $R_3$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, monofluorocycloalkyl, polyfluorocycloalkyl or cycloalkenyl; aryl or heteroaryl, wherein the aryl or heteroaryl is optionally substituted with one or more —F, —Cl, —Br, —I, —$N(R_2)_2$, —$NO_2$, —CN, —$COR_2$—$CO_2R_2$, —$OCOR_2$, —$OR_2$, —$N(R_2)COR_2$ —$N(R_2)CON(R_2)_2$, —$CON(R_2)_2$, aryl, heteroaryl, phenoxy, straight chained or branched $C_1$-$C_7$ alkyl, monofluoroalkyl or polyfluoroalkyl, straight chained or branched $C_2$-$C_7$ alkenyl or alkynyl, $C_3$-$C_7$ cycloalkyl, monofluorocycloalkyl, polyfluorocycloalkyl or cycloalkenyl;

wherein each $R_4$ is independently —H; -$ZR_3$, -$ZOR_3$, —$OZR_3$, -$ZN(R_3)_2$, —$N(R_3)ZR_3$, —$N(R_3)ZN(R_3)_2$, straight chained or branched $C_1$-$C_7$ alkyl, monofluoroalkyl or polyfluoroalkyl, aryl, benzyl or heteroaryl, wherein the aryl, benzyl or heteroaryl is optionally substituted with one or more —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —CN, —$NO_2$, —$SR_3$, —$(CH_2)_qOR_3$, —$(CH_2)_qSR_3$, aryl, benzyl, heteroaryl, straight chained or branched $C_1$-$C_7$ alkyl, monofluoroalkyl or polyfluoroalkyl, straight chained or branched $C_2$-$C_7$ alkenyl or alkynyl or $C_3$-$C_7$ cycloalkyl, monofluorocycloalkyl, polyfluorocycloalkyl, or cycloalkenyl;

wherein each k is independently an integer from 1 to 3 inclusive;

wherein n is an integer from 0 to 6 inclusive;

wherein q is an integer from 1 to 3 inclusive;

or a pharmaceutically acceptable salt thereof.

In one embodiment, each A is independently —H, —F, —Cl, —Br, —I, -$ZR_3$, -$ZOR_3$, —$OZR_3$, -$ZN(R_3)_2$, —$N(R_3)ZR_3$, —$N(R_3)ZN(R_3)_2$, —$N(R_3)_2$, —$OR_3$, —$SR_3$, —$(CH_2)_qOR_3$, —$(CH_2)_qSR_3$, straight chained or branched $C_1$-$C_7$ alkyl, monofluoroalkyl or polyfluoroalkyl;

wherein each Z is independently CO; CS or null;

wherein each R is independently —H, —F or straight chained or branched $C_1$-$C_7$ alkyl;

wherein each $R_2$ is independently —H, straight chained or branched $C_1$-$C_7$ alkyl, aryl or heteroaryl, wherein the aryl or heteroaryl is optionally substituted with one or more —F, —Cl, —Br, —I, —$NO_2$, —CN, straight chained or branched $C_1$-$C_7$ alkyl, monofluoroalkyl or polyfluoroalkyl, or straight chained or branched $C_2$-$C_7$ alkenyl or alkynyl;

wherein each $R_3$ is independently —H, straight chained or branched $C_1$-$C_7$ alkyl, aryl or heteroaryl, wherein the aryl or heteroaryl is optionally substituted with one or more —F, —Cl, —Br, —I, —$N(R_2)_2$, —$NO_2$, —CN, —$COR_2$—$CO_2R_2$, —$OCOR_2$, —$OR_2$, —$N(R_2)COR_2$ —$N(R_2)CON(R_2)_2$, —$CON(R_2)_2$, aryl, heteroaryl, phenoxy, straight chained or branched $C_1$-$C_7$ alkyl, monofluoroalkyl or polyfluoroalkyl, straight chained or branched $C_2$-$C_7$ alkenyl or alkynyl, $C_3$-$C_7$ cycloalkyl, monofluorocycloalkyl, polyfluorocycloalkyl or cycloalkenyl;

In one embodiment, the compound has the structure:

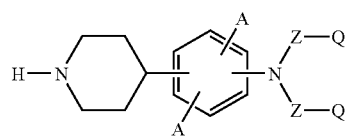

In one embodiment, the compound has the structure:

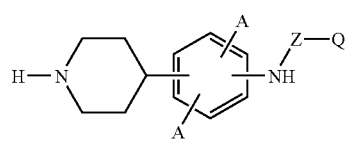

In one embodiment, the compound has the structure:

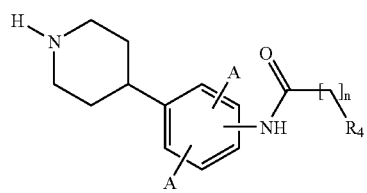

In one embodiment, the compound has the structure:

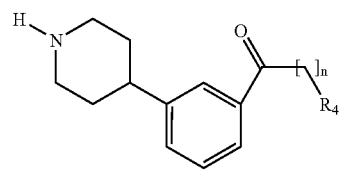

wherein $R_4$ is aryl, wherein the aryl is optionally substituted with one or more —F, —Cl, —Br, —I, straight chained or branched $C_1$-$C_7$ alkyl, monofluoroalkyl or polyfluoroalkyl, straight chained or branched $C_2$-$C_7$ alkenyl or alkynyl or $C_3$-$C_7$ cycloalkyl, monofluorocycloalkyl, polyfluorocycloalkyl, or cycloalkenyl.

In one embodiment, the compound has the structure:

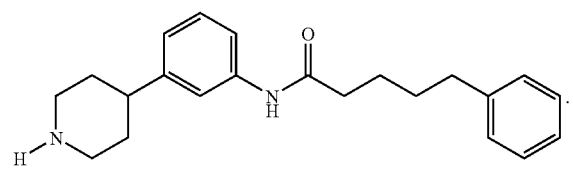

In one embodiment, the compound has the structure:

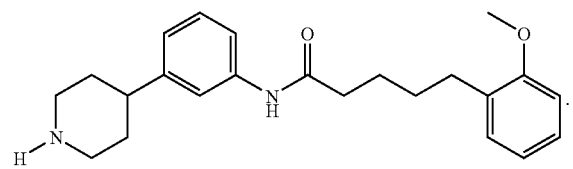

In one embodiment, the compound has the structure:

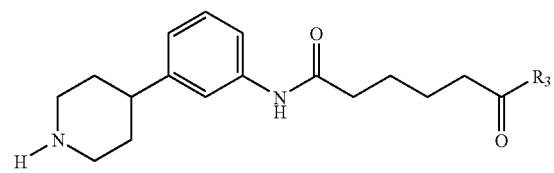

wherein $R_3$ is aryl or heteroaryl, wherein the aryl or heteroaryl is optionally substituted with one or more —F, —Cl, —Br, —I, —$N(R_2)_2$, —$NO_2$, —CN, —$COR_2$ —$CO_2R_2$, —$OCOR_2$, —$OR_2$, —$N(R_2)COR_2$ —$N(R_2)CON(R_2)_2$, —$CON(R_2)_2$, aryl, heteroaryl, phenoxy, straight chained or branched $C_1$-$C_7$ alkyl.

In one embodiment, the compound has the structure:

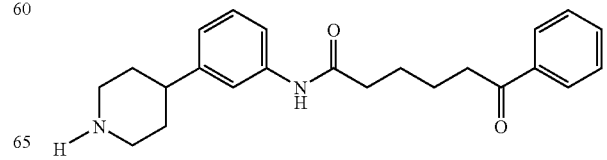

In one embodiment, the compound has the structure:

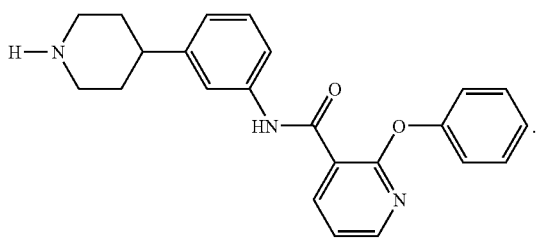

As used in the above-described inventions, the term "heteroaryl" is used to include five and six membered unsaturated rings that may contain one or more oxygen, sulfur, or nitrogen atoms. Examples of heteroaryl groups include, but are not limited to, carbazole, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition, the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, CN, —NO$_2$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl; $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, The term "heteroaryl" further includes the N-oxides of those chemical moieties recited above which include at least one nitrogen atom. In the present invention, the term "aryl" is phenyl or naphthyl.

In a further embodiment of the aforementioned invention, the compound is enantiomerically and diasteriomerically pure. In another embodiment, the compound is enantiomerically or diasteriomerically pure.

In one embodiment, the compound is a (+) enantiomer. In one embodiment, the compound is a (−) enantiomer.

The invention provides for each pure stereoisomer of any of the compounds described herein. Such stereoisomers may include enantiomers, diastereomers, or E or Z alkene or imine isomers. The invention also provides for stereoisomeric mixtures, including racemic mixtures, diastereomeric mixtures, or E/Z isomeric mixtures. Stereoisomers can be synthesized in pure form (Nógrádi, M.; *Stereoselective Synthesis*, (1987) VCH Editor Ebel, H. and *Asymmetric Synthesis*, Volumes 3 B 5, (1983) Academic Press, Editor Morrison, J.) or they can be resolved by a variety of methods such as crystallization and chromatographic techniques (Jaques, J.; Collet, A.; Wilen, S.; *Enantiomer, Racemates, and Resolutions,* 1981, John Wiley and Sons and *Asymmetric Synthesis*, Vol. 2, 1983, Academic Press, Editor Morrison, J).

In addition the compounds of the present invention may be present as enantiomers, diasteriomers, isomers or two or more of the compounds may be present to form a racemic or diastereomeric mixture.

The compounds of the present invention are preferably 80% pure, more preferably 90% pure, and most preferably 95% pure. Included in this invention are pharmaceutically acceptable salts and complexes of all of the compounds described herein. The acids and bases from which these salts are prepared include but are not limited to the acids and bases listed herein. The acids include, but are not limited to, the following inorganic acids: hydrochloric acid, hydrobromic acid, hydroiodic acid, sulfuric acid and boric acid. The acids include, but are not limited to, the following organic acids: acetic acid, malonic acid, succinic acid, fumaric acid, tartaric acid, maleic acid, citric acid, methanesulfonic acid, benzoic acid, glycolic acid, lactic acid and mandelic acid. The bases include, but are not limited to ammonia, methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound. Thus, in the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

Illustrative of the invention is a pharmaceutical composition comprising a pharmaceutically acceptable carrier and a therapeutically effective amount of any one the compounds of the invention.

An illustration of the invention is a pharmaceutical composition made by admixing any one of the compounds described above and a pharmaceutically acceptable carrier.

Illustrative of the invention is a process for making a pharmaceutical composition comprising admixing any of the compounds of the invention and a pharmaceutically acceptable carrier.

A solid carrier can include one or more substances which may also act as endogenous carriers (e.g. nutrient or micronutrient carriers), flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, coloring agents, viscosity regulators, stabilizers or osmoregulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate or isopropyl myristate. Sterile liquid carriers are useful in sterile liquid form compositions for parenteral administration. The liquid carrier for pressurized compositions can be a halogenated hydrocarbon or other pharmaceutically acceptable propellant.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings. The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspenions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

Illustrative of the invention is a synthetic process for making any of the compounds of the invention.

Exemplifying the invention is a method of treating a disorder mediated by the MCH1 receptor in a subject in need thereof comprising administering to the subject a therapeutically effective amount of any one of the compounds or pharmaceutical compositions of the invention and a pharmaceutically acceptable carrier.

In one embodiment, the therapeutically effective amount is between about 0.03 and about 300 mg.

In one embodiment, the disorder is depression. In one embodiment, the disorder is anxiety. In one embodiment, the disorder is obesity. In one embodiment, the disorder is urge incontinence.

One embodiment is a method of treating a subject suffering from a disorder selected from depression, anxiety, obesity or urge incontinence in a subject in need thereof, comprising administering to a subject a therapeutically effective amount of a compound of the invention.

In one embodiment, the therapeutically effective amount is between about 0.03 and about 300 mg.

In another embodiment, the disorder is depression. In one embodiment, the disorder is anxiety. In one embodiment, the disorder is obesity. In one embodiment, the disorder is urge incontinence.

In the subject application a "therapeutically effective amount" is any amount of a compound which, when administered to a subject suffering from a disease against which the compounds are effective, causes reduction, remission, or regression of the disease. In a subject application, a "subject" is a vertebrate, a mammal or a human.

This invention provides a method of treating a subject suffering from an abnormality wherein the abnormality is alleviated by decreasing the activity of an MCH1 receptor which comprises administering to the subject an amount of a compound of the invention which is an MCH1 receptor antagonist effective to treat the subject's abnormality.

In separate embodiments, the abnormality is a regulation of a steroid or pituitary hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder such as Alzheimer's disease, a sensory modulation and transmission disorder, a motor coordination disorder, a sensory integration disorder, a motor integration disorder, a dopaminergic function disorder such as Parkinson=s disease, a sensory transmission disorder, an olfaction disorder, a sympathetic innervation disorder, an affective disorder such as depression and anxiety, a stress-related disorder, a fluid-balance disorder, a seizure disorder, pain, psychotic behavior such as schizophrenia, morphine tolerance, opiate addiction, migraine or a urinary disorder such as urinary incontinence.

In a preferred embodiment, the subject invention provides a method of treatment for the following indications: depression, anxiety, eating/body weight disorders, and urinary disorders. Examples of eating/body weight disorders are obesity, bulimia, or bulimia nervosa. Examples of urinary disorders include, but are not limited to, urinary incontinence, overactive bladder, urge incontinence, urinary frequency, urinary urgency, nocturia, or enuresis. Overactive bladder and urinary urgency may or may not be associated with benign prostatic hyperplasia.

This invention provides a method of modifying the feeding behavior of a subject which comprises administering to the subject an amount of a compound of the invention effective to decrease the consumption of food by the subject.

This invention also provides a method of treating an eating disorder in a subject which comprises administering to the subject an amount of a compound of this invention effective to decrease the consumption of food by the subject. In an embodiment of the present invention, the eating disorder is bulimia, obesity or bulimia nervosa. In an embodiment of the present invention, the subject is a vertebrate, a mammal, a human or a canine. In a further embodiment, the compound is administered in combination with food.

The present invention further provides a method of reducing the body mass of a subject which comprises administering to the subject an amount of a compound of the invention effective to reduce the body mass of the subject.

The present invention also provides a method of treating a subject suffering from depression which comprises administering to the subject an amount of a compound of this invention effective to treat the subject's depression. The present invention further provides a method of treating a subject suffering from anxiety which comprises administering to the subject an amount of a compound of this invention effective to treat the subject's anxiety. The present invention also provides a method of treating a subject suffering from depression and anxiety which comprises administering to the subject an amount of a compound of this invention effective to treat the subject=s depression and anxiety.

The present invention also provides a method of treating a subject suffering from major depressive disorder, dysthymic disorder, bipolar I and II disorders, schizoaffective disorder, cognitive disorders with depressed mood, personality disorders, insomnia, hypersomnia, narcolepsy, circadian rhythm sleep disorder, nightmare disorder, sleep terror disorder, sleepwalking disorder, obsessive-compulsive disorder, panic disorder, with or without agoraphobia, posttraumatic stress disorder, social anxiety disorder, social phobia and generalized anxiety disorder.

The present invention also provides a method of treating a subject suffering from a urinary disorder which comprises administering to the subject an amount of a compound of this invention effective to treat the subject's a urinary disorder. In some embodiments, the urinary disorder is urinary incontinence, overactive bladder, urge incontinence, urinary frequency, urinary urgency, nocturia, or enuresis.

This invention will be better understood from the Experimental Details which follow. However, one skilled in the art will readily appreciate that the specific methods and results discussed are merely illustrative of the invention as described more fully in the claims which follow thereafter.

EXPERIMENTAL SECTION

I. Synthesis of Chemical Compounds

General Methods: All reactions were performed under an Argon atmosphere and the reagents, neat or in appropriate solvents, were transferred to the reaction vessel via syringe and cannula techniques. The parallel synthesis reaction arrays were performed in vials (without an inert atmosphere) using J-KEM heating shakers (Saint Louis, Mo.). Anhydrous solvents were purchased from Aldrich Chemical Company (Milwaukee, Wis.) and used as received.

Unless otherwise noted, the $^1H$ spectra were recorded at 400 MHz (Brüker, Model: Avance) with tetramethylsilane as internal standard. s=singlet; d=doublet; t=triplet; q=quartet; p=quintet; sextet; septet; br=broad; m=multiplet.

Elemental analyses were performed by Robertson Microlit Laboratories, Inc. Unless otherwise noted, mass spectra were obtained on a VG Patform II instrument using electrospray (ESI-MS) and MH$^+$ is reported. Thin-layer chromatography (TLC) was carried out on glass plates precoated with silica gel 60 $F_{254}$ (0.25 mm, EM Separations Tech.). Preparative thin-layer chromatography was carried out on glass sheets precoated with silica gel GF (2 mm, Analtech). Flash column chromatography was performed on Merck silica gel 60 (230-400 mesh). Melting points (mp) were determined in open capillary tubes on a Mel-Temp apparatus and are uncorrected.

The Following Schemes are Illustrative of Methods for Synthesizing Compounds of this Invention.

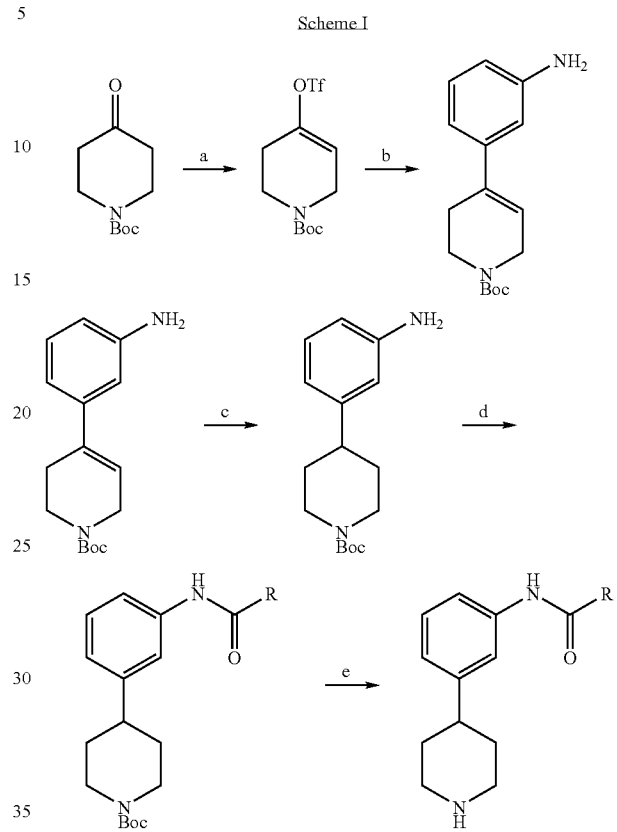

(a) LDA/PhNTf$_2$/THF/−78° C. then 0° C. overnight. (b) Aminophenylboronic acid/Pd(PPh)$_4$/LiCl/Na$_2$CO$_3$/DME-H$_2$O/reflux 3 h. (c) 10% Pd/C/H$_2$/EtOH/rt 24-48 h. (d) Acid chloride/triethylamine/THF/0° C. then rt 2-3 h or Carboxylic acid/EDC/DMAP/CH$_2$Cl$_2$/DMF/rt 12 h. (e) 4M HCl in 1,4-dioxane/rt 1 h or TFA/CH$_2$Cl$_2$/rt 10 min.

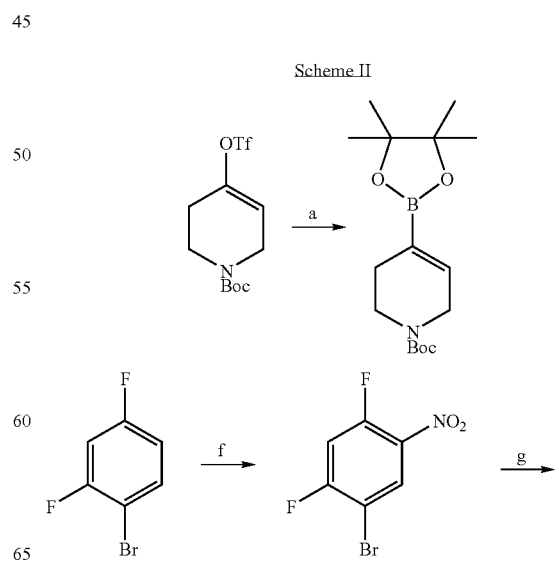

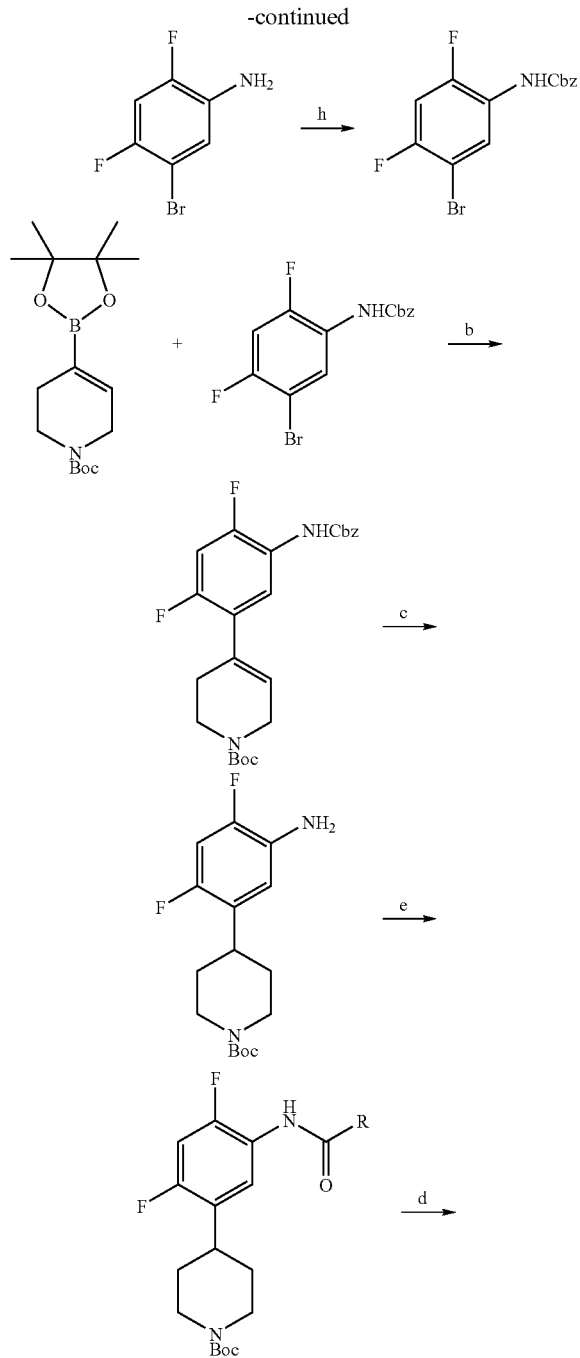

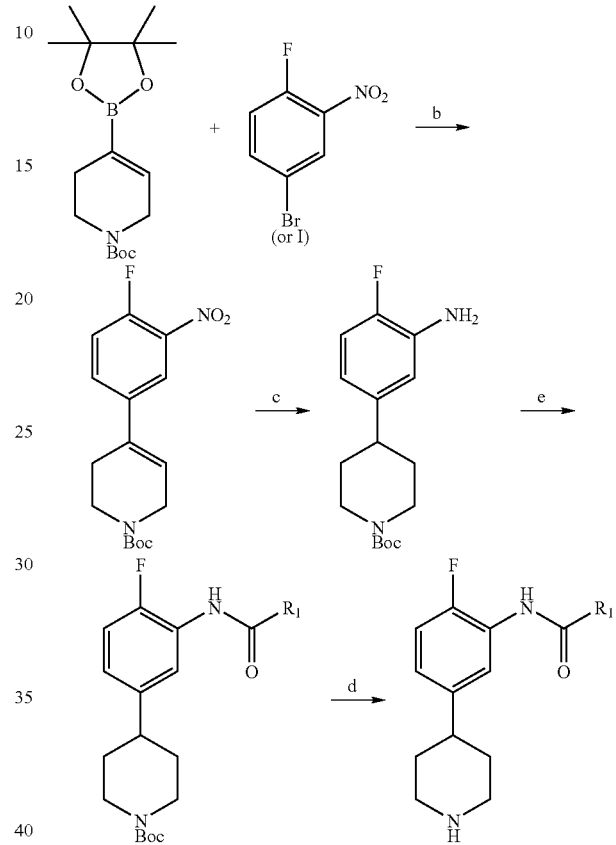

(a) Bis(pinacolato)diboron/KOAc/PdCl₂dppf/dppf/80° C. overnight. (b) K₂CO₃/PdCl₂dppf/DMF/80° C. overnight. (c) 10% Pd/C/H₂/EtOH/rt 24 h-72 h. (d) 4M HCl in 1,4-dioxane/rt 1 h or TFA/CH₂Cl₂/rt 10 min. (e) Carboxylic acid/EDC/DMAP/CH₂Cl₂/DMF/rt 12 h. (f) H₂SO₄/HNO₃, 0° C., 10 min. (g) Fe/NH₄Cl/THF/H₂O/EtOH/95° C., 1.5 h. (h) Cbz-Cl/NaHCO₃/CH₃CN/rt 12 h.

Scheme III (b) K₂CO₃/PdCl₂dppf/DMF/85° C. 24 h. (c) 10% Pd/C/H₂ (200 psi)/EtOAc/MeOH/rt 24 h-72 h. (d) 4M HCl in 1,4-dioxane/rt 1 h or TFA/CH₂Cl₂/rt 0.2 h. (e) Carboxylic acid/EDC/DMAP/CH₂Cl₂/DMF/rt 12 h.

GENERAL PROCEDURE FOR PIPERIDINE SYNTHESIS (SCHEME 1)

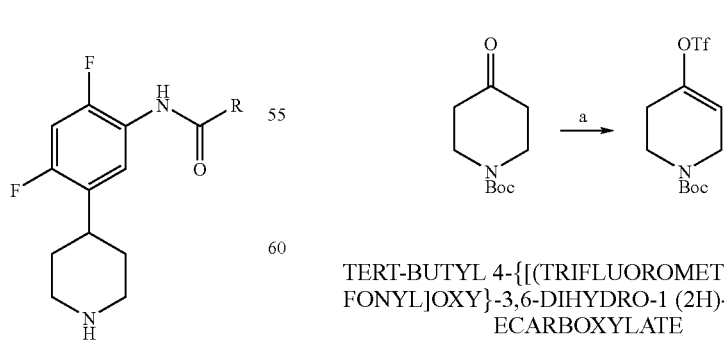

TERT-BUTYL 4-{[(TRIFLUOROMETHYL)SULFONYL]OXY}-3,6-DIHYDRO-1 (2H)-PYRIDINECARBOXYLATE n-Butyl lithium (17.6 mL, 44.2 mmol, 2.5 M in hexanes) was added to a solution of diisopropylamine (96.2 mL, 44.2 mmol) in anhydrous THF (40.0 mL) at 0° C. and the resulting mixture was stirred for 20 minutes. The reaction mixture was cooled to −78° C. and tert-butyl 4-oxo-1-piperidinecarboxylate (Aldrich Chemical Company, 7.97 g, 40.0 mmol) in THF (40.0 mL) was added dropwise to the reaction mixture, which was then stirred for 30 minutes. Tf$_2$NPh (42.0 mmol, 15.0 g) in THF (40.0 mL) was added dropwise to the reaction mixture and the reaction mixture was stirred at 0° C. overnight. The reaction mixture was concentrated in vacuo, redissolved in hexanes:EtOAc (9:1), passed through a plug of alumina and the alumina plug was washed with hexanes:EtOAc (9:1). The combined extracts were concentrated in vacuo to yield the desired product (16.5 g) which was contaminated with some starting material Tf$_2$NPh: $^1$H NMR (400 MHz, CDCl$_3$) δ 5.77 (s, 1H), 4.05 (dm, 2H, J=3.0 Hz), 3.63 (t, 2H, J=5.7 Hz), 2.45 (m, 2H), 1.47 (s, 9H).

TERT-BUTYL 4-[3-(AMINO)PHENYL]-1-PIPERIDINECARBOXYLATE

A mixture of tert-butyl 4-(3-aminophenyl)-3,6-dihydro-1 (2H)-pyridinecarboxylate (3.10 g, 11.3 mmol) and 10% Pd/C (1.00 g) in ethanol (100 mL) was hydrogenated at room temperature using the balloon method for 2 days. The reaction mixture was filtered through Celite and washed with ethanol. The combined ethanol extracts were concentrated in vacuo and the residue was chromatographed on silica (dichloromethane: methanol:isopropylamine 95:5:1) to give the desired product (2.63 g, 84%). $^1$H NMR (400 MHz, CDCl$_3$) δ 7.10 (t, 1H, J=7.6 Hz), 6.62 (d, 1H, J=8.4 Hz), 6.60-6.59 (m, 2H), 4.27-4.18 (m, 2H), 3.62-3.58 (m, 2H), 2.80-2.72 (m, 2H), 2.62-2.59 (m, 1H), 1.89-1.52 (m, 4H), 1.49 (s, 9H); ESMS m/e: 277.2 (M+H)$^+$.

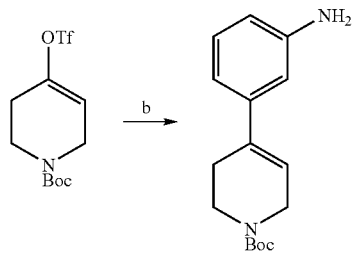

TERT-BUTYL 4-(3-AMINOPHENYL)-3,6-DIHYDRO-1(2H)-PYRIDINE CARBOXYLATE

A degassed mixture of 2.0 M aqueous Na$_2$CO$_3$ solution (4.20 mL), tert-butyl 4-{[(trifluoromethyl) sulfonyl]oxy}-3, 6-dihydro-1(2H)-pyridine carboxylate (0.500 g, 1.51 mmol), 3-aminophenylboronic acid hemisulfate (0.393 g, 2.11 mmol), lithium chloride (0.191 g, 4.50 mmol) and tetrakis-triphenylphosphine palladium (0.080 g, 0.075 mmol) in dimethoxyethane (5.00 mL) was heated at reflux temperature for 3 hours under Argon. The organic layer of the cooled reaction mixture was separated and the aqueous layer was washed with ethyl acetate (3×50 mL). The combined organic solutions were dried and concentrated in vacuo. The crude product was chromatographed (silica, hexanes:EtOAc: dichloromethane 6:1:1 with 1% isopropylamine) to give the desired product (0.330 g, 81%). $^1$H NMR (400 MHz, CDCl$_3$) δ 7.12 (t, 1H, J=7.60 Hz), 6.78 (d, 1H, J=8.4 Hz), 6.69 (t, 1H, J=2.0 Hz), 6.59 (dd, 1H, J=2.2, 8.0 Hz), 6.01 (br, 1H), 4.10-4.01 (d, 2H, J=2.4 Hz), 3.61 (t, 2H, J=5.6 Hz), 2.52-2.46 (m, 2H), 1.49 (s, 9H); ESMS m/e: 275.2 (M+H)$^+$.

Anal. Calc. for C$_{16}$H$_{24}$N$_2$O$_2$: C, 70.04; H, 8.08; N, 10.21. Found: C, 69.78; H, 7.80; N, 9.92.

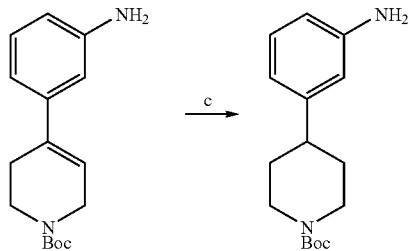

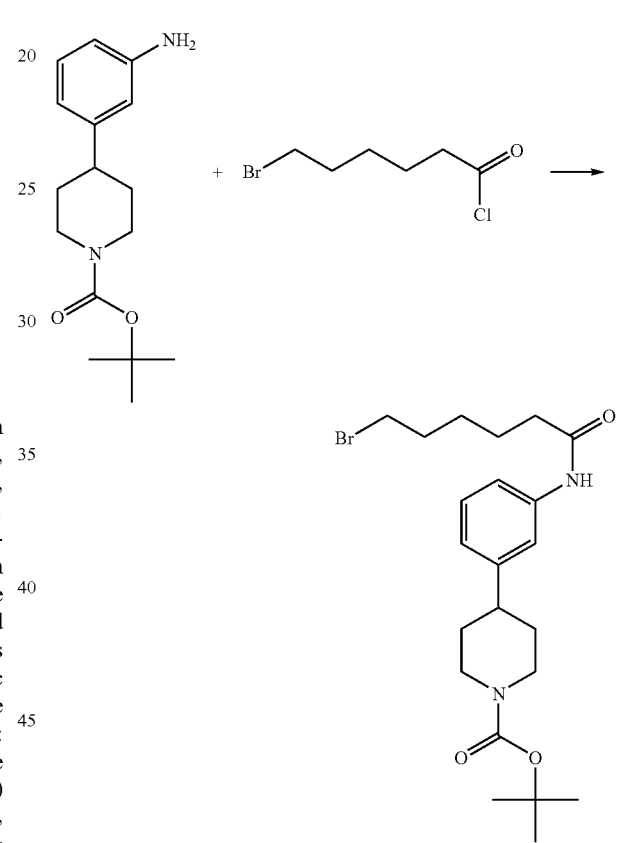

TERT-BUTYL 4-{3-[(6-BROMOHEXANOYL)AMINO]PHENYL}-1-PIPERIDINE CARBOXYLATE

A 25-mL RB-flask, charged with tert-butyl-4-[3-(amino) phenyl]-1-piperidinecarboxylate (2.00 mmol, 0.553 g), 6-bromohexanoyl chloride (0.427 g, 2.00 mmol, 1.0 eq.), triethylamine (0.404 g, 4.00 mmol) and THF (8.00 mL) was stirred at room temperature for 4 h. The reaction mixture was diluted with chloroform (50 mL) and washed with water (100 mL), brine, dried over MgSO$_4$ and concentrated in vacuo. The residue was purified by chromatography (silica gel, hexanes/EtOAc 10:1) to yield the desired product (0.921 g, 95.8%). $^1$H NMR (400 MHz, CDCl$_3$) δ 7.47 (s, 1H), 7.28-7.22 (m, 2H), 7.11 (s, 1H), 6.5 (d, 1H, J=7.0 Hz), 3.45-3.39 (m, 2H), 2.85-

2.70 (m, 2H), 2.68-2.58 (m, 1H), 2.37 (t, 2H, J=7.4 Hz), 1.96-1.71 (m, 7H), 1.68-1.50 (m, 5H), 1.48 (s, 9H); ESMS m/e: 355.4, 476.6.

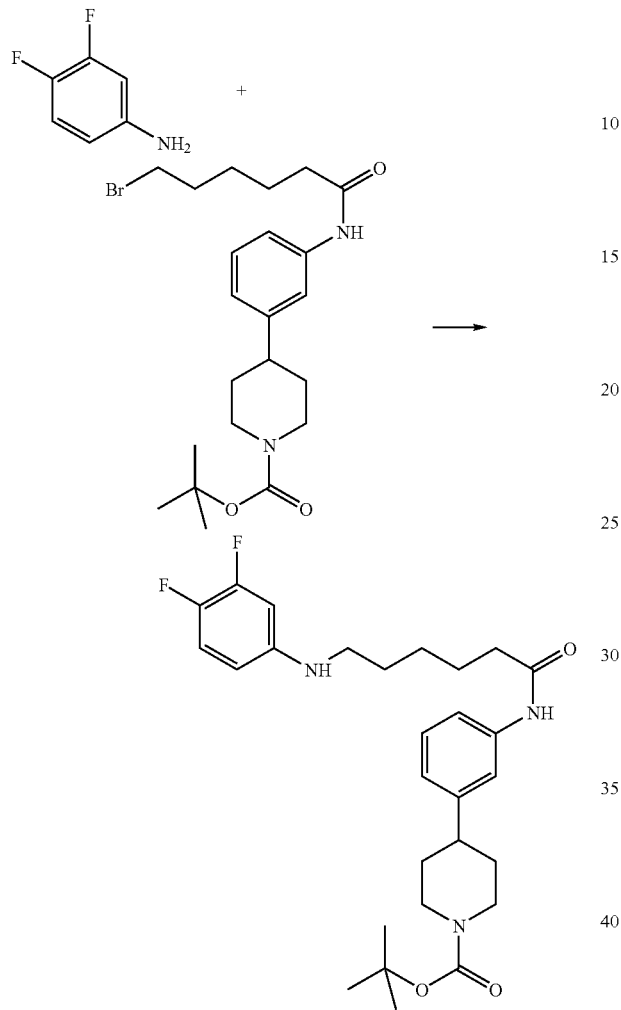

TERT-BUTYL 4-(3-{[6-(3,4-DIFLUOROANILINO) HEXANOYL]AMINO}PHENYL)-1-PIPERIDIN-ECARBOXYLATE

A 5-mL RB flask charged with tert-butyl-4-{3-[(6-bromohexanoyl)amino]phenyl}-1-piperidine carboxylate (40.9 mg, 0.100 mmol) 3,4-difluoroaniline (0.100 mmol, 12.9 mg), K₂CO₃ (0.100 mmol, 13.8 mg), NaI (22.5 mg, 0.150 mmol) and DMF (1.00 mL) was heated at 120° C. for 12 hours. The mixture was diluted with water (10 mL). The aqueous layer was extracted with chloroform (3×10 mL) and the combined extracts were washed with brine, dried over MgSO₄ and concentrated in vacuo. The residue was purified by chromatography (hexanes/EtOAc 10:1) to afford the desired product as a light yellow oil (7.14 mg, 14.3%). ¹H NMR (400 MHz, CDCl₃) δ 7.47 (s, 1H), 7.31-7.18 (m, 1H), 6.98-6.90 (m, 3H), 6.50-6.43 (m, 1H), 6.40-6.30 (m, 2H), 6.26-6.20 (m, 1H), 4.28-4.18 (m, 2H), 3.06 (t, 2H, J=7.2 Hz), 2.97-2.87 (m, 1H), 2.84-2.72 (m, 2H), 2.68-2.58 (m, 2H), 2.38 (t, 2H, J=7.4 Hz), 1.85-1.73 (m, 4H), 1.7-1.54 (m, 4H), 1.48 (s, 9H); ESMS m/e: 502.2 (M+H)⁺.

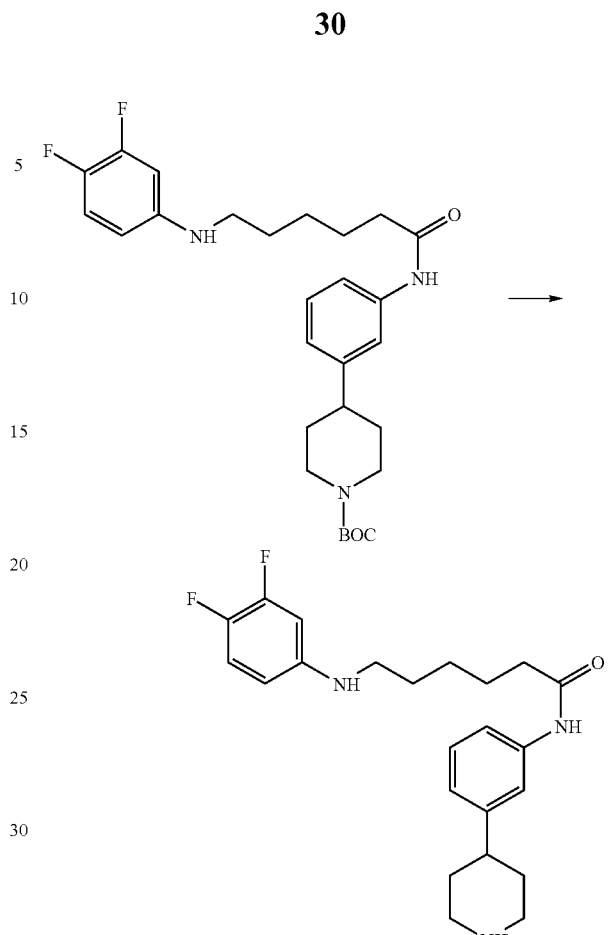

EXAMPLE 6

6-(3,4-Difluoroanilino)-N-[3-(4-Piperidinyl) Phenyl]Hexanamide

Into a solution of tert-butyl 4-(3-{[6-(3,4-difluoroanilino) hexanoyl]amino}phenyl)-1-piperidine carboxylate (11.2 mg, 0.0224 mmol) in dichloromethane (0.500 mL) at 0° C. was slowly added trifluoroacetic acid (25.5 mg, 2.24 mmol). The reaction mixture was stirred at room temperature for 10 min and concentrated in vacuo. The residue was dissolved in i-PrOH/CHCl₃ (1:3, 10 mL) and basified to pH 11 with 10% KOH, washed with H₂O, followed by brine. The organic layer was dried over MgSO₄ and concentrated in vacuo to give the desired product (8.98 mg, 99%): ¹H NMR (400. MHz, CDCl₃) δ 7.39-7.08 (m, 5H), 7.06-6.94 (m, 2H), 6.91-6.81 (m, 1H), 6.77-6.67 (m, 1H), 3.54-3.42 (m, 2H), 3.25-3.04 (m, 3H), 2.91-2.80 (m, 1H), 2.45-2.32 (m, 2H), 2.11-1.99 (m, 2H), 1.98-1.83 (m, 2H), 1.80-1.62 (m, 4H), 1.55-1.40 (m, 2H), 1.34-1.23 (m, 1H); ESMS m/e: 402.2 (M+H)⁺.

The following compounds were prepared according to the Scheme I.

EXAMPLE 1

5-(2-Methoxyphenyl)-N-[3-(4-Piperidinyl)Phenyl] Pentanamide tert-Butyl 4-(3-{[5-(2-methoxyphenyl)pentanoyl] amino}phenyl)-1-piperidinecarboxylate was subjected to Scheme I to afford the product. $^1$H NMR (400 MHz, CDCl$_3$) δ 7.52-6.68 (m, 8H), 3.74 (s, 3H), 3.61-3.35 (m, 2H), 3.14-2.90 (m, 2H), 2.88-2.56 (m, 3H), 2.52-2.27 (m, 2H), 2.10-1.51 (m, 8H); ESIMS m/e: 367.2 [M+H]$^+$.

EXAMPLE 2

5-Phenyl-N-[3-(4-Piperidinyl)Phenyl]Pentanamide tert-Butyl 4-{3-[(5-phenylpentanoyl)amino]phenyl}-1-piperidine carboxylate was subjected to Scheme I to afford the product. $^1$H NMR (400 MHz, CDCl$_3$) δ 7.51-6.83 (m, 9H), 3.66-3.40 (m, 2H), 3.08-2.80 (m, 2H), 2.78-2.45 (m, 3H), 2.43-2.28 (m, 2H), 2.08-1.60 (m, 8H); ESIMS m/e: 337.2 [M+H]$^+$.

EXAMPLE 3

6-Oxo-6-Phenyl-N-[3-(4-Piperidinyl)Phenyl]Hexanamide tert-Butyl 4-{3-[(6-oxo-6-phenylhexanoyl)amino]phenyl}-1-piperidinecarboxylate was subjected to Scheme I to afford the product. $^1$H NMR (400 MHz, CD$_3$OD) δ 7.98-7.83 (m, 2H), 7.60-7.31 (m, 4H), 7.28-7.12 (m, 2H), 6.97-6.87 (m, 1H), 3.48-3.31 (m, 2H), 3.10-2.68 (m, 5H), 2.40-2.26 (m, 2H), 2.05-1.63 (m, 8H); ESIMS m/e: 365.2 [M+H]$^+$.

EXAMPLE 4

2-Phenoxy-N-[3-(4-Piperidinyl)Phenyl]Nicotinamide

A mixture of tert-butyl 4-[3-(amino)phenyl]-1-piperidinecarboxylate (0.15 mmol), 2-phenoxynicotinoyl chloride (0.23 mmol) and triethylamine (0.30 mmol) in 3 mL of solvent (CH$_2$Cl$_2$:THF, 1:3) was stirred at room temperature for 12 hours. The reaction mixture was purified by preparative TLC (silica, EtOAc:hexane 1:1) to afford the desired product, tert-butyl 4-(3-{[(2-phenoxy-3-pyridinyl)carbonyl]amino}phenyl)-1-piperidinecarboxylate. Trifluoroacetic acid (1.0 mL) was added to the purified product dissolved in 1.0 mL of CH$_2$Cl$_2$ and the solution was stirred at room temperature for 1 minute. The reaction mixture was concentrated in vacuo to afford the TFA salt of the desired product. $^1$H NMR (400 MHz, CDCl$_3$) δ 9.85 (s, 1H), 8.76-8.64 (br, 1H), 8.30-8.14 (br, 1H), 7.67 (s, 1H), 7.49 (t, 2H, J=7.8 Hz), 7.42-7.29 (m, 3H), 7.24 (t, 3H, J=5.2 Hz), 7.03 (d, 1H, J=7.2 Hz), 3.59 (bd, 2H, J=11.5), 3.16-3.02 (m, 2H), 2.9-2.79 (m, 1H), 2.14-2.01 (m, 4H); ESIMS m/e: 374.1 [M+H]$^+$.

EXAMPLE 5

5-(4-Methoxyphenyl)-N-[3-(4-Piperidinyl)Phenyl]Pentanamide

Prepared according to the procedure described in scheme 1

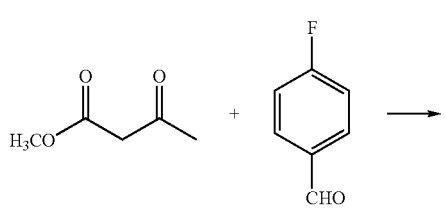

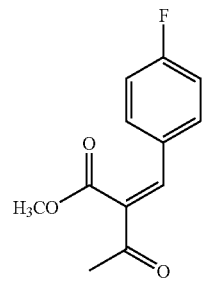

METHYL (2Z)-2-ACETYL-3-(4-FLUOROPHENYL)-2-PROPENOATE

A mixture of 4-fluorobenzaldehyde (25.5 g, 0.220 mol), methyl 3-oxobutanoate (21.80 g, 0.220 mol), and piperidine (1.0 mL) in anhydrous benzene (250 mL) was stirred for 10 minutes at room temperature and subsequently refluxed overnight in a Dean-Stark apparatus. The reaction mixture was then cooled to room temperature and the solvent was removed in vacuo to afford methyl (2Z)-2-acetyl-3-(4-fluorophenyl)-2-propenoate as a black solid (48.6 g, 99%), which was used for next step without purification.

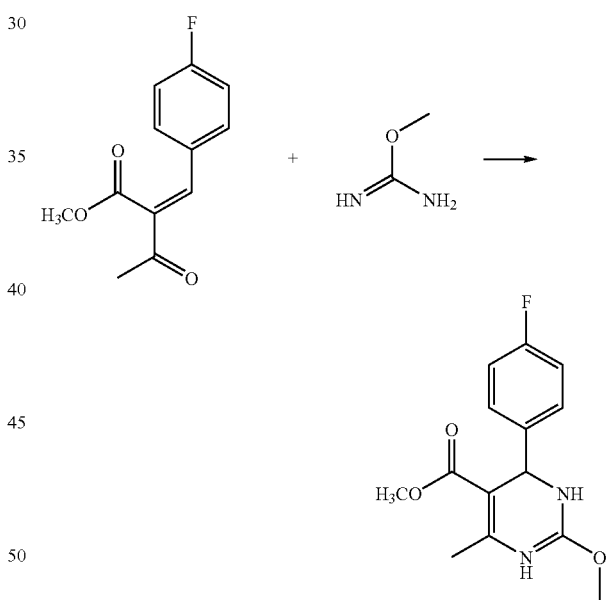

METHYL 6-(4-FLUOROPHENYL)-2-METHOXY-4-METHYL-1,6-DIHYDRO-5-PYRIMIDINECARBOXYLATE

A mixture of methyl (2Z)-2-acetyl-3-(4-fluorophenyl)-2-propenoate (0.220 mole, 48.8 g), O-methyl isourea hydrogensulfate (53.40 g, 0.310 mol, 1.5 eq.), NaHCO$_3$ (61.74 g, 0.74 mole, 3.5 equiv.) and ethanol (1.2 L) was refluxed for 24 h, cooled to room temperature, and filtered. The solid was washed with ethanol (200 mL) and the combined filtrate was concentrated in vacuo. The residue was purified by chromatography (silica gel, hexanes/EtOAc/Et$_3$N 50:50:0.1) to yield a mixture of tautomers (4:1, 33.0 g, 53.9%). $^1$H NMR (CDCl₃) δ 7.32-7.24 (m, 2H), 7.04-6.95 (m, 2H), 5.81 (s, 1H), 5.38 (d, 1H, J=2.9 Hz), 4.00 (s, 3H), 3.63 (s, 3H), 2.34 (s, 3H).

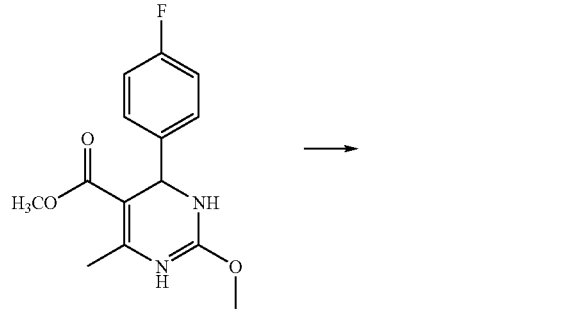

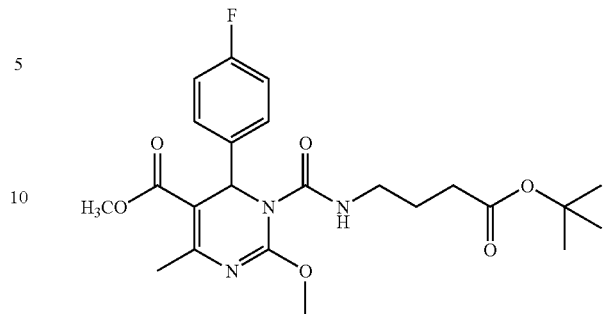

METHYL 1-{[(4-TERT-BUTOXY-4-OXOBUTYL) AMINO]CARBONYL}-6-(4-FLUOROPHENYL)-2-METHOXY-4-METHYL-1,6-DIHYDRO-5-PYRIMIDINECARBOXYLATE

To a solution of 5-methyl 1-(4-nitrophenyl) 6-(4-fluorophenyl)-2-methoxy-4-methyl-1,5(6H)-pyrimidinedicarboxylate (88.7 mg, 0.200 mmol) and K₂CO₃ (41.5 mg, 0.300 mmol) in CH₃OH/CH₂Cl₂ (0.1/2.0 mL) was added tert-butyl 4-aminobutanoate (31.8 mg, 0.200 mmol). After stirring at rt for 1 h, the mixture was washed with saturated Na₂CO₃ and brine. The organic layer was dried over MgSO₄ and concentrated in vacuo. The crude material was purified by flash chromatography (5%-10% 2 M NH₃/MeOH in 50% EtOAc/Hexanes) to afford the product (92.2 g, 99%). mp 135-138° C.; ¹H NMR (CD₃OD) δ 7.29-7.23 (m, 2H), 6.97-6.88 (m, 2H), 6.65 (s, 1H), 3.98 (s, 3H), 3.66 (s, 3H), 3.38-3.30 (m, 2H), 2.43 (s, 3H), 2.28 (t, 2H, J=7.2 Hz), 1.89-1.78 (m, 2H), 1.43 (s, 9H); ESMS m/e: 464.1 (M+H)⁺.

5-METHYL 1-(4-NITROPHENYL) 6-(4-FLUOROPHENYL)-2-METHOXY-4-METHYL-1,5(6H)-PYRIMIDINEDICARBOXYLATE

To a solution of methyl 6-(4-fluorophenyl)-2-methoxy-4-methyl-1,6-dihydro-5-pyrimidinecarboxylate (1.76 g, 6.34 mmol) and 4-dimethylaminopyridine (12.7 mmol, 1.55 g) in anhydrous CH₂Cl₂ (20.0 mL) was added solution of 4-nitrophenyl chloroformate (4.47 g, 22.2 mmol) in CH₂Cl₂ (20.0 mL) at 23° C. The reaction mixture was stirred for 2 hours at room temperature. The reaction mixture was diluted with CH₂Cl₂ (50 mL), washed with water, brine, dried over sodium sulfate and concentrated in vacuo. The residue was purified by flash column chromatography (hexanesiethyl acetate 4:1). The product was obtained as yellow syrup, which upon trituration with hexanes became a white powder (2.40 g, 84.3%). The crude product was used in next step without further purification.

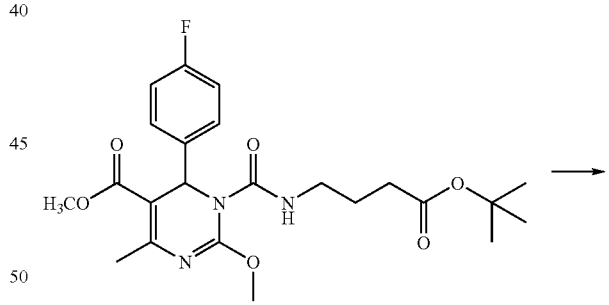

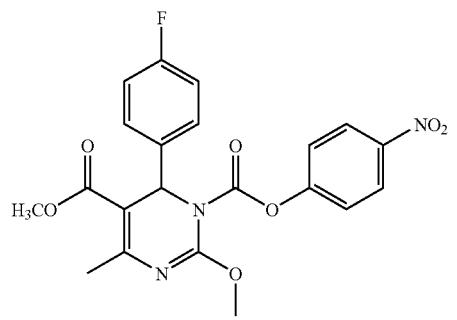

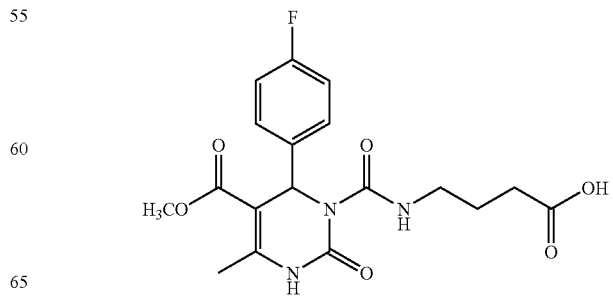

4-{[(6-(4-FLUOROPHENYL)-5-(METHOXYCARBONYL)-4-METHYL-2-OXO-3,6-DIHYDRO-1(2H)-PYRIMIDINYL)CARBONYL]AMINO}BUTANOIC ACID

Into a solution of methyl 1-{[(4-tert-butoxy-4-oxobutyl)amino]carbonyl}-6-(4-fluorophenyl)-2-methoxy-4-methyl-1,6-dihydro-5-pyrimidinecarboxylate (77.3 mg, 0.166 mmol) in dichloromethane (2.00 mL) at 0° C. was slowly added trifluoroacetic acid (189 mg, 1.66 mmol). The reaction mixture was stirred at room temperature for 10 min and concentrated in vacuo. The residue was dissolved in iso-PrOH/CHCl$_3$ (1:3, 10 mL) and basified to pH 11 with 10% KOH solution, washed with H$_2$O, followed by brine. The organic layer was dried over MgSO$_4$ and concentrated in vacuo to afford the desired product (58.1 mg, 88.9%). ESMS m/e: 394.1 (M+H)$^+$.

(2H)-pyrimidinyl)carbonyl]amino}butanoic acid (77.0 mg, 0.189 mmol), tert-butyl-4-[3-(amino)phenyl]-1-piperidinecarboxylate (52.2 mg, 0.189 mmol), 1-[3-(dimethylamino)propyl]-3-ethylcarbodiimide hydrochloride (0.567 mmol, 87.8 mg), 4-dimethylaminopyridine (11.5 mg, 0.0945 mmol) in DMF:DCM (0.2:2.0 mL) at room temperature. The reaction mixture was stirred for 12 h and water (10.0 mL) was added to the reaction mixture. The organic layer was separated and the aqueous layer was extracted with CHCl$_3$ (3×10 mL). The combined organic extracts were washed with brine, dried over MgSO$_4$, filtered and concentrated in vacuo. The residue was chromatographed (silica, hexanes:EtOAc 9:1) to afford the desired product (40.9 mg, 33.2%): $^1$H NMR (400 MHz, CDCl$_3$) δ 8.03 (m, 3H), 7.57 (s, 1H), 7.36-7.28 (m, 3H), 7.27-7.22 (m, 1H), 6.97-6.89 (m, 3H), 6.72 (s, 1H), 3.72 (s, 3H), 3.47-3.37 (m, 2H), 2.42 (s, 3H), 2.37-2.29 (m, 2H), 1.98-1.91 (m, 2H), 1.86-1.75 (m, 2H), 1.72-1.54 (m, 7H), 1.48 (s, 9H); ESMS m/e: 652.2 (M+H)$^+$.

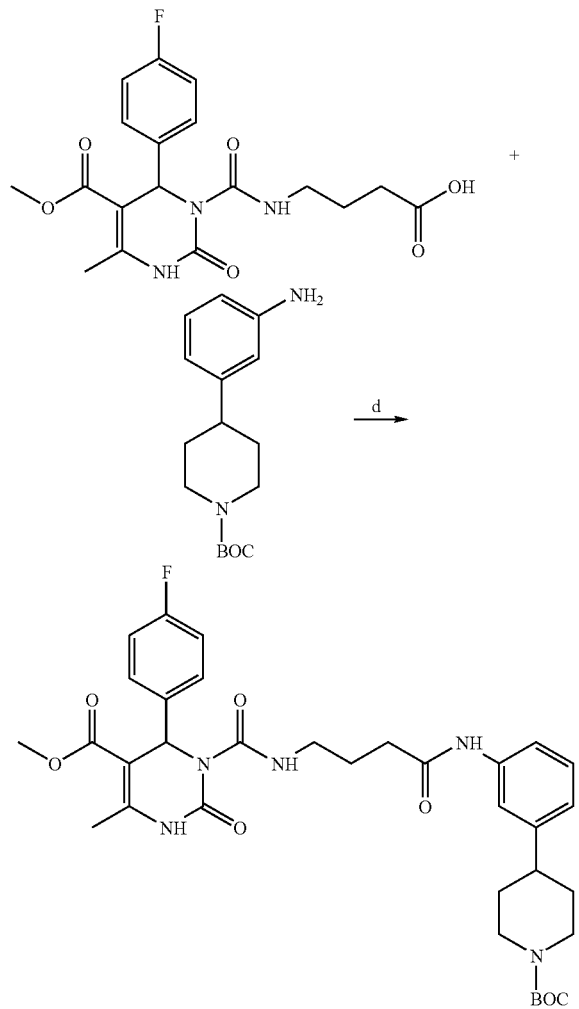

EXAMPLE 7

Methyl 4-(4-Fluorophenyl)-6-Methyl-2-Oxo-3-[({4-OXO-4-[3-(4-Piperidinyl)Anilino]Butyl}Amino)Carbonyl]-1,2,3,4-Tetrahydro-5-Pyrimidinecarboxylate

METHYL 3-{[(4-{3-[1-(TERT-BUTOXYCARBONYL)-4-PIPERIDINYL]ANILINO}-4-OXOBUTYL)AMINO]CARBONYL}-4-(4-FLUOROPHENYL)-6-METHYL-2-OXO-1,2,3,4-TETRAHYDRO-5-PYRIMIDINE CARBOXYLATE

A 10-mL RB-flask was charged with 4-{[(6-(4-fluorophenyl)-5-(methoxycarbonyl)-4-methyl-2-oxo-3,6-dihydro-1

Into a solution of methyl 3-{[(4-{3-[1-(tert-butoxycarbonyl)-4-piperidinyl]anilino}-4-oxobutyl)amino]carbonyl}-4-(4-fluorophenyl)-6-methyl-2-oxo-1,2,3,4-tetrahydro-5-pyrimidinecarboxylate (40.9 mg, 0.0628 mmol) in dichloromethane (2.00 mL) at 0° C. was slowly added trifluoroacetic acid (71.6 mg, 0.628 mmol). The reaction mixture was stirred at room temperature for 10 min and concentrated in vacuo. The residue was dissolved in iso-PrOH/CHCl$_3$ (1:3, 10 mL) and basified to pH 11 with 10% KOH solution, washed with H$_2$O, followed by brine. The organic layer was dried over MgSO$_4$ and concentrated in vacuo to afford the desired product (34.6 mg, 99%): $^1$H NMR (400 MHz, CDCl$_3$) δ 8.00 (m, 3H), 7.67 (s, 1H), 7.35-7.27 (m, 4H), 7.04-6.98 (m, 3H), 6.65 (s, 1H), 3.72 (s, 3H), 3.5-3.48 (m, 2H), 3.20-3.11 (m, 3H), 2.42 (t, 2H, J=7.5 Hz), 2.36 (s, 3H), 2.13-2.06 (m, 2H), 1.97-1.88 (m, 4H); ESMS m/e: 552.3 (M+H)$^+$.

organic extracts were washed with brine, dried over MgSO$_4$, filtered and concentrated in vacuo. The residue was chromatographed (silica, hexanes:EtOAc 9:1) to afford the desired product (378 mg, 67.8%): $^1$H NMR (400 MHz, CDCl$_3$) δ 8.03 (m, 2H), 7.57 (s, 1H), 7.36-7.28 (m, 3H), 7.27-7.22 (m, 1H), 6.97-6.89 (m, 3H), 6.72 (s, 1H), 3.72 (s, 3H), 3.47-3.37 (m, 2H), 2.42 (s, 3H), 2.37-2.29 (m, 2H), 1.98-1.91 (m, 2H), 1.86-1.75 (m, 2H), 1.72-1.54 (m, 7H), 1.48 (s, 9H); ESMS m/e: 554.3 (M−100).

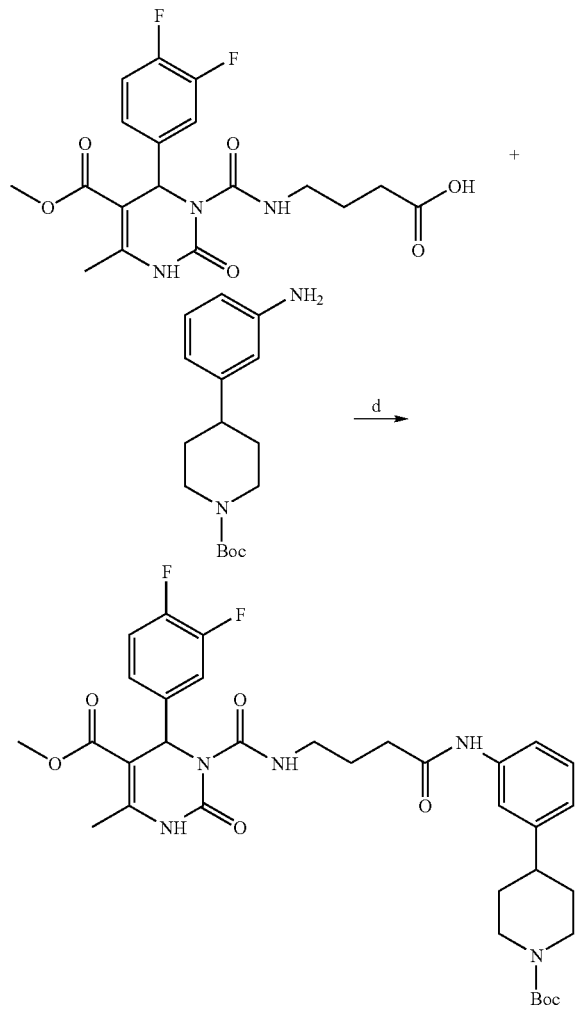

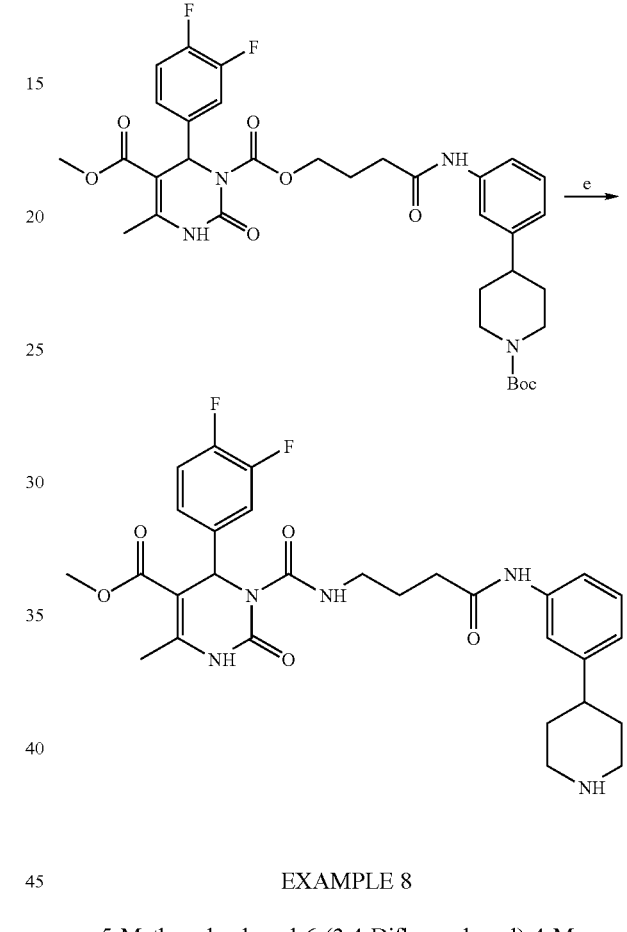

TERT-BUTYL-4-{3-[(4-{[(5-METHOXYLCARBO-NYL-6-(3,4-DIFLUOROPHENYL)-4-METHYL-2-OXO-3,6-DIHYDRO-1(2H)-PYRIMIDINYL)CARBONYL]AMINO}BUTANOYL)AMINO]PHENYL}-1-PIPERIDINECARBOXYLATE

A 50-mL RB-flask was charged with 4-{[(5-acetyl-6-(3,4-difluorophenyl)-4-methyl-2-oxo-3,6-dihydro-1(2H)-pyrimidinyl)carbonyl]amino}butanoic acid (313 mg, 0.854 mmol), tert-butyl-4-[3-(amino)phenyl]-1-piperidinecarboxylate (235 mg, 0.857 mmol), 1-[3-(Dimethylamino)propyl]-3-ethylcarbodiimide hydrochloride (7.71 mmol, 265 mg), 4-dimethylaminopyridine (10.4 mg, 0.0854 mmol) in DMF:DCM (0.8:8.0 mL) at room temperature. The reaction mixture was stirred for 12 h and water (20.0 mL) was added to the reaction mixture. The organic layer was separated and the aqueous layer was extracted with CHCl$_3$ (3×10 mL). The combined

EXAMPLE 8

5-Methoxylcarbonyl-6-(3,4-Difluorophenyl)-4-Methyl-2-Oxo-N-{4-Oxo-4-[3-(4-Piperidinyl)Anilino]Butyl}-3,6-Dihydro-1(2H)-Pyrimidinecarboxamide Into a solution of tert-butyl 4-{3-[(4-{[(5-Methoxylcarbonyl-6-(3,4-difluorophenyl)-4-methyl-2-oxo-3,6-dihydro-1 (2H)-pyrimidinyl)carbonyl]amino}butanoyl)amino]phenyl}-1-piperidinecarboxylate (378 mg, 0.579 mmol) in dichloromethane (5.00 mL) at 0° C. was slowly added trifluoroacetic acid (659 mg, 5.79 mmol). The reaction mixture was stirred at room temperature for 10 min and concentrated in vacuo. The residue was dissolved in iso-PrOH/CHCl$_3$ (1:3, 10 mL) and basified to pH 11 with 10% KOH solution, washed with H$_2$O, followed by brine. The organic layer was dried over MgSO$_4$ and concentrated in vacuo. The residue was purified by flash chromatography (dichloromethane: methanol 5:1) to afford the desired product (93.8 mg, 29.3%): $^1$H NMR (400 MHz, CDCl$_3$) δ 7.46-7.43 (m, 3H), 7.35-7.29 (m, 2H), 7.12-7.06 (m, 3H), 6.63-6.60 (m, 1H), 6.56-6.52 (m, 2H), 3.26 (s, 3H), 3.22 (s, 3H), 2.72 (dt, 6H, J=2.3, 12.3 Hz), 2.66 (tt, 2H, J=3.6, 11.9 Hz), 2.55 (tt, 1H, J=3.8, 11.9 Hz), 1.88-1.82 (m, 1H), 1.75-1.63 (m, 6H); ESMS m/e: 554.3 (M+H)$^+$.

GENERAL PROCEDURE FOR PIPERIDINE SYNTHESIS (SCHEME 2)

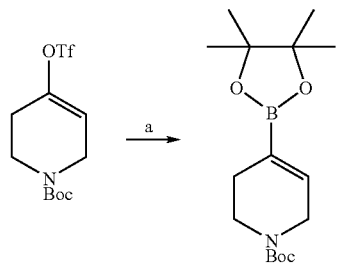

TERT-BUTYL 4-(4,4,5,5-TETRAMETHYL-1,3,2-DIOXABOROLAN-2-YL)-3,6-DIHYDRO-1(2H)-PYRIDINECARBOXYLATE

To a 50-mL RB-flask, charged with bis(pinacolato)diboron (422 mg, 1.66 mmol), KOAc (444 mg, 4.53 mmol), PdCl$_2$dppf (37.0 mg, 3.00 mol %) and dppf (25.0 mg; 3.00 mol %) was added a solution of tert-butyl 4-{[(trifluoromethyl)sulfonyl]oxy}-3,6-dihydro-1(2H)-pyridinecarboxylate (500 mg, 1.51 mmol) in 1,4-dioxane (10.0 mL) at room temperature under argon. The mixture was heated at 80° C. overnight. After cooling to room temperature, the mixture was filtered through Celite and the Celite was washed with EtOAc (3×20 mL) The combined filtrates were washed with H$_2$O and brine, dried over MgSO$_4$, filtered and concentrated in vacuo. The crude product was purified by flash chromatography (EtOAc:hexanes 1:9) to afford tert-butyl 4-(4,4,5,5-tetramethyl-1,3,2-dioxaborolan-2-yl)-3,6-dihydro-1(2H)-pyridinecarboxylate (355 mg, 76%): $^1$H NMR (400 MHz, CDCl$_3$) δ 6.60-6.34 (br, 1H), 4.06-3.86 (br, 2H), 3.55-3.34 (br, 2H), 2.35-2.09 (br, 2H), 1.46 (s, 9H), 1.26 (s, 12H); ESMS m/e: 310.4 (M+H)$^+$.

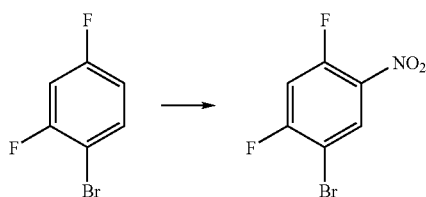

5-BROMO-2,4-DIFLUORONITROBENZENE

To a suspension of 1-bromo-2,4-difluorobenzene (53.0 mmol, 6.00 mL) in concentrated H$_2$SO$_4$ (38.5 mL) at 0° C. was added dropwise concentrated HNO$_3$ (34.0 mL) maintaining internal temperature below 20° C. The resulting mixture was stirred for 10 min at 0° C., then poured into ice/water with vigorous stirring. The mixture was extracted with Et$_2$O (3×100 mL). The combined organic extracts were washed with aqueous NaHCO$_3$ solution (3×100 mL) and brine, dried over MgSO$_4$, filtered and concentrated in vacuo. The crude product was purified by flash chromatography (EtOAc:hexanes 1:9) to afford 5-bromo-2,4-difluoronitrobenzene as a yellow oil (12.2 g, 97%). $^1$H NMR (400 MHz, CDCl$_3$) δ 8.45 (t, 1H, J=7.5 Hz), 7.16 (dd, 1H, J=11.0, 8.6 Hz); ESMS m/e: 240, 238, 223, 221, 112

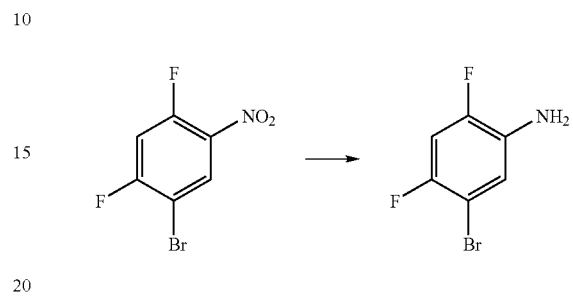

5-BROMO-2,4-DIFLUOROANILINE

A 250-mL RB-flask, charged with 5-bromo-2,4-difluoronitrobenzene (5.04 g, 21.3 mmol), saturated NH$_4$Cl (25.0 mL), iron powder (5.00 g, 89.5 mmol), ethanol (100 mL), THF (50.0 mL) and water (25.0 mL) was refluxed at 95° C. for 1.5 hours. After cooling to room temperature, saturated NaHCO$_3$ (100 mL) was added and the mixture was filtered through Celite and the Celite was washed with EtOAc (3×50 mL). The combined filtrates were washed with H$_2$O and brine, dried over MgSO$_4$, filtered and concentrated in vacuo. The crude product was purified by flash chromatography (EtOAc:hexanes 1:9) to afford 5-bromor-2,4-difluoroaniline (2.61 g, 59.1%). $^1$H NMR (400 MHz, CDCl$_3$) δ 6.97 (dd, 1H, J=7.2, 6.7 Hz), 6.85 (t, 1H, J=8.2 Hz), 3.63 (br, 2H).

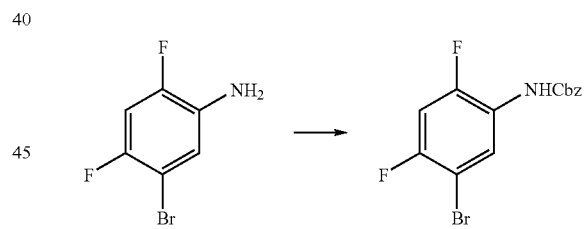

BENZYL 5-BROMO-2,4-DIFLUOROPHENYLCARBAMATE

Into a 250-mL RB-flask was added 5-bromor-2,4-difluoroaniline (5.00 g, 24.2 mmol), chlorobenzylformate (4.10 mL, 29.0 mmol), NaHCO$_3$ (6.10 g, 72.6 mmol) and acetonitrile (100 mL). The reaction mixture was stirred at 25° C. for 12 hours, then filtered through a coarse sintered glass, fritted funnel, washed with EtOAc (3×20 mL) and concentrated in vacuo. The filtrate was washed with H$_2$O and brine, dried over MgSO$_4$, filtered and concentrated in vacuo. The crude product was purified by flash chromatography (EtOAc:hexanes 1:9) to afford benzyl 5-bromor-2,4-difluorophenylcarbamate (5.05 g, 61.0%): $^1$H NMR (400 MHz, CDCl$_3$) δ 8.38 (s, 1H), 7.49-7.31 (m, 5H), 6.94-6.89 (m, 1H), 6.81-6.77 (m, 1H), 5.22 (s, 2H); ESMS m/e: 340.1 (M−H$^+$).

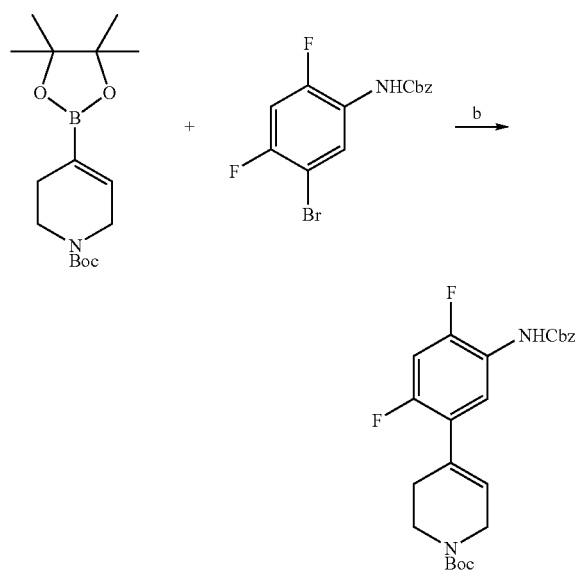

TERT-BUTYL 4-(5-{[(BENZYLOXY)CARBONYL]AMINO}-2,4-DIFLUOROPHENYL)-3,6-DIHYDRO-1(2H)-PYRIDINECARBOXYLATE

To a 250-mL RB-flask containing tert-butyl 4-(4,4,5,5-tetramethyl-1,3,2-dioxaborolan-2-yl)-3,6-dihydro-1(2H)-pyridinecarboxylate (4.58 g, 14.8 mmol), $K_2CO_3$ (6.14 g, 44.4 mmol) and $PdCl_2dppf$ (1.48 mmol, 1.21 g) was added a solution of benzyl 5-bromo-2,4-difluorophenylcarbamate (5.05, 14.8 mmol) in DMF (150 mL) at room temperature under argon. The mixture was heated to 80° C. under argon overnight. After cooling to room temperature, the mixture was filtered through Celite and the Celite was washed with EtOAc (3×100 mL). The filtrates were washed with $H_2O$ (3×200 mL), brine (100 mL), dried over $MgSO_4$, filtered and concentrated in vacuo. The crude material was purified flash chromatography (EtOAc/hexanes 1:9) to afford tert-butyl 4-(5-{[(benzyloxy)carbonyl]amino}-2,4-difluorophenyl)-3,6-dihydro-1(2H)-pyridinecarboxylate (1.60 g, 24.5%): $^1$H NMR (400 MHz, $CDCl_3$) δ 8.08 (s, 1H), 7.45-7.35 (m, 5H), 6.85-6.70 (m, 1H), 5.95-5.85 (m, 1H), 5.20 (s, 2H), 4.05 (m, 2H), 3.6-3.5 (m, 2H), 2.5-2.4 (m, 2H), 1.50 (s, 9H); ESMS m/e: 443.3 (M–H$^+$).

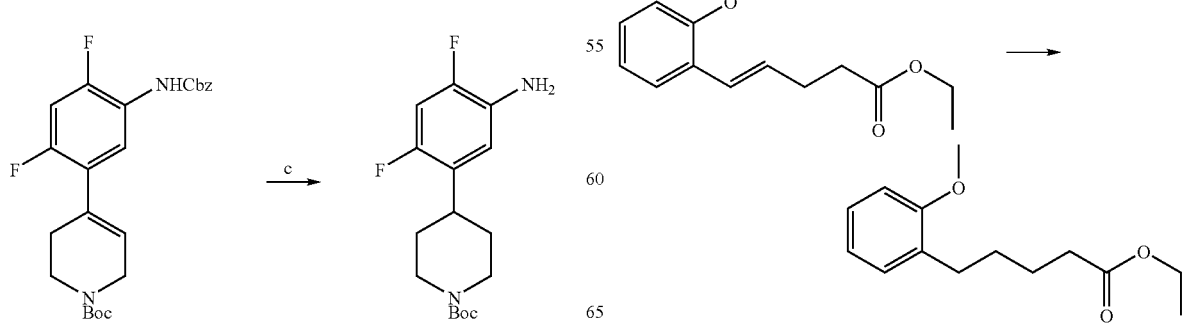

TERT-BUTYL 4-(5-AMINO-2,4-DIFLUOROPHENYL)-1-PIPERIDINECARBOXYLATE

A mixture of tert-butyl 4-(5-{[(benzyloxy)carbonyl]amino}-2,4-difluorophenyl)-3,6-dihydro-1(2H)-pyridinecarboxylate (1.60 g, 3.60 mmol) and 5% Pd/C (320 mg, 0.100 mmol) in ethyl acetate (25.0 mL) and methanol (25.0 mL) was hydrogenated at room temperature for 72 hours using hydrogen bomb (200 psi). The reaction mixture was filtered through Celite and washed with EtOAc/MeOH (1:1, 3×50 mL). The filtrate was concentrated in vacuo to afford tert-butyl 4-(5-amino-2,4-difluorophenyl)-1-piperidinecarboxylate (1.39 g, 100%). $^1$H NMR (400 MHz, $CDCl_3$) δ 6.73 (t, 1H, J=10.6 Hz), 6.60-6.54 (dd, 1H, J=7.6, 6.57 Hz), 4.20 (br, 2H), 3.55 (s, 2H), 2.96-2.72 (m, 3H), 1.79-1.71 (m, 2H), 1.58-1.52 (m, 2H), 1.47 (s, 9H); ESMS m/e: 257.3 (M–56).

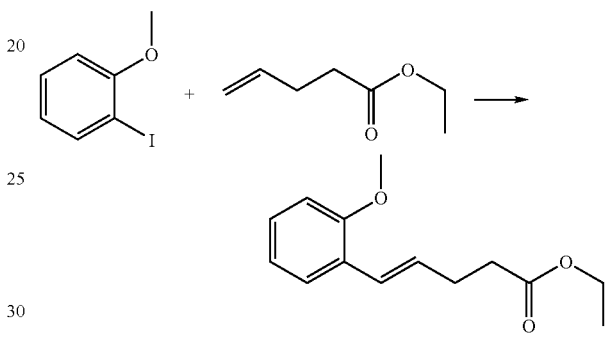

ETHYL (4E)-5-(2-METHOXYPHENYL)-4-PENTENOATE

To a 200-mL RB-flask was added 2-iodoanisole (5.00 g, 21.4 mmol), ethyl 4-pentenoate (3.30 g, 25.6 mmol), tetrakis(triphenyl phosphine)palladium(0) (0.740 g, 0.600 mmol), triethylamine (6.00 mL, 42.7 mmol) and a mixture of $CH_3CN$ (45.0 mL) and THF (15.0 mL). The reaction mixture was refluxed for overnight and then cooled to room temperature. After solvents were removed in vacuo, the resulted dark brown residue was dissolved in 5% HCl (aq) and extracted with $CH_2Cl_2$ three times. The combined extracts were washed by saturated $NaHCO_3$ solution, dried over $MgSO_4$, concentrated in vacuo. The dark brown oil was purified by chromatography (silica gel, EtOAc/Hexanes 1:10) to afford the product as light yellow oil (3.40 g, 68%).

ETHYL 5-(2-METHOXYPHENYL)PENTANOATE

To a solution of ethyl (4E)-5-(2-methoxyphenyl)-4-pentenoate (3.40 g, 14.5 mmol) in a mixture of EtOAc and MeOH (40.0/10.0 mL), Pd/C (palladium on carbon 10%, 0.700 g) was added in small portions to avoid fire. The reaction mixture was then stirred for overnight at room temperature under 300 psi of hydrogen. After the pressure was released, the mixture was filtered through Celite and the Celite was washed with EtOAc (3×50 mL). The filtrate was concentrated in vacuo to afford crude product as a light yellow oil (3.40 g 100%), which was used without further purification.

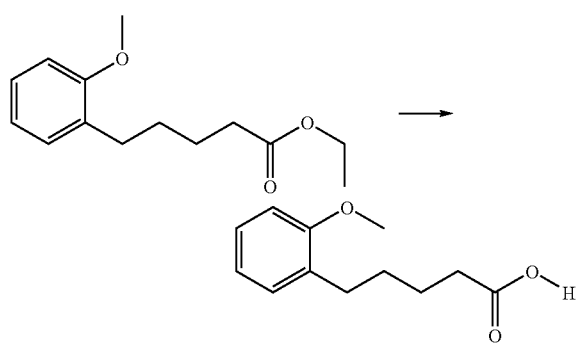

5-(2-METHOXYPRENYL)PENTANOIC ACID

Into a 250-mL RB-flask was charged with ethyl 5-(2-methoxyphenyl)pentanoate (3.40 g, 14.5 mmol), NaOH (1.74 g, 42.8 mmol), THF (25.0 mL) and water (25.0 mL). The reaction mixture was refluxed for 2 hours and cooled to room temperature. The reaction mixture was concentrated in vacuo and the resulted aqueous solution was acidified with 6 M HCl to pH<5. The acidic mixture was extracted with chloroform/isopropyl alcohol (3:1, 3×50 mL) and the combined organic phases were washed with brine, dried over $Na_2SO_4$ and concentrated in vacuo to afford the product as a white solid (2.68 g, 90%), which was used without further purification. $^1$H NMR (400 MHz, MeOD) δ 7.23-7.03 (m, 2H), 6.95-6.76 (m, 2H), 3.81 (s, 3H), 2.63 (t, 2H, J=7.2 Hz), 2.38 (t, 2H, J=7.2 Hz), 1.77-1.53 (m, 4H)

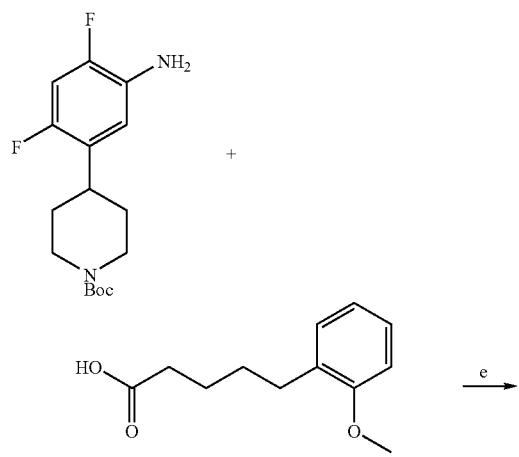

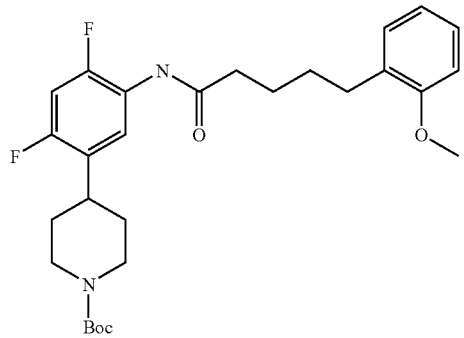

TERT-BUTYL 4-(2,4-DIFLUORO-5-{[5-(2-METHOXYPHENYL)PENTANOYL]AMINO}PHENYL)-1-PIPERIDINECARBOXYLATE

A 15-mL RB-flask was charged with 5-(2-methoxyphenyl)pentanoic acid (69.0 mg, 0.810 mmol), tert-butyl 4-(5-amino-2,4-difluorophenyl)-1-piperidinecarboxylate (229 mg, 0.740 mmol), 1-[3-(Dimethylamino)propyl]-3-ethylcarbodimide hydrochloride (2.22 mmol, 426 mg), 4-dimethylaminopyridine (9 mg, 0.07 mmol) in DMF:DCM (0.2:5.0 mL) at room temperature. The reaction mixture was stirred for 12 h and water (10.0 mL) was added to the reaction mixture.

The organic layer was separated and the aqueous layer was extracted with $CHCl_3$ (3×10 mL). The combined organic extracts were washed with brine, dried over $MgSO_4$, filtered and concentrated in vacuo to afford tert-butyl 4-(2,4-difluoro-5-{[5-(2-methoxyphenyl)pentanoyl]amino}phenyl)-1-piperidinecarboxylate (310 mg, 83.2%): $^1$H NMR (400 MHz, $CDCl_3$) δ 8.36-8.13 (m, 1H), 7.39 (s, 1H), 7.26-7.06 (m, 1H), 7.06-6.92 (m, 1H), 6.92-6.75 (m, 3H), 4.41-4.02 (m, 2H), 3.80 (s, 3H), 2.90-2.70 (m, 2H), 2.70-2.63 (m, 2H), 2.63-2.51 (m, 1H), 2.49-2.32 (m, 2H), 1.87-1.72 (m, 4H), 1.72-1.63 (m, 2H), 1.63-1.52 (m, 2H), 1.48 (s, 9H).

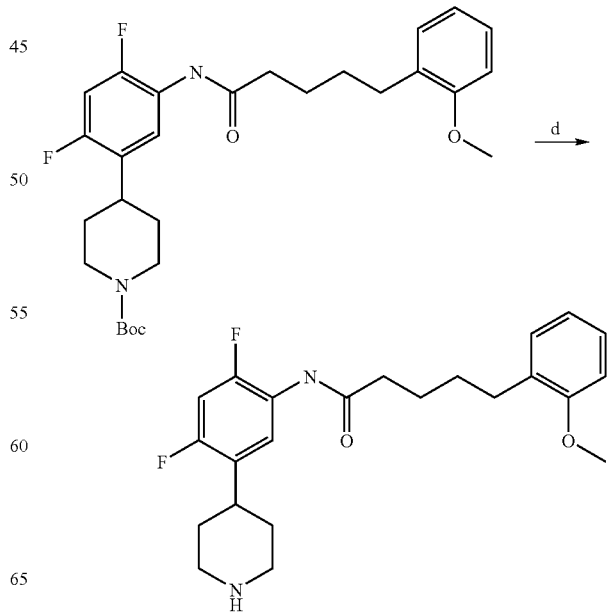

EXAMPLE 11

N-[2,4-Difluoro-5-(4-Piperidinyl)Phenyl]-5-(2-Methoxyphenyl)Pentanamide

Into a solution of tert-butyl 4(2,4-difluoro-5-{[5-(2-methoxyphenyl)pentanoyl]amino}phenyl)-1-piperidinecarboxylate (310 mg, 0.620 mmol) in dichloromethane (5.00 mL) at 0° C. was slowly added trifluoroacetic acid (707 mg, 6.20 mmol). The reaction mixture was stirred at room temperature for 10 min and concentrated in vacuo. The residue was dissolved in i-PrOH/CHCl$_3$ (1:3, 10 mL) and basified to pH 11 with 10% KOH solution, washed with H$_2$O, followed by brine. The organic layer was separated, dried over MgSO$_4$ and concentrated in vacuo to afford the desired product (108 mg, 43.3%). $^1$H NMR (400 MHz, CDCl$_3$) δ 7.59 (t, 1H, J=8.2 Hz), 7.10-6.96 (m, 2H), 6.90-6.68 (m, 3H), 3.67 (s, 3H), 3.09 (d, 2H, J=12.4 Hz), 2.89 (tt, 1H, J=11.8 Hz), 2.69 (dt, 2H, J=2.6, 12.4 Hz), 2.54 (t, 2H, J=7.2 Hz), 2.33 (t, 2H, J=7.2 Hz), 1.76-1.48 (m, 8H); ESMS m/e: 403.3 (M+H)$^+$.

GENERAL PROCEDURE FOR PIPERIDINE SYNTHESIS (SCHEME 3)

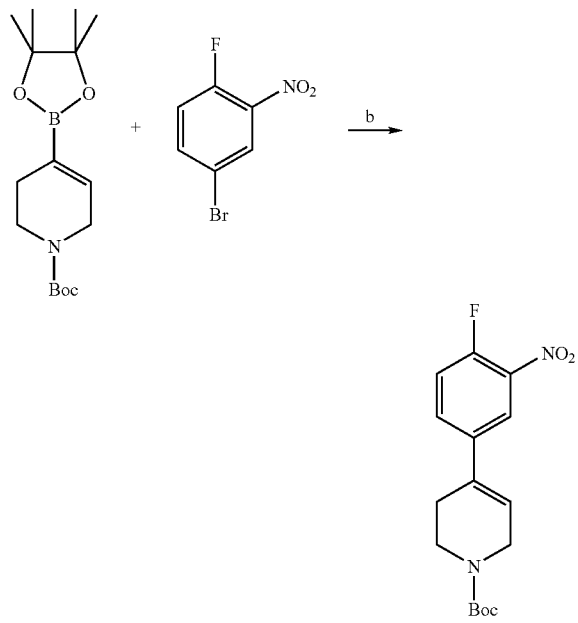

TERT-BUTYL 4-(4-FLUORO-3-NITROPHENYL)-3,6-DIHYDRO-1(2H)-PYRIDINECARBOXYLATE

To a 150-mL RB-flask containing tert-butyl 4-(4,4,5,5-tetramethyl-1,3,2-dioxaborolan-2-yl)-3,6-dihydro-1(2H)-pyridinecarboxylate (5.58 g, 16.5 mmol), K$_2$CO$_3$ (5.60 g, 40.5 mmol) and PdCl$_2$dppf (1.48 mmol, 1.21 g) was added a solution of 4-bromo-1-fluoro-2-nitrobenzene (3.30 g, 15.0 mmol) in DMF (50.0 mL) at room temperature under argon. The mixture was heated to 80° C. under argon for 12 hours. After cooling to room temperature, the mixture was filtered through Celite and the Celite was washed with EtOAc (3×100 mL). The filtrates were washed with H$_2$O (3×200 mL), brine (100 mL), dried over MgSO$_4$, filtered and concentrated in vacuo. The crude material was purified by flash chromatography (EtOAc/hexanes 1:9) to afford tert-butyl 4-(4-fluoro-3-nitrophenyl)-3,6-dihydro-1(2H)-pyridinecarboxylate (3.13 g, 65.1%): $^1$H NMR (400 MHz, CDCl$_3$) δ 8.06-7.89 (m, 1H), 7.66-7.49 (m, 1H), 7.30-7.10 (m, 1H), 6.19-5.95 (br, 1H), 4.10-3.95 (m, 2H), 3.58 (t, 2H, J=5.6 Hz), 2.49-2.34 (m, 2H), 1.42 (s, 9H).

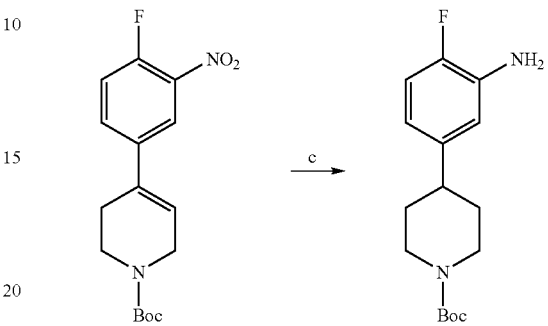

TERT-BUTYL-4-(3-AMINO-4-FLUOROPHENYL)-1-PIPERIDINECARBOXYLATE

A mixture of tert-butyl 4-(4-fluoro-3-nitrophenyl)-3,6-dihydro-1(2H)-pyridinecarboxylate (2.35 g, 8.85 mmol) and 10% Pd/C (400 mg) in ethyl acetate (40.0 mL) and methanol (10.0 mL) was hydrogenated at room temperature for 72 hours using hydrogen bomb (200 psi). The reaction mixture was filtered through Celite and the Celite was washed with EtOAc/MeOH (1:1, 3×50 mL). The filtrate was concentrated in vacuo to afford tert-butyl-4-(3-amino-4-fluorophenyl)-1-piperidinecarboxylate (2.10 g, 98.0%): $^1$H NMR (400 MHz, CDCl$_3$) δ 6.96-6.76 (m, 1H), 6.67-6.54 (m, 1H), 6.54-6.40 (m, 1H), 4.38-4.09 (br, 2H), 4.09-3.58 (br, 2H), 2.87-2.62 (m, 2H), 2.60-2.39 (m, 1H), 1.85-1.65 (m, 2H), 1.64-1.40 (m, 2H), 1.48 (s, 9H).

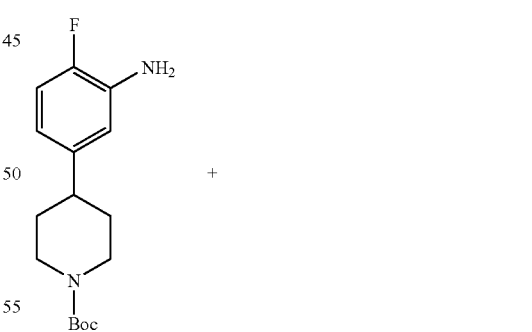

+

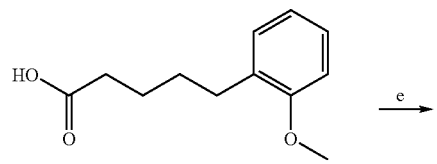

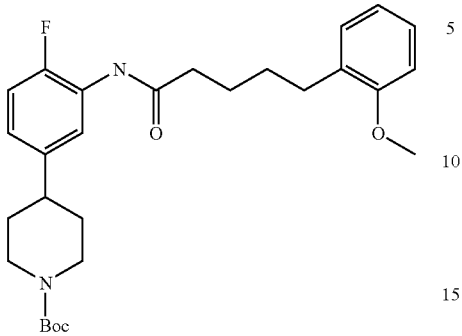

TERT-BUTYL 4-(4-FLUORO-3-{[5-(2-METHOXYPHENYL)PENTANOYL]AMINO}PHENYL)-1-PIPERIDINECARBOXYLATE

A 25-mL RB-flask was charged with 5-(2-methoxyphenyl)pentanoic acid (53.0 mg, 0.250 mmol), tert-butyl-4-(3-amino-4-fluorophenyl)-1-piperidinecarboxylate (59.0 mg, 0.200 mmol), 1-[3-(Dimethylamino)propyl]-3-ethylcarbodiimide hydrochloride (0.400 mmol, 62.0 mg), 4-dimethylaminopyridine (10 mg) in DMF:DCM (0.2:2.0 mL) at room temperature. The reaction mixture was stirred for 12 h and water (10.0 mL) was added to the reaction mixture. The organic layer was separated and the aqueous layer was extracted with CHCl$_3$ (3×10 mL) The combined organic extracts were washed with brine, dried over MgSO$_4$, filtered and concentrated in vacuo. The crude residue was purified by chromatography (silica gel, hexanes:EtOAc 6:1) to afford tert-butyl 4-(4-fluoro-3-{[5-(2-methoxyphenyl)pentanoyl]amino}phenyl)-1-piperidinecarboxylate (48.4 mg, 50.0%): $^1$H NMR (400 MHz, CDCl$_3$) δ 8.36-8.13 (m, 1H), 7.39 (s, 1H), 7.26-7.06 (m, 2H), 7.06-6.92 (m, 1H), 6.92-6.75 (m, 3H), 4.41-4.02 (m, 2H), 3.80 (s, 3H), 2.90-2.70 (m, 2H), 2.70-2.63 (m, 2H), 2.63-2.51 (m, 1H), 2.49-2.32 (m, 2H), 1.87-1.72 (m, 4H), 1.72-1.63 (m, 2H), 1.63-1.52 (m, 2H), 1.48 (s, 9H).

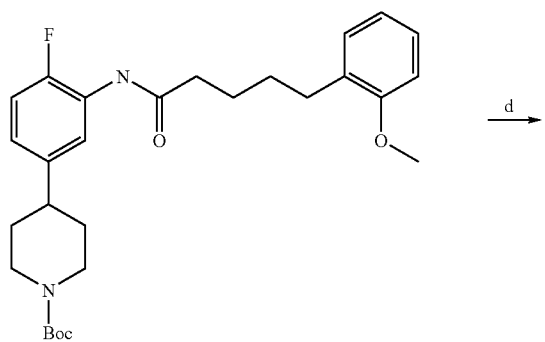

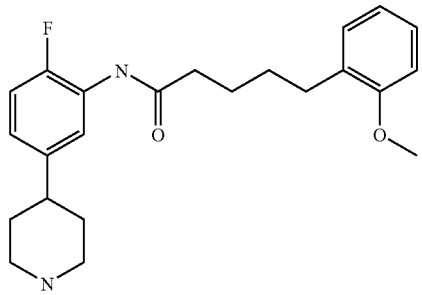

EXAMPLE 10

N-[2-Fluoro-5-(4-Piperidinyl)Phenyl]-5-(2-Methoxyphenyl)Pentanamide

Into a solution of tert-butyl 4-(4-fluoro-3-{[5-(2-methoxyphenyl)pentanoyl]amino}phenyl)-1-piperidinecarboxylate (48.4 mg, 0.100 mmol) in CH$_2$Cl$_2$ (2.0 mL) was added trifluoroacetic acid (114 mg, 1.0 mmol) at room temperature. The reaction mixture was stirred for 30 min and concentrated in vacuo. The residue was dissolved in CHCl$_3$/i-PrOH (3:1, 10 mL) and was basified to pH 11 with 5% KOH solution. The organic layer was separated and the aqueous layer was extracted with CHCl$_3$/i-PrOH (3:1, 3×10 mL). The combined organic extracts were washed with brine, dried over MgSO$_4$, filtered and concentrated in vacuo to afford afford N-[2-fluoro-5-(4-piperidinyl)phenyl]-5-(2-methoxyphenyl)pentanamide (38.0 mg, 95%): $^1$H NMR (400 MHz, CD$_3$OD) δ 8.30-8.12 (m, 1H), 7.64-7.41 (m, 1H), 7.24-7.07 (m, 2H), 7.06-6.92 (m, 1H), 6.92-6.74 (m, 3H), 3.80 (s, 3H), 3.25-3.06 (m, 2H), 2.80-2.49 (m, 5H), 2.48-2.24 (m, 3H), 1.89-1.71 (m, 4H), 1.71-1.46 (m, 4H); ESMS m/e: 385.2 (M+H)$^+$.

3-[4-(3,4-DIFLUOROPHENOXY)PHENYL]PROPANOIC ACID

In a 50-mL RB-flask was added 3-(4-hydroxyphenyl)propionic acid (1.66 g, 10.0 mmol), 3,4-difluoroiodobenzene (2.40 g, 10.0 mmol), copper(I) bromide (0.100 g), potassium carbonate (2.76 g, 20.0 mmol), and n-methyl-2-pyrrolidone (20 mL) as solvent. The mixture was stirred for 5 min at room temperature and then heated to 140° C. (oil bath). After being stirred for 12 hours at 140° C., the reaction mixture was cooled to room temperature and diluted with EtOAC (100 mL). The diluted mixture was washed with citric acid (aq, 30 mL), water (3×50 mL, brine and dried over MgSO$_4$. The removal of solvent in vacuo afforded crude which was purified by chromatography (0.901 g, 32%): $^1$H NMR (400 MHz, CDCl$_3$) δ 11.44-11.06 (br, 1H), 7.24-7.14 (m, 2H), 7.14-7.00 (m, 1H), 7.00-6.86 (m, 2H), 6.86-6.75 (m, 1H), 6.75-6.61 (m, 1H), 2.94 (t, 2H, J=7.6 Hz), 2.68 (t, 2H, J=7.6 Hz); ESMS m/e: 277.2 (M−H$^+$).

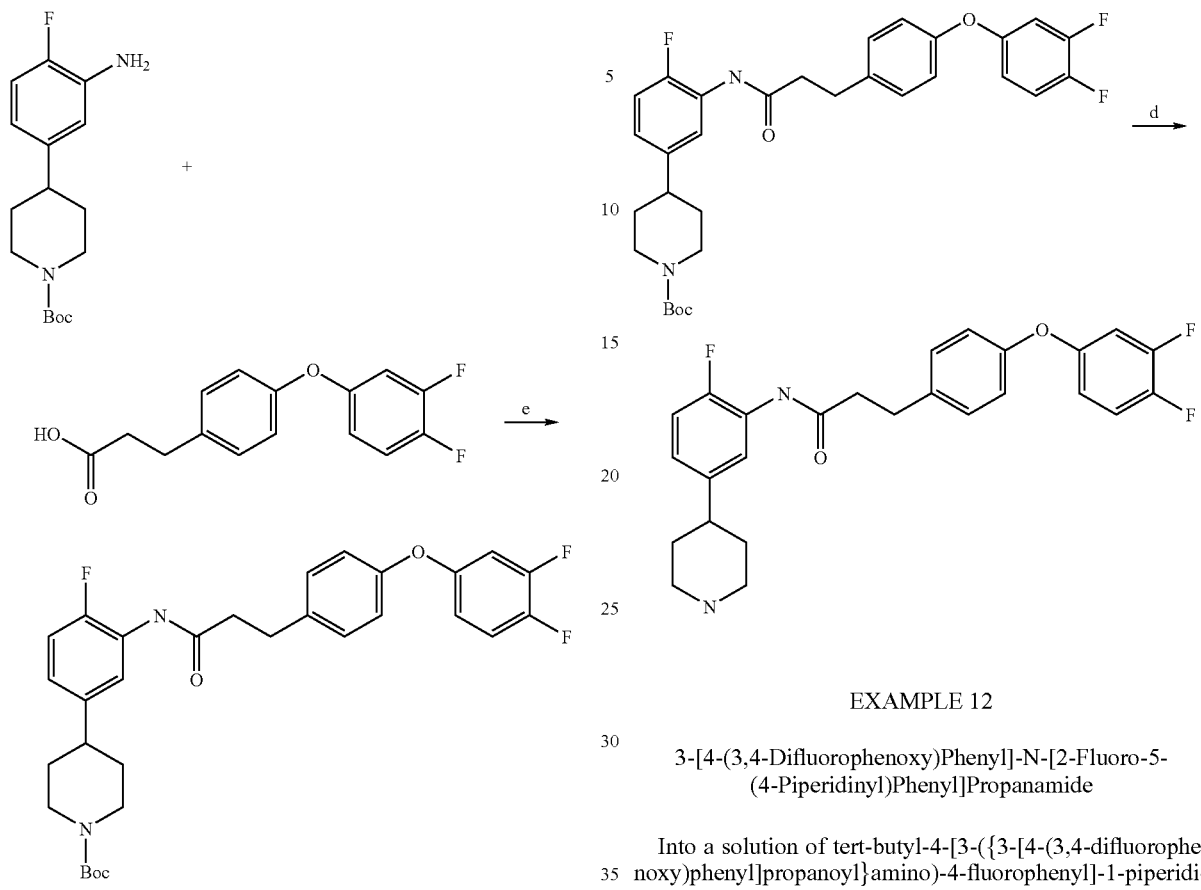

TERT-BUTYL-4-[3-({3-[4-(3,4-DIFLUOROPHE-NOXY)PHENYL]PROPANOYL}AMINO)-4-FLUOROPHENYL]-1-PIPERIDINECARBOXY-LATE

A 25-mL RB-flask was charged with 3-[4-(3,4-difluorophenoxy)phenyl]propanoic acid (180 mg, 0.650 mmol), tert-butyl-4-(3-amino-4-fluorophenyl)-1-piperidine carboxylate (180 mg, 0.610 mmol), 1-[3-(Dimethylamino) propyl]-3-ethylcarbodimide hydrochloride (1.22 mmol, 190 mg), 4-dimethylaminopyridine (20 mg) in DMF:DCM (0.4: 4.0 mL) at room temperature. The reaction mixture was stirred for 12 h and water (10.0 mL) was added to the reaction mixture. The organic layer was separated and the aqueous layer was extracted with CHCl$_3$ (3×10 mL) The combined organic extracts were washed with brine, dried over MgSO$_4$, filtered and concentrated in vacuo. The crude residue was purified by chromatography (silica gel, hexanes:EtOAc 6:1) to afford tert-butyl 4-[3-({3-[4-(3,4-difluorophenoxy)phenyl]propanoyl}amino)-4-fluorophenyl]-1-piperidinecarboxylate (85.0 mg, 25.0%): $^1$H NMR (400 MHz, CDCl$_3$) δ 8.32-8.15 (m, 1H), 7.47-6.45 (m, 10H), 4.41-4.07 (br, 2H), 3.17-2.96 (m, 2H), 2.90-2.67 (m, 4H), 2.67-2.56 (m, 1H), 1.91-1.69 (m, 2H), 1.68-1.48 (m, 2H), 1.47 (s, 9H); ESMS m/e 553.3 (M−H$^+$).

EXAMPLE 12

3-[4-(3,4-Difluorophenoxy)Phenyl]-N-[2-Fluoro-5-(4-Piperidinyl)Phenyl]Propanamide Into a solution of tert-butyl-4-[3-({3-[4-(3,4-difluorophenoxy)phenyl]propanoyl}amino)-4-fluorophenyl]-1-piperidinecarboxylate (85.0 mg, 0.150 mmol) in CH$_2$Cl$_2$ (2.0 mL) was added trifluoroacetic acid (170 mg, 1.50 mmol) at room temperature. The reaction mixture was stirred for 10 min and concentrated in vacuo. The residue was dissolved in CHCl$_3$/i-PrOH (3:1, 10 mL) and was basified to pH 11 with 5% KOH solution. The organic layer was extracted and the aqueous layer was extracted with CHCl$_3$/i-PrOH (3:1, 3×10 mL). The combined organic extracts were washed with brine, dried over MgSO$_4$, filtered and concentrated in vacuo to afford 3-[4-(3,4-difluorophenoxy)phenyl]-N-[2-fluoro-5-(4-piperidinyl)phenyl]propanamide (65.0 mg, 92%): $^1$H NMR (400 MHz, CD$_3$OD) δ 8.27-8.12 (m, 1H), 7.39 (s, 1H), 7.33-7.17 (m, 2H), 7.17-7.06 (m, 1H), 7.06-6.97 (m, 1H), 6.97-6.87 (m, 3H), 6.86-6.74 (m, 1H), 6.74-6.62 (m, 1H), 6.15-5.63 (br, 1H), 3.55-3.31 (m, 2H), 3.15-2.97 (m, 2H), 2.97-2.79 (m, 2H), 2.79-2.59 (m, 3H), 2.05-1.79 (m, 4H); ESMS m/e: 455.2 (M+H)$^+$.

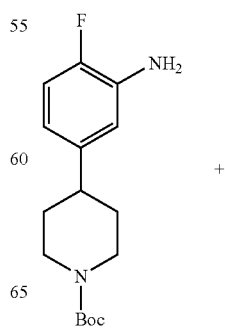

-continued

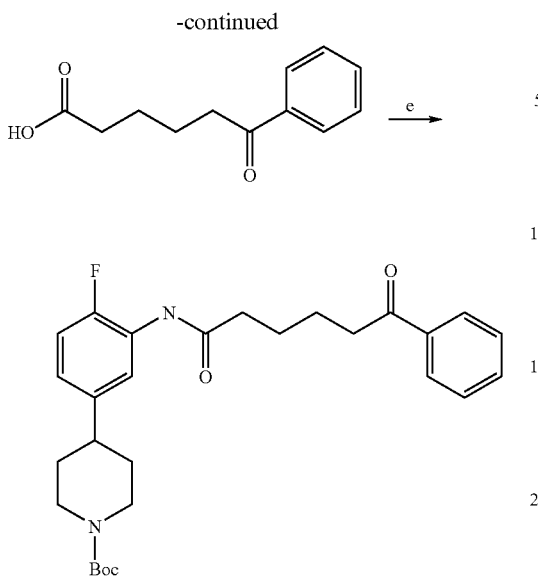

TERT-BUTYL 4-{4-FLUORO-3-[(6-OXO-6-PHE-NYLHEXANOYL)AMINO]PHENYL}-1-PIPERIDINECARBOXYLATE

A 25-mL RB-flask was charged with 6-oxo-6-phenylhexanoic acid (51.0 mg, 0.250 mmol), tert-butyl-4-(3-amino-4-fluorophenyl)-1-piperidinecarboxylate (59.0 mg, 0.200 mmol), 1-[3-(Dimethylamino)propyl]-3-ethylcarbodiimide hydrochloride (0.400 mmol, 62.0 mg), 4-dimethylaminopyridine (10 mg) in DMF:DCM (0.2:2.0 mL) at room temperature. The reaction mixture was stirred for 12 h and water (10.0 mL) was added to the reaction mixture. The organic layer was separated and the aqueous layer was extracted with CHCl₃ (3×10 mL). The combined organic extracts were washed with brine, dried over MgSO₄, filtered and concentrated in vacuo. The crude residue was purified by chromatography (silica gel, hexanes:EtOAc 6:1) to afford tert-butyl 4-{4-fluoro-3-[(6-oxo-6-phenylhexanoyl)amino]phenyl}-1-piperidinecarboxylate (49.0 mg, 51.0%): $^1$H NMR (400 MHz, CDCl₃) δ 8.30-8.14 (m, 1H), 8.04-7.89 (m, 2H), 7.62-7.50 (m, 1H), 7.50-7.37 (m, 3H), 7.09-6.93 (m, 1H), 6.93-6.76 (m, 1H), 4.38-4.01 (br, 2H), 3.13-2.95 (m, 2H), 2.89-2.69 (m, 2H), 2.65-2.54 (m, 1H), 2.54-2.35 (m, 2H), 1.95-1.74 (m, 6H), 1.69-1.48 (m, 2H), 1.47 (s, 9H).

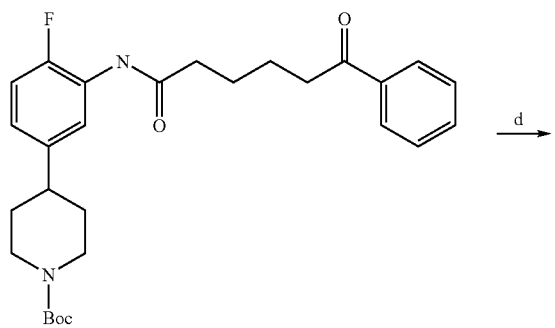

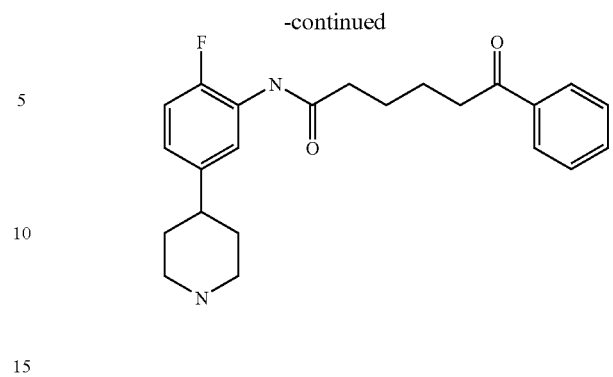

EXAMPLE 9

N-[2-Fluoro-5-(4-Piperidinyl) Phenyl]-6-Oxo-6-Phenylhexanamide

Into a solution of tert-butyl 4-{4-fluoro-3-[(6-oxo-6-phenylhexanoyl)amino]phenyl}-1-piperidine carboxylate (49.0 mg, 0.101 mmol) in CH₂Cl₂ (3.0 mL) was added trifluoroacetic acid (114 mg, 1.01 mmol) at room temperature. The reaction mixture was stirred for 30 min and concentrated in vacuo. The residue was dissolved in CHCl₃/i-PrOH (3:1, 10 mL) and was basified to pH 11 with 5% KOH solution. The organic layer was separated and the aqueous layer was extracted with CHCl₃/i-PrOH (3:1, 3×10 mL). The combined organic extracts were washed with brine, dried over MgSO₄, filtered and concentrated in vacuo to afford N-[2-fluoro-5-(4-piperidinyl)phenyl]-6-oxo-6-phenylhexanamide (35.5 mg, 86.0%). HCl salt: $^1$H NMR (400 MHz, CDCl₃) δ 8.14-8.01 (br, 1H), 8.01-7.89 (m, 2H), 7.65-7.52 (m, 1H), 7.52-7.43 (m, 2H), 7.43-7.26 (br, 1H), 7.13-7.00 (m, 1H), 7.00-6.88 (br, 1H), 3.68-3.43 (m, 2H), 3.19-2.92 (br, 4H), 2.89-2.67 (m, 1H), 2.61-2.36 (br, 2H), 2.26-2.06 (m, 2H), 2.06-1.93 (m, 2H), 1.93-1.71 (br, 4H); ESMS m/e: 383.2 (M+H)⁺.

II. Synthetic Methods for General Structures

The examples described in Section I are merely illustrative of the methods used to synthesize MCH1 antagonists. Further derivatives may be obtained utilizing generalized methods based on the synthetic methods used to synthesize the examples.

It may be necessary to incorporate protection and deprotection strategies for substituents such as amino, amido, carboxylic acid, and hydroxyl groups in the generalized synthetic methods to form further derivatives.

Methods for protection and deprotection of such groups are well-known in the art, and may be found, for example in Green, T. W. and Wuts, P. G. M. (1991) *Protection Groups in Organic Synthesis*, 2$^{nd}$ Edition John Wiley & Sons, New York.

III. Oral Compositions

As a specific embodiment of an oral composition of a compound of this invention, 100 mg of one of the compounds described herein is formulated with sufficient finely divided lactose to provide a total amount of 580 to 590 mg to fill a size O hard gel capsule.

IV. Pharmacological Evaluation of Compounds at Cloned Rat MCH1 Receptor

The pharmacological properties of the compounds of the present invention were evaluated at the cloned rat MCH1 receptor using protocols described below.

Host Cells

A broad variety of host cells can be used to study heterologously expressed proteins. These cells include but are not restricted to assorted mammalian lines such as: Cos-7, CHO, LM(tk-), HEK293, Peak rapid 293, etc.; insect cell lines such as: Sf9, Sf21, etc.; amphibian cells such as xenopus oocytes; and others.

COS 7 cells are grown on 150 mm plates in DMEM with supplements (Dulbecco's Modified Eagle Medium with 10% bovine calf serum, 4 mM glutamine, 100 units/ml penicillin/ 100 Fg/ml streptomycin) at 37° C., 5% $CO_2$. Stock plates of COS-7 cells are trypsinized and split 1:6 every 3-4 days.

Human embryonic kidney 293 cells are grown on 150 mm plates in DMEM with supplements (10% bovine calf serum, 4 mM glutamine, 100 units/ml penicillin/100 Fg/ml streptomycin) at 37° C., 5% $CO_2$. Stock plates of 293 cells are trypsinized and split 1:6 every 3-4 days.

Human embryonic kidney Peak rapid 293 (Peakr293) cells are grown on 150 mm plates in DMEM with supplements (10% fetal bovine serum, 10% L-glutamine, 50 Fg/ml gentamycin) at 37° C., 5% $CO_2$. Stock plates of Peak rapid 293 cells are trypsinized and split 1:12 every 3-4 days.

Mouse fibroblast LM(tk-) cells are grown on 150 mm plates in DMEM with supplements (Dulbecco's Modified Eagle Medium with 10% bovine calf serum, 4 mM glutamine, 100 units/ml penicillin/100 Fg/ml streptomycin) at 37° C., 5% $CO_2$. Stock plates of LM(tk-) cells are trypsinized and split 1:10 every 3-4 days.

Chinese hamster ovary (CHO) cells were grown on 150 mm plates in HAM=s F-12 medium with supplements (10% bovine calf serum, 4 mM L-glutamine and 100 units/ml penicillin/100 Fg/ml streptomycin) at 37° C., 5% $CO_2$. Stock plates of CHO cells are trypsinized and split 1:8 every 3-4 days.

Mouse embryonic fibroblast NIH-3T3 cells are grown on 150 mm plates in Dulbecco=s Modified Eagle Medium (DMEM) with supplements (10% bovine calf serum, 4 mM glutamine, 100 units/ml penicillin/100 Fg/ml streptomycin) at 37° C., 5% $CO_2$. Stock plates of NIH-3T3 cells are trypsinized and split 1:15 every 3-4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

In some cases, cell lines that grow as adherent monolayers can be converted to suspension culture to increase cell yield and provide large batches of uniform assay material for routine receptor screening projects.

Transient Expression

DNA encoding proteins to be studied can be transiently expressed in a variety of mammalian, insect, amphibian and other cell lines by several methods including but not restricted to; calcium phosphate-mediated, DEAE-dextran mediated, Liposomal-mediated, viral-mediated, electroporation-mediated and microinjection delivery. Each of these methods may require optimization of assorted experimental parameters depending on the DNA, cell line, and the type of assay to be subsequently employed.

A typical protocol for the calcium phosphate method as applied to Peak rapid 293 cells is described as follows:

Adherent cells are harvested approximately twenty-four hours before transfection and replated at a density of $3.5 \times 10^6$ cells/dish in a 150 mm tissue culture dish and allowed to incubate over night at 37° C. at 5% $CO_2$. 250 Fl of a mixture of $CaCl_2$ and DNA (15 Fg DNA in 250 mM $CaCl_2$) is added to a 5 ml plastic tube and 500 Fl of 2×HBS (280 mM NaCl, 10 mM KCl, 1.5 mM $Na_2HPO_4$, 12 mM dextrose, 50 mM HEPES) is slowly added with gentle mixing. The mixture is allowed to incubate for 20 minutes at room temperature to allow a DNA precipitate to form. The DNA precipitate mixture is then added to the culture medium in each plate and incubated for 5 hours at 37° C., 5% $CO_2$. After the incubation, 5 ml of culture medium (DMEM, 10% FBS, 10% L-glut and 50 μg/ml gentamycin) is added to each plate. The cells are then incubated for 24 to 48 hours at 37° C., 5% $CO_2$.

A typical protocol for the DEAE-dextran method as applied to Cos-7 cells is described as follows; Cells to be used for transfection are split 24 hours prior to the transfection to provide flasks which are 70-80% confluent at the time of transfection. Briefly, 8 Fg of receptor DNA plus 8 Fg of any additional DNA needed (e.g. $G_\alpha$ protein expression vector, reporter construct, antibiotic resistance marker, mock vector, etc.) are added to 9 ml of complete DMEM plus DEAE-dextran mixture (10 mg/ml in PBS).

Cos-7 cells plated into a T225 flask (sub-confluent) are washed once with PBS and the DNA mixture is added to each flask. The cells are allowed to incubate for 30 minutes at 37° C., 5% $CO_2$. Following the incubation, 36 ml of complete DMEM with 80 FM chloroquine is added to each flask and allowed to incubate an additional 3 hours. The medium is then aspirated and 24 ml of complete medium containing 10% DMSO for exactly 2 minutes and then aspirated. The cells are then washed 2 times with PBS and 30 ml of complete DMEM added to each flask. The cells are then allowed to incubate over night. The next day the cells are harvested by trypsinization and reseeded as needed depending upon the type of assay to be performed.

A typical protocol for liposomal-mediated transfection as applied to CHO cells is described as follows; Cells to be used for transfection are split 24 hours prior to the transfection to provide flasks which are 70-80% confluent at the time of transfection. A total of 10 Fg of DNA which may include varying ratios of receptor DNA plus any additional DNA needed (e.g. $G_\alpha$ protein expression vector, reporter construct, antibiotic resistance marker, mock vector, etc.) is used to transfect each 75 $cm^2$ flask of cells. Liposomal mediated transfection is carried out according to the manufacturer=s recommendations (LipofectAMINE, GibcoBRL, Bethesda, Md.). Transfected cells are harvested 24 hours post transfection and used or reseeded according the requirements of the assay to be employed.

A typical protocol for the electroporation method as applied to Cos-7 cells is described as follows; Cells to be used for transfection are split 24 hours prior to the transfection to provide flasks which are subconfluent at the time of transfection. The cells are harvested by trypsinization resuspended in their growth media and counted. $4 \times 10^6$ cells are suspended in 300 Fl of DMEM and placed into an electroporation cuvette. 8 Fg of receptor DNA plus 8 Fg of any additional DNA needed (e.g. $G_\alpha$ protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 FF capacitance). Following the pulse, 800 Fl of complete DMEM is added to each cuvette and the suspension transferred to a sterile tube.

Complete medium is added to each tube to bring the final cell concentration to $1 \times 10^5$ cells/100 Fl. The cells are then plated as needed depending upon the type of assay to be performed.

A typical protocol for viral mediated expression of heterologous proteins is described as follows for baculovirus infection of insect Sf9 cells. The coding region of DNA encoding the receptor disclosed herein may be subcloned into pBlueBacIII into existing restriction sites or sites engineered into sequences 5' and 3' to the coding region of the polypeptides. To generate baculovirus, 0.5 Fg of viral DNA (BaculoGold) and 3 Fg of DNA construct encoding a polypeptide may be co-transfected into 2×10$^6$ *Spodoptera frugiperda* insect Sf9 cells by the calcium phosphate co-precipitation method, as outlined in by Pharmingen (in "Baculovirus Expression Vector System: Procedures and Methods Manual"). The cells then are incubated for 5 days at 27° C. The supernatant of the co-transfection plate may be collected by centrifugation and the recombinant virus plaque purified. The procedure to infect cells with virus, to prepare stocks of virus and to titer the virus stocks are as described in Pharmingen=s manual. Similar principals would in general apply to mammalian cell expression via retro-viruses, Simliki forest virus and double stranded DNA viruses such as adeno-, herpes-, and vacinia-viruses, and the like.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the heterologous DNA. An assortment of resistance genes are available including but not restricted to Neomycin, Kanamycin, and Hygromycin. For the purposes of receptor studies, stable expression of a heterologous receptor protein is carried out in, but not necessarily restricted to, mammalian cells including, CHO, HEK293, LM(tk-), etc.

Cell Membrane Preparation

For binding assays, pellets of transfected cells are suspended in ice-cold buffer (20 mM Tris.HCl, 5 mM EDTA, pH 7.4) and homogenized by sonication for 7 sec. The cell lysates are centrifuged at 200×g for 5 min at 4° C. The supernatants are then centrifuged at 40,000×g for 20 min at 4° C. The resulting pellets are washed once in the homogenization buffer and suspended in binding buffer (see methods for radioligand binding). Protein concentrations are determined by the method of Bradford (1976) using bovine serum albumin as the standard. Binding assays are usually performed immediately, however it is possible to prepare membranes in batch and store frozen in liquid nitrogen for future use.

Radioligand Binding Assays

Radioligand binding assays for the rat MCH1 receptor were carried out using plasmid pcDNA3.1-rMCH1-f (ATCC Patent Deposit Designation No. PTA-3505). Plasmid pcDNA3.1-rMCH1-f comprises the regulatory elements necessary for expression of DNA in a mammalian cell operatively linked to DNA encoding the rat MCH1 receptor so as to permit expression thereof. Plasmid pcDNA3.1-rMCH1-f was deposited on Jul. 5, 2001, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Patent Deposit Designation No. PTA-3505.

Binding assays can also be performed as described hereinafter using plasmid pEXJ.HR-TL231 (ATCC Accession No. 203197) Plasmid pEXJ.HR-TL231 encodes the human MCH1 receptor and was deposited on Sep. 17, 1998, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 203197.

Human embryonic kidney Peak rapid 293 cells (Peakr293 cells) were transiently transfected with DNA encoding the MCH1 receptor utilizing the calcium phosphate method and cell membranes were prepared as described above. Binding experiments with membranes from Peakr293 cells transfected with the rat MCH1 receptor were performed with 0.08 nM [$^3$H]Compound A (custom labeled by Amersham) (the synthesis of Compound A is described in detail below) using an incubation buffer consisting of 50 mM Tris pH 7.4, 10 mM MgCl$_2$, 0.16 mM PMSF, 1 mM 1,10 phenantroline and 0.2% BSA. Binding was performed at 25° C. for 90 minutes. Incubations were terminated by rapid vacuum filtration over GF/C glass fiber filters, presoaked in 5% PEI using 50 nM Tris pH 7.4 as wash buffer. In all experiments, nonspecific binding is defined using 10 FM Compound A.

Functional Assays

Cells may be screened for the presence of endogenous mammalian receptor using functional assays. Cells with no or a low level of endogenous receptor present may be transfected with the exogenous receptor for use in functional assays.

A wide spectrum of assays can be employed to screen for receptor activation. These range from traditional measurements of phosphatidyl inositol, cAMP, Ca$^{++}$, and K$^+$, for example; to systems measuring these same second messengers but which have been modified or adapted to be higher throughput, more generic, and more sensitive; to cell based platforms reporting more general cellular events resulting from receptor activation such as metabolic changes, differentiation, and cell division/proliferation, for example; to high level organism assays which monitor complex physiological or behavioral changes thought to be involved with receptor activation including cardiovascular, analgesic, orexigenic, anxiolytic, and sedation effects, for example.

Radioligand Binding Assay Results

The compounds described above were assayed using cloned rat MCH1. The binding affinities of the compounds are shown in Table I.

V. Synthesis of Compound A

Described below is the synthesis of Compound A. Compound A is the radiolabeled compound that was used in the radioligand binding assays described above.

N-[3-(1,2,3,6-TETRAHYDRO-4-PYRIDINYL) PHENYL]ACETAMIDE

The reaction of saturated of aqueous Na$_2$CO$_3$ solution (25 mL), tert-butyl 4-{[(trifluoromethyl)sulfonyl]oxy}-1,2,3,6-tetra hydro-1-pyridine-carboxylate (20 mmol), 3-acetamidophenyl boronic acid (30 mmol) and tetrakis-triphenylphosphine palladium (0) (1.15 g) in dimethoxyethane (40 mL) at reflux temperature overnight gave tert-butyl 4-[3-(acetylamino)phenyl]-3,6-dihydro-1(2H)-pyridinecarboxylate. Deprotection of the BOC group using HCl in dioxane followed by basification (pH 11-12) gave the desired product.

TERT-BUTYL N-(3-BROMOPROPYL)CARBAMATE was prepared from 3-bromopropylamine hydrobromide and BOC$_2$O in the presence of base in dichloromethane.

N-{3-[1-(3-AMINOPROPYL)-1,2,3,6-TETRAHYDRO-4-PYRIDINYL]PHENYL}ACETAMIDE

The reaction of tert-butyl N-(3-bromopropyl)carbamate and N-[3-(1,2,3,6-tetrahydro-4-pyridinyl)phenyl]acetamide in refluxing dioxane with catalytic Bu$_4$NI and base as described in Scheme A gave tert-butyl 3-(4-[3-(acetylamino)phenyl]-3,6-dihydro-1(2H)-pyridinyl)propylcarbamate. Deprotection of the BOC group using HCl in dioxane followed by basification (pH 11-12) gave the desired product.

METHYL (4S)-3-({[3-(4-[3-(ACETYLAMINO)PHENYL]-3,6-DIHYDRO-1(2H)-PYRIDINYL)PROPYL]AMINO}CARBONYL)-4-(3,4-DIFLUOROPHENYL)6-(METHOXYMETHYL)-2-OXO-1,2,3,4-TETRAHYDRO-5-PYRIMIDINE CARBOXYLATE

Prepared from the reaction of 5-methyl 1-(4-nitrophenyl) (6S)-6-(3,4-difluorophenyl)-4-(methoxymethyl)-2-oxo-3,6-dihydro-1,5(2H)-pyrimidinedicarboxylate (describe in PCT Publication No. WO 00/37026, published Jun. 29, 2000) and N-{3-[1-(3-aminopropyl)-1,2,3,6-tetrahydro-4-pyridinyl]phenyl}acetamide: $^1$H NMR δ 8.90 (t, 1H, J=3.6 Hz), 7.75 (s, 1H), 7.50-7.00 (m, 8H), 6.68 (s, 1H), 6.03 (br s, 1H), 4.67 (s, 2H), 3.71 (s, 3H), 3.47 (s, 3H), 3.38 (ABm, 2H), 3.16 (m, 2H), 2.71 (t, 2H, J=5.4 Hz), 2.56 (m, 4H), 2.35-1.90 (br, 2H), 2.17 (s, 3H), 1.82 (p, 2H, J=7.2 Hz); ESMS, 612.25 (M+H)$^+$.

TRITIATED METHYL (4S)-3-{[(3-{4-[3-(ACETYLAMINO)PHENYL]-1-PIPERIDINYL}PROPYL)AMINO]CARBONYL}-4-(3,4-DIFLUOROPHENYL)-6-(METHOXYMETHYL)-2-OXO-1,2,3,4-TETRAHYDRO-5-PYRIMIDINECARBOXYLATE

Methyl (4S)-3-({[3-(4-[3-(acetylamino)phenyl]-3,6-dihydro-1(2H)-pyridinyl)propyl]amino}carbonyl)-4-(3,4-difluorophenyl)-6-(methoxymethyl)-2-oxo-1,2,3,4-tetrahydro-5-pyrimidine carboxylate was tritiated (Amersham) using the described cold method (H$_2$, balloon method, Methanol, Pd/C, overnight) to give the tritiated methyl (4S)-3-{[(3-{4-[3-(acetylamino)phenyl]-1-piperidinyl}propyl)amino]carbonyl}-4-(3,4-difluorophenyl)-6-(methoxymethyl)-2-oxo-1,2,3,4-tetrahydro-5-pyrimidinecarboxylate ((+)–isomer), which in turn, was used as a radioligand in the MCH pharmacological assays.

TABLE I

| Example No. | Structure | Ki (nM) |
|---|---|---|
| 1 | 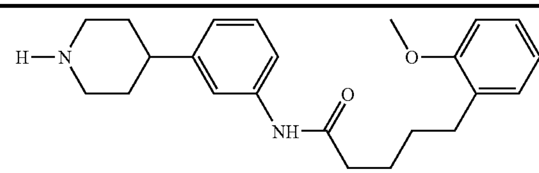 | 79.6 |
| 2 | 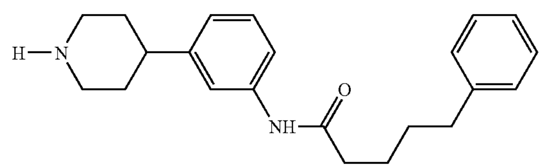 | 197 |
| 3 | 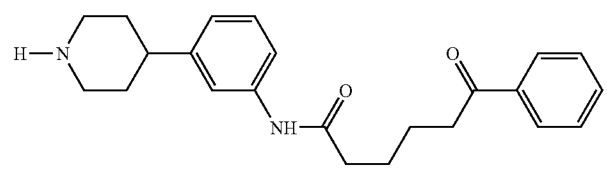 | 1104 |
| 4 | 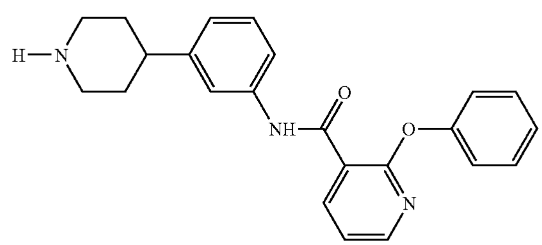 | 353 |
| 5 | 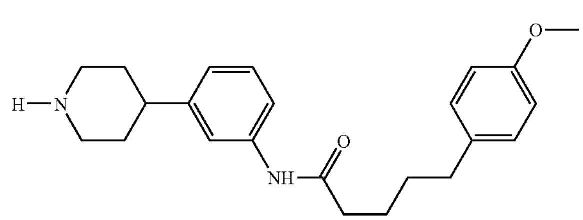 | 476 |

TABLE I-continued

| Example No. | Structure | Ki (nM) |
|---|---|---|
| 6 | 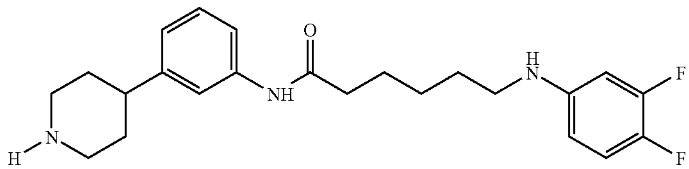 | 438 |
| 7 | 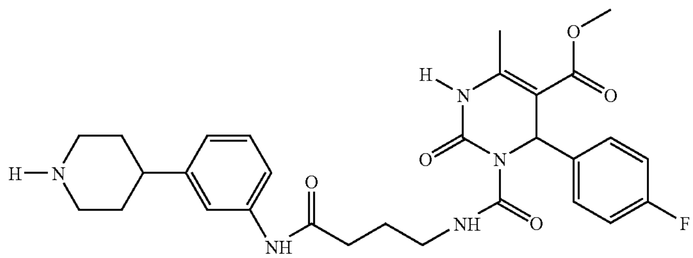 | 142 |
| 8 | 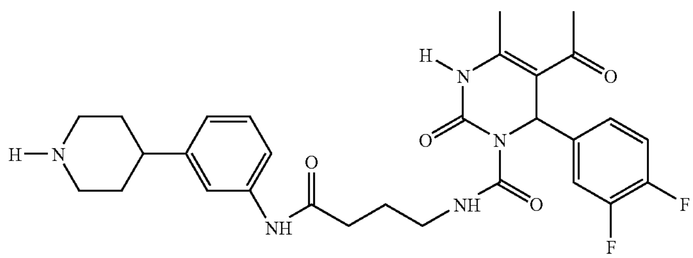 | 181 |
| 9 | 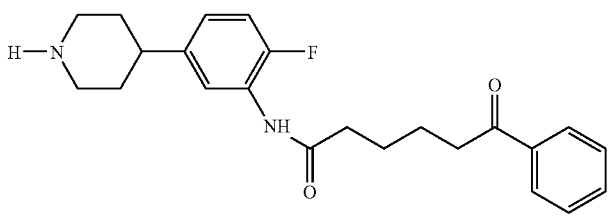 | 313 |
| 10 | 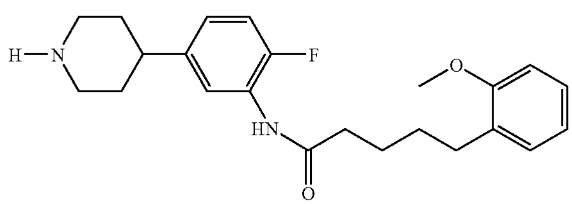 | 20.9 |
| 11 | 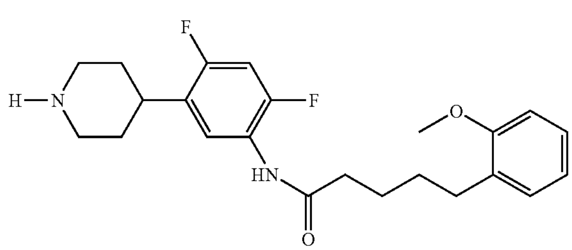 | 46.6 |

TABLE I-continued

| Example No. | Structure | Ki (nM) |
|---|---|---|
| 12 | 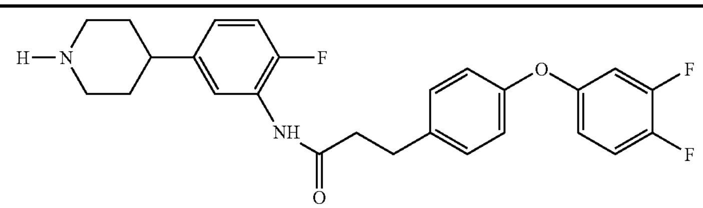 | 33.8 |

VI. In-Vivo Methods

The following in vivo methods are performed to predict the efficacy of MCH1 antagonists for the treatment of obesity (3-day body weight and sweetened condensed milk), depression (forced swim test), anxiety (social interaction test), and urinary disorders (DIRC and CSTI).

Effects of MCH1 Antagonists on Body Weight (3 Day)

Male Long Evans rats (Charles River) weighing 180-200 grams are housed in groups of four on a 12 hour light/dark cycle with free access to food and water. Test compounds are administered twice daily via i.p. injection, 1 hour before the dark cycle and 2 hours after lights on, for three days. All rats are weighed daily after each morning injection. Overall results are expressed as body weight (grams) gained per day (mean±SEM) and are analyzed by two-way ANOVA. Data for each time point are analyzed by one-way ANOVA followed by post hoc Newman-Keuls test. The data are analyzed using the GraphPad Prism (v2.01) (GraphPad Software, Inc., San Diego, Calif.). All data are presented as means±S.E.M.

Effects of MCH1 Antagonists on Consumption of Sweetened Condensed Milk

Male C57BL/6 mice (Charles River) weighing 17-19 grams at the start of experiments are housed in groups of four or five on a 12 hour light/dark cycle with free access to food and water. For 7 days, mice are weighed, placed in individual cages and allowed to drink sweetened condensed milk (Nestle, diluted 1:3 with water) for 1 hour, 2-4 hours into the light cycle. The amount of milk consumed is determined by weighing the milk bottle before and after each drinking bout. On the test day, mice received i.p. injections of Test Compound (3, 10 or 30 mg/kg in 0.01% lactic acid), vehicle (0.01% lactic acid) of d-fenfluramine (10 mg/kg in 0.01% lactic acid) 30 min. prior to exposure to milk. The amount of milk consumed on the test day (in mls milk/kg body weight) is compared to the baseline consumption for each mouse determined on the previous 2 days. Data for each time point are analyzed by one-way ANOVA.

Forced Swim Test (FST) in the Rat

Animals

Male Sprague-Dawley rats (Taconic Farms, N.Y.) are used in all experiments. Rats are housed 5 per cage and maintained on a 12:12-h light-dark cycle. Rats are handled for 1 minutes each day for 4 days prior to behavioral testing.

Drug Administration

Animals are randomly assigned to receive a single i.p. administration of vehicle (2.5% EtOH/2.5% Tween-80), imipramine (positive control; 60 mg/kg), or Test Compound 60 minutes before the start of the 5 minute test period. All injections are given using 1 cc tuberculin syringe with 26⅜ gauge needles (Becton-Dickinson, VWR Scientific, Bridgeport, N.J.). The volume of injection is 1 ml/kg.

Experimental Design

The procedure used in this study is similar to that previously described (Porsolt, et al., 1978), except the water depth is 31 cm in this procedure. The greater depth in this test prevents the rats from supporting themselves by touching the bottom of the cylinder with their feet.

Swim sessions are conducted by placing rats in individual plexiglass cylinders (46 cm tall×20 cm in diameter) containing 23-25° C. water 31 cm deep. Swim tests are conducted always between 900 and 1700 hours and consisted of an initial 15-min conditioning test followed 24 h later by a 5-minute test. Drug treatments are administered 60 minutes before the 5-minute test period. Following all swim sessions, rats are removed from the cylinders, dried with paper towels and placed in a heated cage for 15 minutes and returned to their home cages. All test sessions are videotaped using a color video camera and recorded for scoring later.

Behavioral Scoring

The rat's behavior is rated at 5 second intervals during the 5 minute test by a single individual, who is blind to the treatment condition. Scored behaviors are:

1. Immobility—rat remains floating in the water without struggling and is only making those movements necessary to keep its head above water;
2. Climbing—rat is making active movements with its forepaws in and out of the water, usually directed against the walls;
3. Swimming—rat is making active swimming motions, more than necessary to merely maintain its head above water, e.g. moving around in the cylinder; and
4. Diving—entire body of the rat is submerged.

Data Analysis

The forced swim test data (immobility, swimming, climbing, diving) are subjected to a randomized, one-way ANOVA and post hoc tests conducted using the Newman-Keuls test. The data are analyzed using the GpraphPad Prism (v2.01) (GraphPad Software, Inc., San Diego, Calif.). All data are presented as means±S.E.M. All data are presented as means±S.E.M.

Forced Swim Test (FST) in the Mouse

Animals

DBA/2 mice (Taconic Farms, N.Y.) are used in all experiments. Animals are housed 5 per cage in a controlled environment under a 12:12 hour light:dark cycle. Animals are handled 1 min each day for 4 days prior to the experiment. This procedure included a mock gavage with a 1.5 inch feeding tube.

Drug Administration

Animals are randomly assigned to receive a single administration of vehicle (5% EtOH/5% Tween-80), Test Compound, or imipramine (60 mg/kg) by oral gavage 1 hour before the swim test.

Experimental Design

The procedure for the forced swim test in the mouse is similar to that described above for the rat, with some modifications. The cylinder used for the test is a 1 liter beaker (10.5 cm diameter×15 cm height) fill to 800 ml (10 cm depth) of 23-25° C. water. Only one 5-minute swim test is conducted for each mouse, between 1300 and 1700 hours. Drug treatments are administered 30-60 minutes before the 5-minute test period. Following all swim sessions, mice are removed from the cylinders, dried with paper towels and placed in a heated cage for 15 minutes. All test sessions are videotaped using a Sony color video camera and recorder for scoring later.

Behavorial Scoring

The behavior during minutes 2-5 of the test is played back on a TV monitor and scored by the investigator. The total time spent immobile (animal floating with only minimal movements to remain afloat) and mobile (swimming and movements beyond those required to remain afloat) are recorded.

Data Analysis

The forced swim test data (time exhibiting immobility, mobility; seconds) are subjected to a randomized, one-way ANOVA and post hoc tests conducted using the Newman-Keuls test. The data are analyzed using the GraphPad Prism (v2.01) (GraphPad Software, Inc., San Diego, Calif.). All data are presented as means±S.E.M.

Social Interaction Test (SIT)

Rats are allowed to acclimate to the animal care facility for 5 days and are housed singly for 5 days prior to testing. Animals are handled for 5 minutes per day. The design and procedure for the Social Interaction Test is carried out as previously described by Kennett, et al. (1997). On the test day, weight matched pairs of rats (±5%), unfamiliar to each other, are given identical treatments and returned to their home cages. Animals are randomly divided into 5 treatment groups, with 5 pairs per group, and are given one of the following i.p. treatments: Test Compound (10, 30 or 100 mg/kg), vehicle (1 ml/kg) or chlordiazepoxide (5 mg/kg). Dosing is 1 hour prior to testing. Rats are subsequently placed in a white perspex test box or arena (54×37×26 cm), whose floor is divided up into 24 equal squares, for 15 minutes. An air conditioner is used to generate background noise and to keep the room at approximately 74° F. All sessions are videotaped using a JVC camcorder (model GR-SZ1, Elmwood Park, N.J.) with either TDK (HG ultimate brand) or Sony 30 minute videocassettes. All sessions are conducted between 1300-1630 hours. Active social interaction, defined as grooming, sniffing, biting, boxing, wrestling, following and crawling over or under, is scored using a stopwatch (Sportsline model no. 226, 1/100 sec. discriminability). The number of episodes of rearing (animal completely raises up its body on its hind limbs), grooming (licking, biting, scratching of body), and face ishing (i.e. hands are moved repeatedly over face), and number of squares crossed are scored. Passive social interaction (animals are lying beside or on top of each other) is not scored. All behaviors are assessed later by an observer who is blind as to the treatment of each pair. At the end of each test, the box is thoroughly wiped with moistened paper towels.

Animals

Male albino Sprague-Dawley rats (Taconic Farms, N.Y.) are housed in pairs under a 12 hr light dark cycle (lights on at 0700 hrs.) with free access to food and water.

Drug Administration

Test Compound is dissolved in 100% DMSO or 5% lactic acid, v/v (Sigma Chemical Co., St. Louis, Mo.). Chlordiazepoxide (Sigma Chemical Co., St. Louis, Mo.) is dissolved in double distilled water. The vehicle consists of 50% DMSO (v/v) or 100% dimethylacetamide (DMA). All drug solutions are made up 10 minutes prior to injection and the solutions are discarded at the end of the test day. The volume of drug solution administered is 1 ml/kg.

Data Analysis

The social interaction data (time interacting, rearing and squares crossed) are subjected to a randomized, one-way ANOVA and post hoc tests conducted using the Student-Newman-Keuls test. The data are subjected to a test of normality (Shapiro-Wilk test). The data are analyzed using the GBSTAT program, version 6.5 (Dynamics Microsystems, Inc., Silver Spring, Md., 1997). All data are presented as means ∀ S.E.M.

In Vivo Models of the Micturition Reflex

The effects of compounds on the micturition reflex are assessed in the "distension-induced rhythmic contraction" (DIRC), as described in previous publications (e.g. Maggi et al, 1987; Morikawa et al, 1992), and Continuous Slow Transvesicular Infusion (CSTI) models in rats.

DIRC Model

Female Sprague Dawley rats weighing approximately 300 g are anesthetized with subcutaneous urethane (1.2 g/kg). The trachea is cannulated with PE240 tubing to provide a clear airway throughout the experiment. A midline abdominal incision is made and the left and right ureters are isolated. The ureters are ligated distally (to prevent escape of fluids from the bladder) and cannulated proximally with PE10 tubing. The incision is closed using 4-0 silk sutures, leaving the PE10 lines routed to the exterior for the elimination of urine. The bladder is canulated via the transurethral route using PE50 tubing inserted 2.5 cm beyond the urethral opening. This cannula is secured to the tail using tape and connected to a pressure transducer. To prevent leakage from the bladder, the cannula is tied tightly to the exterior urethral opening using 4-0 silk.

To initiate the micturition reflex, the bladder is first emptied by applying pressure to the lower abdomen, and then filled with normal saline in 100 increments (maximum=2 ml) until spontaneous bladder contractions occurred (typically 20-40 mmHg at a rate of one contraction every 2 to 3 minutes. Once a regular rhythm is established, vehicle (saline) or Test Compounds are administered i.v. or i.p. to explore their effects on bladder activity. The $5\text{-}HT_{1A}$ antagonist WAY-100635 is given as a positive control. Data are expressed as contraction interval (in seconds) before drug application (basal), or after the application of vehicle or test article.

Continuous Slow Transvesicular Infusion (CSTI) Rat Model

Male Sprague Dawley rats weighing approximately 300 g are used for the study. Rats are anaesthetized with pentobarbitone sodium (50 mg/kg, i.p). Through a median abdominal incision, bladder is exposed and a polyethylene cannula (PE 50) is introduced into the bladder through a small cut on the dome of the bladder and the cannula is secured with a purse string suture. The other end of the cannula is exteriorized subcutaneously at the dorsal neck area. Similarly, another cannula (PE 50) is introduced into the stomach through a paramedian abdominal incision with the free end exteriorized subcutaneously to the neck region. The surgical wounds are closed with silk 4-0 suture and the animal is allowed to recover with appropriate post surgical care. On the following day, the animal is placed in a rat restrainer. The open end of the bladder-cannula is connected to a pressure transducer as well as infusion pump through a three-way stopcock. The bladder voiding cycles are initiated by continuous infusion of normal saline at the rate of 100 µl/min. The repetitive voiding contractions are recorded on a Power Lab on-line data acquisition software. After an recording the basal voiding pattern for an hour, the test drug or vehicle is administered directly into stomach through the intragastric catheter and the voiding cycles are monitored for 5 hours. Micturition pressure and frequency are calculated before and after the treatment (at every 30 min interval) for each animal. Bladder capacity is calculated from the frequency, based on the constant infusion of 100 ul/min micturition. The effect of the test drug is expressed as a percentage of basal, pre-drug bladder capacity. WAY 100635 is used as positive control for comparison.

REFERENCES

Auburger, G., et al., (1992) Assignment of the second (cuban) locus of autosomal dominant cerebellar ataxia to chromosome 12q23-24.1, between flanking markers D12S58 and PLA2. *Cytogenet. Cell. Genet.* 61:252-256.

Bahjaoui-Bouhaddi, M., et al., (1994) Insulin treatment stimulates the rat melanin-concentrating hormone-producing neurons. *Neuropeptides* 24:251-258.

Baker, B. I. (1991) Melanin-concentrating hormone: a general vertebrate neuropeptide. *Int. Rev. Cytol.* 126:1-47.

Baker, B. I. (1994) Melanin-concentrating hormone update: functional consideration. *TEM* 5:120-126.

Bassett, A. S., et al., (1988) Partial trisomy chromosome 5 cosegregating with schizophrenia. *Lancet* 1:799-801.

Bednarek, M. A., et al. "Synthesis and biological evaluation in vitro of a selective, high potency peptide agonist of human melanin-concentrating hormone action at human melanin-concentrating hormone receptor 1" *J Biol Chem* 277 (16): 13821-13826 (2002).

Bittencourt, J. C., et al., (1992) The melanin-concentrating hormone system of the rat brain: An immuno- and hybridization histochemical characterization. *J. Comp. Neurol.* 319:218-245.

Borowsky, B., et al., *Nature Medicine*, 2003.

Bradford, M. M. (1976) A rapid and sensitive method for the quantitation of microgram quantities of protein utilizing the principle or protein-dye binding. *Anal. Biochem.* 72: 248-254.

Burgaud, J. L., et al., (1997) Melanin-concentrating hormone binding sites in human SVK14 keratinocytes. *Biochem. Biophys. Res. Commun.* 241 (3):622-629.

Chambers, J., et al., "Melanin-concentrating hormone is the cognate ligand for the orphan G-protein-coupled receptor SLC-1" *Nature* 400 (6741): 261-6 (1999).

Chen, Y., et al, "Targeted disruption of the melanin-concentrating hormone receptor-1 results in hyperphagia and resistance to diet-induced obesity" *Endocrinology* 143 (7): 2469-2477 (2002).

Craddock, N., et al., (1993) The gene for Darier=s disease maps to chromosome 12q23-q24.1. *Hum. Mol. Genet.* 2:1941-1943.

Dondoni, A., et al., (1995) *T. Synthesis*, 181.

Drozdz, R. and Eberle, A. N. (1995) Binding sites for melanin-concentrating hormone (MCH) in brain synaptosomes and membranes from peripheral tissues identified with highly tritiated MCH. *J. Recept. Signal. Transduct. Res.* 15 (1-4):487-502.

Drozdz, R., et al., (1995) Melanin-concentrating hormone binding to mouse melanoma cells in vitro. *FEBS* 359:199-202.

Drozdz, R., et al., (1998) Characterization of the receptor for melanin-concentrating hormone on melanoma cells by photocrosslinking. *Ann. NY Acad. Sci.* 839 (1):210-213.

Gilliam, T. C., et al., (1989) Deletion mapping of DNA markers to a region of chromosome 5 that cosegregates with schizophrenia. *Genomics* 5:940-944.

Gonzalez, M. I., et al., (1997) Stimulatory effect of melanin-concentrating hormone on luteinizing hormone release. *Neuroendocrinology* 66 (4):254-262.

Gonzalez, M. I., et al., (1996) Behavioral effects of α-melanocyte-stimulating hormone (α-MSH) and melanin-concentrating hormone (MCH) after central administration in female rats. *Peptides* 17:171-177.

Grillon, S., et al., (1997) Exploring the expression of the melanin-concentrating hormone messenger RNA in the rat lateral hypothalamus after goldthioglucose injection. *Neuropeptides* 31 (2):131-136.

Herve, C. and Fellmann, D. (1997) Changes in rat melanin-concentrating hormone and dynorphin messenger ribonucleic acids induced by food deprivation. *Neuropeptides* 31 (3):237-242.

Hervieu, G., et al., (1996) Development and stage-dependent expression of melanin-concentrating hormone in mammalian germ cells. *Biology of Reproduction* 54:1161-1172.

Kauwachi, H., et al., (1983) Characterization of melanin-concentrating hormone in chum salmon pituitaries. *Nature* 305:321-333.

Knigge, K. M., et al., (1996) Melanotropic peptides in the mammalian brain: The melanin-concentrating hormone. *Peptides* 17:1063-1073.

Knigge, K. M. and Wagner, J. E. (1997) Melanin-concentrating hormone (MCH) involvement in pentylenetetrazole (PTZ)-induced seizure in rat and guinea pig. *Peptides* 18 (7):1095-1097.

Lakaye, B., et al., "Cloning of the rat brain cDNA encoding for the SLC-1 G protein-coupled receptor reveals the presence of an intron in the gene" *Biochem Biophys Acta* 1401 (2): 216-220 (1998).

Ludwig, D. S., et al., (1998) Melanin-concentrating hormone: a functional melanocortin antagonist in the hypothalamus. *Am. J. Physiol. Endocrinol. Metab.* 274 (4):E627-E633.

MacKenzie, F. J., et al., (1984) Evidence that the dopaminergic incerto-hypothalamic tract has a stimulatory effect on ovulation and gonadotropin release. *Neuroendocrinology* 39:289-295.

Maggi, C. A., et al., "Spinal and supraspinal components of GABAergic inhibition of the micturition reflex in rats." *J Pharmacol Exp Ther* 240: 998-1005 (1987).

Marsh, D. J., et al, "Melanin-concentrating hormone 1 receptor-deficient mice are lean, hyperactive, and hyperphagic and have altered metabolism" *Proc Natl Acad Sci USA* 99 (5): 3240-3245 (2002).

Martin, R., et al., (1997) *J. Tetrahedron Letters*, 38, 1633.

McBride, R. B., et al., (1994) The actions of melanin-concentrating hormone (MCH) on passive avoidance in rats: A preliminary study. *Peptides* 15:757-759.

Melki, J., et al., (1990) Gene for chronic proximal spinal muscular atrophies maps to chromosome 5q. *Nature* (London) 344:767-768. tk Miller, C. L., et al., (1993) α-MSH and MCH are functional antagonists in a CNS auditory paradigm. *Peptides* 14:1-10.

Morikawa, K., et al., "Inhibitory effect of inaperisone hydrochloride (inaperisone), a new centrally acting muscle relaxant, on the micturition reflex." *Eur J Pharmacol* 213: 409-415 (1992).

Nahon, J-L. (1994) The melanin-concentrating hormone: from the peptide to the gene. *Critical Rev. in Neurobiol* 221:221-262.

Parkes, D. G. (1996) Diuretic and natriuretic actions of melanin concentrating hormone in conscious sheep. *J. Neuroendocrinol.* 8:57-63.

Pedeutour, F., et al., (1994) Assignment of the human pro-melanin-concentrating hormone gene (PMCH) to chromosome 12q23-24 and two variant genes (PMCHL1 and PMCHL2) to chromosome 5 p14 and 5q12-q13. *Genomics* 19:31-37.

Porsolt, R. D., et al., "Behavioural despair in rats: a new model sensitive to antidepressant treatments" *Eur J Pharmacol* 47 (4): 379-391 (1978).

Presse, F., et al. (1992) Rat melanin-concentrating hormone messenger ribonucleic acid expression: marked changes during development and after stress and glucocorticoid stimuli. *Endocrinology* 131:1241-1250.

Qu, D., et al. (1996) A role for melanin-concentrating hormone in the central regulation of feeding behaviour. *Nature* 380:243-247.

Rossi, M., et al., (1997) Melanin-concentrating hormone acutely stimulates feeding, but chronic administration has no effect on body weight. *Endocrinology* 138:351-355.

Sahu, A. (1998) Evidence suggesting that galanin (GAL), melanin-concentrating hormone (MCH), neurotensin (NT), proopiomelanocortin (POMC) and neuropeptide Y (NPY) are targets of leptin signaling in the hypothalamus. *Endocrinology* 139 (2):795-798.

Sakurai, T., et al., (1998) Orexins and orexin receptors: A family of hypothalamic neuropeptides and G protein-coupled receptors that regulate feeding behavior. *Cell* 92:573-585.

Sanchez, M., et al., (1997) Melanin-concentrating hormone (MCH) antagonizes the effects of α-MSH and neuropeptide E-I on grooming and locomotor activities in the rat. *Peptides* 18:393-396.

Saito, Y., et al., "Molecular characterization of the melanin-concentrating-hormone receptor" *Nature* 400 (6741): 265-269 (1999).

Sherrington, R., et al., (1988) Localization of a susceptibility locus for schizophrenia on chromosome 5. *Nature* (London) 336:164-167.

Srebnik, M., et al., (1988) *J. Org. Chem.*, 53, 2916-2920.

Takekawa, S., et al., "T-226296: a novel, orally active and selective melanin-concentrating hormone receptor antagonist" *Eur J Pharmacol* 438 (3): 129-35 (2002)

Twells, R., et al., (1992) Chromosomal assignment of the locus causing olivo-ponto-cerebellar atrophy (SCA2) in a cuban founder population. *Cytogenet. Cell. Genet.* 61:262-265.

Westbrook, C. A., et al., (1992) Report of the second international workshop on human chromosome 5 mapping. *Cytogenet. Cell. Genet.* 61:225-231.

What is claimed is:

1. A compound wherein the compound has the structure:

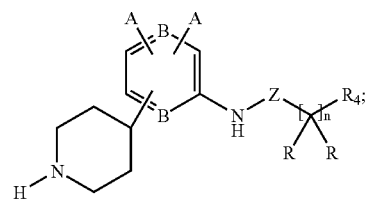

wherein each A is independently —H, —F, —Cl, —Br, —I, —CN, —NO$_2$, —OR$_3$ or straight chained or branched C$_1$-C$_7$ alkyl;

wherein Z is CO or SO$_2$;

wherein R$_4$ is —COR$_3$ or phenyl, wherein the phenyl is optionally substituted with one or more —F, —Cl, —Br, —I, —OR$_2$, or straight chained or branched C$_1$-C$_7$ alkyl;

wherein each R$_3$ is independently phenyl optionally substituted with one or more —F, —Cl, —Br, —I, —NO$_2$, —CN, —OR$_2$ or —NHR$_2$;

wherein each R$_2$ is independently straight chained or branched C$_1$-C$_7$ alkyl, or phenyl wherein the phenyl is optionally substituted with one or more —F, —Cl, —Br, —I, —NO$_2$, or —CN; and wherein n is an integer from 2 to 6 inclusive;

or a pharmaceutically acceptable salt thereof.

2. The compound of claim 1 wherein the compound has the structure:

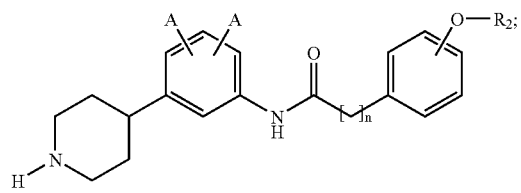

wherein R$_2$ is straight chained or branched C$_1$-C$_7$ alkyl, or phenyl wherein the phenyl is optionally substituted with one or more —F, —Cl, —Br, —I, —NO$_2$, or —CN.

3. The compound of claim 2 wherein the compound has the structure:

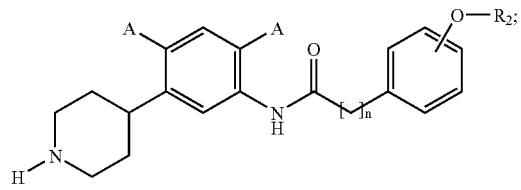

wherein R$_2$ is straight chained or branched C$_1$-C$_7$ alkyl; and wherein n is an integer from 3-6 inclusive.

4. The compound of claim 3 wherein the compound has the structure:

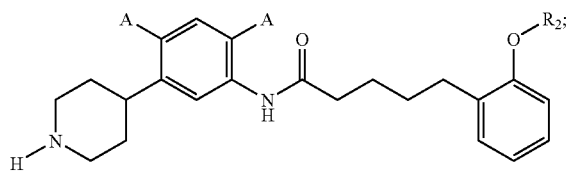

wherein each A is independently —H, —F, —Cl, —Br, or —I.

5. The compound of claim 4 wherein the compound has the structure:

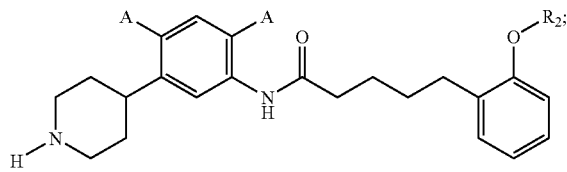

wherein each A is independently —H, —F, or —Cl; and
wherein $R_2$ is straight chained of branched $C_1$-$C_3$ alkyl.

6. The compound of claim 5 wherein the compound has the structure:

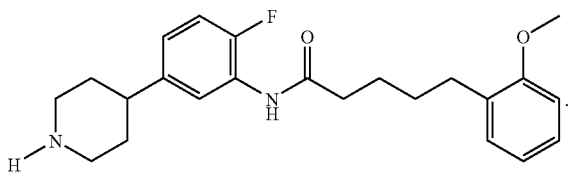

7. The compound of claim 5 wherein the compound has the structure:

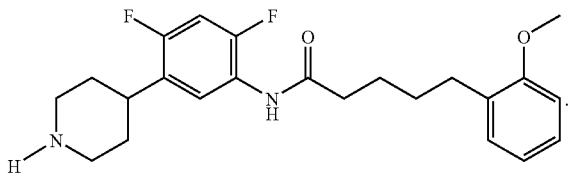

8. The compound of claim 1 wherein the compound has the structure:

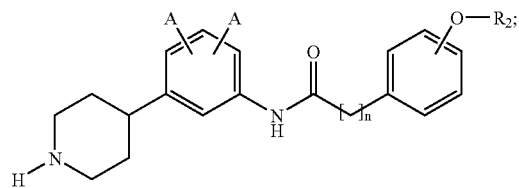

wherein $R_2$ is phenyl, wherein the phenyl is optionally substituted with one or more —F, —Cl, —Br, —I, —NO$_2$, or —CN; and wherein n is an integer from 2 to 6 inclusive.

9. The compound of claim 8 wherein the compound has the structure:

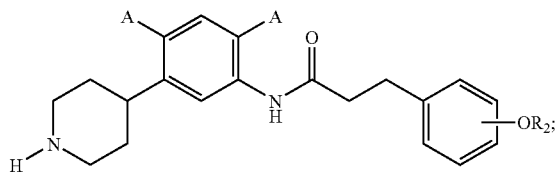

wherein each A is independently —H, —F, —Cl, —Br, or —I.

10. The compound of claim 9 wherein the compound has the structure:

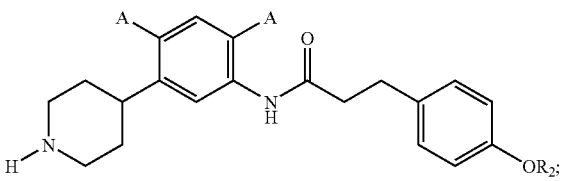

wherein each A is independently —H, —F, or —Cl; and
wherein $R_2$ is phenyl optionally substituted with one or more —F, —Cl, or —Br.

11. The compound of claim 10 wherein the compound has the structure:

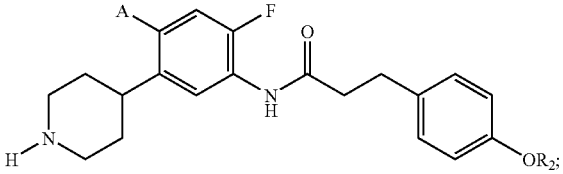

wherein each A is independently —H, —F, or —Cl; and
wherein $R_2$ is phenyl optionally substituted with one or more —F.

12. The compound of claim 11 wherein the compound has the structure:

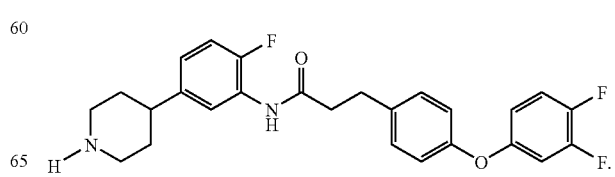

13. The compound of claim 1 wherein the compound has the structure:

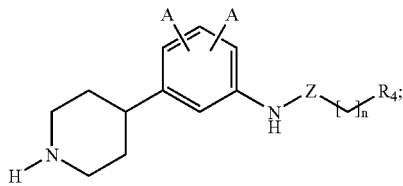

wherein each A is independently —H, —F, —Cl, —Br, —I, —CN, —NO₂, —OR₃ or straight chained or branched $C_1$-$C_7$ alkyl;
wherein Z is CO or $SO_2$;
wherein $R_4$ is —COR₃;
wherein each $R_3$ is independently phenyl optionally substituted with one or more —F, —Cl, —Br, —I, —NO₂, —CN, —OR₂, or —NHR₂;
wherein $R_2$ is straight chained or branched $C_1$-$C_7$ alkyl, or phenyl wherein the phenyl is optionally substituted with one or more —F, —Cl, —Br, —I, —NO₂, —CN; and
wherein n is an integer from 2 to 6 inclusive.

14. The compound of claim 13 wherein the compound has the structure:

wherein each A is independently —H, —F, —Cl, —Br, or —I;
wherein $R_4$ is —COR₃; and
wherein $R_3$ is phenyl optionally substituted with one or more —F, —Cl, —Br, —I, —NO₂, —CN, —OR₂ or —NHR₂.

15. The compound of claim 14 wherein the compound has the structure:

16. The compound of claim 14 wherein the compound has the structure:

wherein A is —H, —F, —Cl, —Br or —I; and
wherein $R_3$ is phenyl optionally substituted with one or more —F, —Cl, —Br or —I.

17. The compound of claim 16 wherein the compound has the structure:

18. The compound of claim 16 wherein the compound has the structure:

19. A pharmaceutical composition comprising a compound of claim 1 and a pharmaceutically acceptable carrier.

20. A pharmaceutical composition made by admixing a compound of claim 1 and a pharmaceutically acceptable carrier.

21. A process for making a pharmaceutical composition comprising admixing a compound of claim 1 and a pharmaceutically acceptable carrier.

* * * * *